US008722867B2

(12) United States Patent
Gruber et al.

(10) Patent No.: US 8,722,867 B2
(45) Date of Patent: *May 13, 2014

(54) GENE THERAPY VECTORS AND CYTOSINE DEAMINASES

(75) Inventors: Harry E. Gruber, Rancho Santa Fe, CA (US); Douglas J. Jolly, Encinitas, CA (US); Omar D. Perez, San Diego, CA (US); Christopher R. Logg, South Pasadena, CA (US)

(73) Assignee: Tocagen Inc., San Diego, CA (US)

( * ) Notice: Subject to any disclaimer, the term of this patent is extended or adjusted under 35 U.S.C. 154(b) by 253 days.

This patent is subject to a terminal disclaimer.

(21) Appl. No.: 13/072,705

(22) Filed: Mar. 26, 2011

(65) Prior Publication Data

US 2011/0217267 A1  Sep. 8, 2011

Related U.S. Application Data

(63) Continuation-in-part of application No. PCT/US2009/058510, filed on Sep. 26, 2009.

(60) Provisional application No. 61/100,666, filed on Sep. 26, 2008, provisional application No. 61/120,618, filed on Dec. 8, 2008, provisional application No. 61/186,823, filed on Jun. 13, 2009, provisional application No. 61/138,728, filed on Mar. 29, 2010.

(51) Int. Cl.
*A61K 48/00* (2006.01)
*C07H 21/00* (2006.01)
*C12N 15/867* (2006.01)
*A61K 35/76* (2006.01)
*C12N 15/63* (2006.01)

(52) U.S. Cl.
USPC ..... 536/23.2; 536/23.4; 536/24.1; 435/320.1; 435/69.1; 435/325; 435/227; 424/93.6; 424/93.7; 424/94.1; 514/44

(58) Field of Classification Search
CPC ...... C12N 15/62; C12N 15/867; C12N 15/85; C12N 15/63; C12N 15/79; C12N 9/00; A61K 48/0058; A61K 48/0066
See application file for complete search history.

(56) References Cited

U.S. PATENT DOCUMENTS

| | | | |
|---|---|---|---|
| 6,410,313 B1 | 6/2002 | Kasahara et al. |
| 6,899,871 B2 | 5/2005 | Kasahara et al. |
| 7,790,445 B2 | 9/2010 | Erbs |
| 2003/0121068 A1 | 6/2003 | Orchard et al. |
| 2005/0063945 A1 | 3/2005 | Paul |
| 2007/0264235 A1 | 11/2007 | Erbs |
| 2008/0008685 A1 | 1/2008 | Kasahara |
| 2010/0330051 A1 | 12/2010 | Erbs |

FOREIGN PATENT DOCUMENTS

| | | | |
|---|---|---|---|
| WO | 2010002937 A1 | | 1/2010 |
| WO | WO 2010036986 | * | 1/2010 |
| WO | 2010036986 A3 | | 4/2010 |
| WO | WO 2010002937 | * | 4/2010 |

OTHER PUBLICATIONS

Hiraoka et al, Therapeutic Efficacy of Replication-Competent Retrovirus Vector-Mediated Suicide Gene Therapy in a Multifocal Colorectal Cancer Metastasis Model, Cancer Res 2007; 67: (11), pp. 5345-5353.*
Tai et al, Single-Shot, Multicycle Suicide Gene Therapy by Replication-Competent Retrovirus Vectors Achieves Long-Term Survival Benefit in Experimental Glioma, Molecular Therapy vol. 12, No. 5, Nov. 2005, pp. 842-851.*
Logg et al, Tissue-Specific Transcriptional Targeting of a Replication-Competent Retroviral Vector, Journal of Virology, Dec. 2002, p. 12783-12791.*
Mechold et al, Codon optimization of the BirA enzyme gene leads to higher expression and an improved efficiency of biotinylation of target proteins in mammalian cells, Journal of Biotechnology 116 (2005) 245-249.*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Yin et al., "Insertion of sequences into the 3' untranslated region of a replication-competent spleen necrosis virus vector disrupts env gene expression," Arch Virol (1999) 144:73-87.
Aghi et al., "Synergistic Anticancer Effects of Ganciclovir/Thymidine Kinase and 5-Fluorocytosine/Cytosine Deaminase Gene Therapies," J. Natl. Cancer Inst. 90(5):370-380 (1998).
Akbulut et al., "Cytotoxic effect of replication-competent adenoviral vectors carrying L-plastin promoter regulated E1A and cytosine deaminase genes in cancers of the breast, ovary, and colon," Cancer Gene Therapy 10:388-395 (2003).
Akbulut et al., "Vector targeting makes 5-fluorouracil chemotherapy less toxic and more effective in animal models of epithelial neoplasms," 10(22):7738-46 (2004).
Anello et al., "Adenovirus Mediated Cytosine Deaminase Gene Transduction and 5-fluorocytosine Therapy Sensitizes Mouse Prostate Cancer to Irradiation," The Journal of Urology 164(6):2173-2177, 2000.
Blackburn et al., "Adenovrial transduction of a cytosine deaminase/thymidine kinase fusion gene into prostate carcinoma cells enhances prodrug and radiation sensitivity," International Journal of Cancer 82(2):293-297 (1999).
Bourbeau et al., "Suicide gene therapy with an adenovirus expressing the fusion gene CD::UPRT in human glioblastomas: different sensitivities correlate with p53 status," The Journal of Gene Medicine 6:1320-1332 (2004).
Bourbeau et al., "Improvement of antitumor activity by gene amplification with a replicating but nondisseminating adenovirus," 67(7):3387-95 (2007).

(Continued)

*Primary Examiner* — Maria Marvich
(74) *Attorney, Agent, or Firm* — Joseph R. Baker, Jr.; Gavrilovich, Dodd & Lindsey LLP

(57) ABSTRACT

This disclosure provides modified cytosine deaminases (CDs). The disclosure further relates to cells and vector expressing or comprising such modified CDs and methods of using such modified CDs in the treatment of disease and disorders.

44 Claims, 29 Drawing Sheets

(56) References Cited

OTHER PUBLICATIONS

Dias et al., "Targeted chemotherapy for head and neck cancer with a chimeric oncolytic adenovirus coding for bifunctional suicide protein FCU1," Clin. Cancer Res. 16(9):2540-9; Epub Apr. 13, 2010.
Foloppe et al., "Targeted delivery of a suicide gene to human colorectal tumors by a conditionally replicating vaccinia virus," Gene Ther. 15(20):1361-71 (2008); Epub May 15, 2008.
Paola et al., "Suicide Gene Therapy With the Yeast Fusion Gene Cytosine Deaminase/Uracil Phosphoribosyltransferase is Not Enough for Pancreatic Cancer," Pancreas 35(3):224-231 (2007).
Portsmouth et al., "Suicide genes for cancer thearpy," Mol. Aspects of Med. 28:4-41, 2007.
Wang et al., "Highly Efficient and Tumor-Restricted Gene Transfer to Malignant Gliomas by Replication-Competent Retroviral Vectors," Human Gene Therapy, 14:117-127, Jan. 20, 2003.
Katri et al., "Ccombination of cystosine deaminase with uracil phosphribosyl transferase leads to local and distant bystander effects against RM1 prostate cancer in mice," J. of Gene Medicine, 8:1086-1096, Jul. 11, 2006.
Bhattacharyya, Madhumita, "Gene therapy developments for pancreatic cancer," Best Pract. & Res. Clin. Gastro., 20(2):285-298, 2006.
Akimoto, M. et al., A new delivery system for 5-fluorouracil using prodrug and converting enzyme; Laboratory Science; Br J Ophthalmol 2002;86:581-586; www.bjophthalmol.com.
Erbs, P., et al., Modified vaccinia virus Ankara as a vector for suicide gene therapy; Cancer Gene Therapy (2008) 15, 18-28; Nature Publishing Group.
Erbs, P., et al., In Vivo Cancer Gene Therapy by Adenovirus-mediated Transfer of a Bifunctional Yeast Cytosine Deaminase/Uracil Phosphoribosyltransferase Fusion Gene; Cancer Res 2000;60:3813-3822; American Association for Cancer Research.
Erbs, P., et al., Characterization of the *Saccharomyces cerevisiae* FCY1 gene encoding cytosine deaminase and its homologue FCA1 of *Candida albicans*; Curr Genet 31: 1-6; Springer-Verlag 1997.
Fischer, U. et al., Mechanisms of thymidine kinase/ganciclovir and cytosine deaminase/5-fluorocytosine suicide gene therapy-induced cell death in glioma cells; Oncogene (2005) 24, 1231-1243; Nature Publishing Group.
Freytag, S. et al., Phase I Study of Replication-competent Adenovirus-mediated Double Suicide Gene Therapy for the Treatment of Locally Recurrent Prostate Cancer; Cancer Res 2002;62:4968-4976; American Association for Cancer Research.
Gene-Bank-AAG33626; cytosine deaminase-uracil phosphoribosylransferase fusion protein [synthetic contruct]; Gene-Bank-AAG33626; pp. 1-2; http://www.ncbi.nlm.nih.gov/protein/AAg33626, Aug. 15, 2012.
Gene-Bank-Y1SB_A; Chain A, Yeast Cytosine Deaminase Triple Mutant; pp. 1-2; http://www.ncbi.nlm.nih.gov/protein/1ySB_A, Aug. 15, 2012.
Guffey, M. et al., Engineered herpes simplex virus expressing bacterial cytosine deaminase for experimental therapy of brain tumors; Cancer Gene Therapy (2007) 14, 45-56; 2007 Nature Publishing Group.
Hiraoka, K., et al., Vector-Mediated Suicide Gene Therapy in a MultifocalTherapeutic Efficacy of Replication-Competent Retrovirus Colorectal Cancer Metastasis Model; AACR; Cancer Res 2007;67: (11); 5345-5353.;Published online Jun. 1, 2007; www.aacrjournals.org.
Hirschowitz, E., et al., In Vivo Adenvirus-Mediated Gene Transfer of the *Escherichia coli* Cytosine Deaminase Gene to Human Colon Carcinoma-Derived Tumors Induces Chemosensitivity to 5-Fluorocytosine; Human Gene Therapy 6:1055-1063; Mary Ann Liebert, Inc.; (Aug. 1995).
Huber, B., et al., Metabolism of 5-fluorocytosine to 5-fluorouracil in human colorectal tumor cells transduced with the cytosine deaminase gene: Significant antitumor effects when only a small percentage of tumor cells express cytosine deaminase; Proc. Natl. Acad. Sci. USA 91 (Aug. 1994); Medical Sciences; 8302-8306.

Ireton, G. et al., The Structure of *Escherichia coli* Cytosine Deaminase; J. Mol. Biol. (2002) 315, Academic Press; 687-697.
Ireton, G. et al., The 1.14A° Crystal Structure of Yeast Cytosine Deaminase: Evolution of Nucleotide Salvage Enzymes and Implications for Genetic Chemotherapy; Structure, vol. 11, 961-972, Aug. 2003, Elsevier Science Ltd.
Kaliberov, SA. et al., Mutation of *Escherichia coli* cytosine deaminase significantly enhances molecular chemotherapy of human glioma; Gene Therapy (2007) 14, 1111-1119; Nature Publishing Group; www.nature.com/gt.
Kaliberova, L. et al., Molecular chemotherapy of pancreatic cancer using novel mutant bacterial cytosine deaminase gene; Mol Cancer Ther 2008;7:2845-2854; American Association for Cancer Research; Published online Sep. 11, 2008.
Kawasaki, Y. et al., Replication-competent retrovirus vector-mediated prodrug activator gene therapy in experimental models of human malignant mesothelioma; Cancer Gene Ther.; Aug. 2011; 18(8); National Institutes of Health; 571-578.
Kern, L et al., The FUR1 gene of Sacckaromyces ceret, isiae: cloning, structure and expression of wild-type and mutant alleles; Gene, 88 (1990) 149-157; 1990 Elsevier Science Publishers B.V. (Biomedical Division).
Kikuchi, E. et al., Highly Efficient Gene Delivery for Bladder Cancers by Intravesically Administered Replication-Competent Retroviral Vectors; Clin Cancer Res 2007;13:4511-4518; American Association for Cancer Research; Published online Aug. 1, 2007.
Korkegian, A. et al., Computational Thermostabilization of an Enzyme; Science vol. 308; May 6, 2005; 857-860; www.sciencemag.org.
Kurozumi, K. et al., Apoptosis induction with 5-fluorocytosine/cytosine deaminase gene therapy for human malignant glioma cells mediated by adenovirus; Journal of Neuro-Oncology 66: 117-127, 2004; Kluwer Academic Publishers. Printed in the Netherlands.
Liu, Y. et al., Engineering conditionally replication-competent adenoviral vectors carrying the cytosine deaminase gene increases the infectivity and therapeutic effect for breast cancer gene therapy; Cancer Gene Therapy (2006) 13, 346-356; Nature Publishing Group.
Liu, Y. et al., Tumor-specific therapeutic effect induced by an oncolytic adenoviral vector containing heat shock protein 70 and prodrug activation genes; Gene Therapy (2006) 13, 1235-1243; Nature Publishing Group.
Mahan, S. et al., Random mutagenesis and selection of *Escherichia coli* cytosine deaminase for cancer gene therapy; Protein Engineering, Design & Selection vol. 17 No. 8 pp. 625-633, 2004;Published online Sep. 20, 2004.
Mahan, S. et al., Alanine-Scanning Mutagenesis Reveals a Cytosine Deaminase Mutant with Altered Substrate Preference; Biochemistry 2004, 43, 8957-8964; American Chemical Society.
Miller, C. et al., Intratumoral 5-Fluorouracil Produced by Cytosine Experimental Human Glioblastomas Deaminase/5-Fluorocytosine Gene Therapy Is Effective for Experimental Human Glioblastomas; Cancer Research 62, 773-780; Feb. 1, 2002, American Association for Cancer Research.
Mullen, G. et al., Transfer of the bacterial gene for cytosine deaminase to mammalian cells confers lethal sensitivity to 5-fluorocytosine: A negative selection system; Proc. Natl. Acad. Sci. USA; vol. 89, pp. 33-37, Jan. 1992; Medical Sciences.
Nakamura, H. et al., Multimodality Therapy with a Replication-conditional Herpes Simplex Virus 1 Mutant that Expresses Yeast Cytosine Deaminase for Intratumoral Conversion of 5-Fluorocytosine to 5-Fluorouracil; Cancer Res 2001;61:5447-5452; American Association for Cancer Research.
Negroni, L. et al., Treatment of colon cancer cells using the cytosine deaminase/5-fluorocytosine suicide system induces deaminase/5-fluorocytosine suicide system induces phosphorylation; Mol Cancer Ther 2007;6:2747-2756; American Association for Cancer Research.

(56) References Cited

OTHER PUBLICATIONS

Nishiyama, T. et al., Antineoplastic Effects in Rats of 5-Fluorocytosine in Combination with Cytosine Deaminase Capsules; Cancer Res 1985;45:1753-1761; American Association for Cancer Research.

Fogar, P. et al., Suicide Gene Therapy With the Yeast Fusion Gene Cytosine Deaminase/Uracil Phosphoribosyltransferase Is Not Enough for Pancreatic Cancer; Pancreas & vol. 35, No. 3, Oct. 2007; Lippincott Williams & Wilkins.

Poltoratsky, V., Recombinogenic Phenotype of Human Activation-Induced Cytosine Deaminas; J Immunol 2004; 172:4308-4313; http://www.jimmunol.org/content/172/7/4308; The American Association of Immunologists, Inc.

Shen, H. et al., Targeting of the Activation-Induced Cytosine Deaminase Is Strongly Influenced by the Sequence and Structure of the Targeted DNA; Molecular and Cellular Biology, Dec. 2005, p. 10815-10821 vol. 25, No. 24; doi:10.1128/MCB.25.24.10815-10821.2005; American Society for Microbiology.

Sotos, G. et al., Preclinical and clinical aspects of biomodulation of 5-fluorouracil; Cancer Treatment Reviews (1994) 20, 11-49; W. B. Saunders.

Stolworthy, T., et al., Yeast Cytosine Deaminase Mutants with Increased Thermostability Impart Sensitivity to 5-Fluorocytosine; J Mol Biol. Mar. 28, 2008; 377(3): 854-869; National Institutes of Health.

Tai, C. et al., Single-Shot, Multicycle Suicide Gene Therapy by Replication-Competent Retrovirus Vectors Achieves Long-Term Survival Benefit in Experimental Glioma; Molecular Therapy vol. 12, No. 5, Nov. 2005; The American Society of Gene Therapy.

Wallace, P. et al., Intratumoral Generation of 5-Fluorouracil Mediated by an Antibody-Cytosine Deaminase Conjugate in Combination with 5-Fluorocytosine; Cancer Res 1994;54:2719-2723; American Association for Cancer Research.

Wang, W. et al., Use of replication-competent retroviral vectors in an immunocompetent intracranial glioma model; Neurosurg. Focus; vol. 20; Apr. 2006; pp. 1-9.

Warmann, S. et al., Adenovirus-Mediated Cytosine Deaminase/5-Fluorocytosine Suicide Gene Therapy of Human Hepatoblastoma In Vitro; Pediatr Blood Cancer 2009;53:145-151; Wiley-Liss, Inc.

Zhang, J., et al., A Novel Oncolytic Adenovirus Expressing *Escherichia coli* Cytosine Deaminase Exhibits Potent Antitumor Effect on Human Solid Tumors; Cancer Biotherapy and Radiopharmaceuticals; vol. 25, No. 4, 2010; pp. 487-495; Mary Ann Liebert, Inc.

\* cited by examiner

```
    CMV Promotor (1-582)>>>
    |
1   TAGTTATTAATAGTAATCAATTACGGGGTCATTAGTTCATAGCCCATATATGGAGTTCCG  60
    ATCAATAATTATCATTAGTTAATGCCCCAGTAATCAAGTATCGGGTATATACCTCAAGGC 61  CGTTACATAACTTACGGTAAATGGCCCGCCTGGCTGACCGCCCAACGACCCCCGCCCATT  120
    GCAATGTATTGAATGCCATTTACCGGGCGGACCGACTGGCGGGTTGCTGGGGGCGGGTAA 121 GACGTCAATAATGACGTATGTTCCCATAGTAACGCCAATAGGGACTTTCCATTGACGTCA  180
    CTGCAGTTATTACTGCATACAAGGGTATCATTGCGGTTATCCCTGAAAGGTAACTGCAGT 181 ATGGGTGGAGTATTTACGGTAAACTGCCCACTTGGCAGTACATCAAGTGTATCATATGCC  240
    TACCCACCTCATAAATGCCATTTGACGGGTGAACCGTCATGTAGTTCACATAGTATACGG 241 AAGTACGCCCCCTATTGACGTCAATGACGGTAAATGGCCCGCCTGGCATTATGCCCAGTA  300
    TTCATGCGGGGATAACTGCAGTTACTGCCATTTACCGGGCGGACCGTAATACGGGTCAT Ecol05I
                                        |
                                        SnaBI
                                        |
                                        BstSNI
                                        |
301 CATGACCTTATGGGACTTTCCTACTTGGCAGTACATCTACGTATTAGTCATCGCTATTAC  360
    GTACTGGAATACCCTGAAAGGATGAACCGTCATGTAGATGCATAATCAGTAGCGATAATG 361 CATGGTGATGCGGTTTTGGCAGTACATCAATGGGCGTGGATAGCGGTTTGACTCACGGGG  420
    GTACCACTACGCCAAAACCGTCATGTAGTTACCCGCACCTATCGCCAAACTGAGTGCCCC 421 ATTTCCAAGTCTCCACCCCATTGACGTCAATGGGAGTTTGTTTTGGCACCAAAATCAACG  480
    TAAAGGTTCAGAGGTGGGGTAACTGCAGTTACCCTCAAACAAAACCGTGGTTTTAGTTGC 481 GGACTTTCCAAAATGTCGTAACAACTCCGCCCCATTGACGCAAATGGGCGGTAGGCGTGT  540
    CCTGAAAGGTTTTACAGCATTGTTGAGGCGGGGTAACTGCGTTTACCCGCCATCCGCACA R region (583-650)>>>
                                        |
541 ACGGTGGGAGGTCTATATAAGCAGAGCTGGTTTAGTGAACCGGCGCCAGTCCTCCGATTG  600
    TGCCACCCTCCAGATATATTCGTCTCGACCAAATCACTTGGCCGCGGTCAGGAGGCTAAC
```

FIGURE 1D-5

```
                                                   U5 region (651-1202)>>>
                                                   :
601   ACTGAGTCGCCCGGGTACCCGTGTATCCAATAAACCCTCTTGCAGTTGCATCCGACTTGT  660
      TGACTCAGCGGGCCCATGGGCACATAGGTTATTTGGGAGAACGTCAACGTAGGCTGAACA 661   GGTCTCGCTGTTCCTTGGGAGGGTCTCCTCTGAGTGATTGACTACCCGTCAGCGGGGGTC  720
      CCAGAGCGACAAGGAACCCTCCCAGAGGAGACTCACTAACTGATGGGCAGTCGCCCCCAG 721   TTTCATTTGGGGGCTCGTCCGGGATCGGGAGACCCCTGCCCAGGGACCACCGACCCACCA  780
      AAAGTAAACCCCGAGCAGGCCCTAGCCCTCTGGGGACGGGTCCCTGGTGGCTGGGTGGT 5'SS (788)
          :
781   CCGGGAGGTAAGCTGGCCAGCAACTTATCTGTGTCTGTCCGATTGTCTAGTGCTATCAC  840
      GGCCCTCCATTCGACCGGTCGTTGAATAGACACAGACAGGCTAACAGATCACAGATACTG

841   TGATTTTATGCGCCTGCGTCGGTACTAGTTAGCTAACTAGCTCTGTATCTGGCGGACCCG  900
```

FIGURE 1D-6

```
          ACTAAAATACGCGGACGCAGCCATGATCAATCGATTGATCGAGACATAGACCGCCTGGGC

901   TGGTGGAACTGACGAGTTCGGAACACCCGGCCGCAACCCTGGGAGACGTCCCAGGGACTT  960
        ACCACCTTGACTGCTCAAGCCTTGTGGGCCGGCGTTGGGACCCTCTGCAGGGTCCCTGAA

961   CGGGGGCCGTTTTTGTGGCCCGACCTGAGTCCAAAAATCCCGATCGTTTTGGACTCTTTG 1020
        GCCCCCGGCAAAAACACCGGGCTGGACTCAGGTTTTTAGGGCTAGCAAAACCTGAGAAAC

1021   GTGCACCCCCCTTAGAGGAGGGATATGTGGTTCTGGTAGGAGACGAGAACCTAAAACAGT 1080
        CACGTGGGGGGAATCTCCTCCCTATACACCAAGACCATCCTCTGCTCTTGGATTTTGTCA

1081   TCCCGCCTCCGTCTGAATTTTTGCTTTCGGTTTGGGACCGAAGCCGCGCCGCGCGTCTTG 1140
        AGGGCGGAGGCAGACTTAAAAACGAAAGCCAAACCCTGGCTTCGGCGCGGCGCGCAGAAC

1141   TCTGCTGCAGCATCGTTCTGTGTTGTCTCTGTCTGACTGTGTTTCTGTATTTGTCTGAGA 1200
        AGACGACGTCGTAGCAAGACACAACAGAGACAGACTGACACAAAGACATAAACAGACTCT gag(1203,2819)>>>
        |
 1201   ATATGGGCCAGACTGTTACCACTCCCTTAAGTTTGACCTTAGGTCACTGGAAAGATGTCG 1260
        TATACCCGGTCTGACAATGGTGAGGGAATTCAAACTGGAATCCAGTGACCTTTCTACAGC 1261   AGCGGATCGCTCACAACCAGTCGGTAGATGTCAAGAAGAGACGTTGGGTTACCTTCTGCT 1320
        TCGCCTAGCGAGTGTTGGTCAGCCATCTACAGTTCTTCTCTGCAACCCAATGGAAGACGA 1321   CTGCAGAATGGCCAACCTTTAACGTCGGATGGCCGCGAGACGGCACCTTTAACCGAGACC 1380
        GACGTCTTACCGGTTGGAAATTGCAGCCTACCGGCGCTCTGCCGTGGAAATTGGCTCTGG 1381   TCATCACCCAGGTTAAGATCAAGGTCTTTTCACCTGGCCCGCATGGACACCCAGACCAGG 1440
        AGTAGTGGGTCCAATTCTAGTTCCAGAAAAGTGGACCGGGCGTACCTGTGGGTCTGGTCC 1441   TCCCCTACATCGTGACCTGGGAAGCCTTGGCTTTTGACCCCCTCCCTGGGTCAAGCCCT 1500
        AGGGGATGTAGCACTGGACCCTTCGGAACCGAAAACTGGGGGGAGGGACCCAGTTCGGGA 1501   TTGTACACCCTAAGCCTCCGCCTCCTCTTCCTCCATCCGCCCCGTCTCTCCCCCTTGAAC 1560
        AACATGTGGGATTCGGAGGCGGAGGAGAAGGAGGTAGGCGGGGCAGAGAGGGGGAACTTG 1561   CTCCTCGTTCGACCCCGCCTCGATCCTCCCTTTATCCAGCCCTCACTCCTTCTCTAGGCG 1620
        GAGGAGCAAGCTGGGGCGGAGCTAGGAGGGAAATAGGTCGGGAGTGAGGAAGAGATCCGC 1621   CCAAACCTAAACCTCAAGTTCTTTCTGACAGTGGGGGGCCGCTCATCGACCTACTTACAG 1680
        GGTTTGGATTTGGAGTTCAAGAAAGACTGTCACCCCCGGCGAGTAGCTGGATGAATGTC 1681   AAGACCCCCGCCTTATAGGGACCCAAGACCACCCCCTTCCGACAGGGACGGAAATGGTG 1740
        TTCTGGGGGCGGAATATCCCTGGGTTCTGGTGGGGAAGGCTGTCCCTGCCTTTACCAC
```

FIGURE 1D-7

```
1741 GAGAAGCGACCCCTGCGGGAGAGGCACCGGACCCCTCCCCAATGGCATCTCGCCTACGTG 1800
     CTCTTCGCTGGGGACGCCCTCTCCGTGGCCTGGGGAGGGGTTACCGTAGAGCGGATGCAC

1801 GGAGACGGGAGCCCCCTGTGGCCGACTCCACTACCTCGCAGGCATTCCCCCTCCGCGCAG 1860
     CCTCTGCCCTCGGGGACACCGGCTGAGGTGATGGAGCGTCCGTAAGGGGAGGCGCGTC

1861 GAGGAAACGGACAGCTTCAATACTGGCCGTTCTCCTCTTCTGACCTTTACAACTGGAAAA 1920
     CTCCTTTGCCTGTCGAAGTTATGACCGGCAAGAGGAGAAGACTGGAAATGTTGACCTTTT

1921 ATAATAACCCTTCTTTTTCTGAAGATCCAGGTAAACTGACAGCTCTGATCGAGTCTGTTC 1980
     TATTATTGGGAAGAAAAAGACTTCTAGGTCCATTTGACTGTCGAGACTAGCTCAGACAAG

1981 TCATCACCCATCAGCCCACCTGGGACGACTGTCAGCAGCTGTTGGGGACTCTGCTGACCG 2040
     AGTAGTGGGTAGTCGGGTGGACCCTGCTGACAGTCGTCGACAACCCCTGAGACGACTGGC

3121 ACTTTGAGGGATCAGGAGCCCAGGTTATGGGACCAATGGGGCAGCCCCTGCAAGTGTTGA 3180
     TGAAACTCCCTAGTCCTCGGGTCCAATACCCTGGTTACCCCGTCGGGGACGTTCACAACT

3181 CCCTAAATATAGAAGATGAGCATCGGCTACATGAGACCTCAAAAGAGCCAGATGTTTCTC 3240
     GGGATTTATATCTTCTACTCGTAGCCGATGTACTCTGGAGTTTTCTCGGTCTACAAAGAG

3241 TAGGGTCCACATGGCTGTCTGATTTTCCTCAGGCCTGGGCGGAAACCGGGGGCATGGGAC 3300
     ATCCCAGGTGTACCGACAGACTAAAAGGAGTCCGGACCCGCCTTTGGCCCCCGTACCCTG

3'SS (3314)
3301 TGGCAGTTCGCCAAGCTCCTCTGATCATACCTCTGAAAGCAACCTCTACCCCCGTGTCCA 3360
     ACCGTCAAGCGGTTCGAGGAGACTAGTATGGAGACTTTCGTTGGAGATGGGGGCACAGGT

3361 TAAAACAATACCCCATGTCACAAGAAGCCAGACTGGGGATCAAGCCCCACATACAGAGAC 3420
     ATTTTGTTATGGGGTACAGTGTTCTTCGGTCTGACCCCTAGTTCGGGGTGTATGTCTCTG

3421 TGTTGGACCAGGGAATACTGGTACCCTGCCAGTCCCCCTGGAACACGCCCCTGCTACCCG 3480
     ACAACCTGGTCCCTTATGACCATGGGACGGTCAGGGGACCTTGTGCGGGGACGATGGGC

3481 TTAAGAAACCAGGGACTAATGATTATAGGCCTGTCCAGGATCTGAGAGAAGTCAACAAGC 3540
     AATTCTTTGGTCCCTGATTACTAATATCCGGACAGGTCCTAGACTCTCTTCAGTTGTTCG

3541 GGGTGGAAGACATCCACCCCACCGTGCCCAACCCTTACAACCTCTTGAGCGGGCTCCCAC 3600
     CCCACCTTCTGTAGGTGGGGTGGCACGGGTTGGGAATGTTGGAGAACTCGCCCGAGGGTG

3601 CGTCCCACCAGTGGTACACTGTGCTTGATTTAAAGGATGCCTTTTTCTGCCTGAGACTCC 3660
     GCAGGGTGGTCACCATGTGACACGAACTAAATTTCCTACGGAAAAGACGGACTCTGAGG

PfeI
                                                          |
                                                         TfiI
                                                          |
3661 ACCCCACCAGTCAGCCTCTCTTCGCCTTTGAGTGGAGAGATCCAGAGATGGGAATCTCAG 3720
     TGGGGTGGTCAGTCGGAGAGAAGCGGAAACTCACCTCTCTAGGTCTCTACCCTTAGAGTC
```

FIGURE 1D-8

```
                    MfeI
                    |
                    MunI
                    |
3721  GACAATTGACCTGGACCAGACTCCCACAGGGTTTCAAAAACAGTCCCACCCTGTTTGATG 3780
      CTGTTAACTGGACCTGGTCTGAGGGTGTCCCAAAGTTTTTGTCAGGGTGGGACAAACTAC

MroI
                                          |
                                          BseAI
                                          |
                                          Bsp13I
                                          |
                                          BspEI
                                          |
                                          Kpn2I
                                          |
                                          AccIII
                                          |
3781  AGGCACTGCACAGAGACCTAGCAGACTTCCGGATCCAGCACCCAGACTTGATCCTGCTAC 3840
      TCCGTGACGTGTCTCTGGATCGTCTGAAGGCCTAGGTCGTGGGTCTGAACTAGGACGATG

3841  AGTACGTGGATGACTTACTGCTGGCCGCCACTTCTGAGCTAGACTGCCAACAAGGTACTC 3900
      TCATGCACCTACTGAATGACGACCGGCGGTGAAGACTCGATCTGACGGTTGTTCCATGAG

3121  ACTTTGAGGGATCAGGAGCCCAGGTTATGGGACCAATGGGGCAGCCCCTGCAAGTGTTGA 3180
      TGAAACTCCCTAGTCCTCGGGTCCAATACCCTGGTTACCCCGTCGGGGACGTTCACAACT

3181  CCCTAAATATAGAAGATGAGCATCGGCTACATGAGACCTCAAAAGAGCCAGATGTTTCTC 3240
      GGGATTTATATCTTCTACTCGTAGCCGATGTACTCTGGAGTTTTCTCGGTCTACAAAGAG

3241  TAGGGTCCACATGGCTGTCTGATTTTCCTCAGGCCTGGGCGGAAACCGGGGGCATGGGAC 3300
      ATCCCAGGTGTACCGACAGACTAAAAGGAGTCCGGACCCGCCTTTGGCCCCCGTACCCTG

3'SS (3314)
           |
3301  TGGCAGTTCGCCAAGCTCCTCTGATCATACCTCTGAAAGCAACCTCTACCCCCGTGTCCA 3360
      ACCGTCAAGCGGTTCGAGGAGACTAGTATGGAGACTTTCGTTGGAGATGGGGCACAGGT

3361  TAAAACAATACCCCATGTCACAAGAAGCCAGACTGGGGATCAAGCCCCACATACAGAGAC 3420
      ATTTTGTTATGGGGTACAGTGTTCTTCGGTCTGACCCCTAGTTCGGGGTGTATGTCTCTG

3421  TGTTGGACCAGGGAATACTGGTACCCTGCCAGTCCCCCTGGAACACGCCCTGCTACCCG 3480
      ACAACCTGGTCCCTTATGACCATGGGACGGTCAGGGGGACCTTGTGCGGGACGATGGGC

3481  TTAAGAAACCAGGGACTAATGATTATAGGCCTGTCCAGGATCTGAGAGAAGTCAACAAGC 3540
      AATTCTTTGGTCCCTGATTACTAATATCCGGACAGGTCCTAGACTCTCTTCAGTTGTTCG
```

FIGURE 1D-9

```
3541  GGGTGGAAGACATCCACCCCACCGTGCCCAACCCTTACAACCTCTTGAGCGGGCTCCCAC  3600
      CCCACCTTCTGTAGGTGGGGTGGCACGGGTTGGGAATGTTGGAGAACTCGCCCGAGGGTG

3601  CGTCCCACCAGTGGTACACTGTGCTTGATTTAAAGGATGCCTTTTTCTGCCTGAGACTCC  3660
      GCAGGGTGGTCACCATGTGACACGAACTAAATTTCCTACGGAAAAAGACGGACTCTGAGG

PfeI
                                                               |
                                                              TfiI
                                                               |
3661  ACCCCACCAGTCAGCCTCTCTTCGCCTTTGAGTGGAGAGATCCAGAGATGGGAATCTCAG  3720
      TGGGGTGGTCAGTCGGAGAGAAGCGGAAACTCACCTCTCTAGGTCTCTACCCTTAGAGTC

MfeI
       |
      MunI
       |
3721  GACAATTGACCTGGACCAGACTCCCACAGGGTTTCAAAAACAGTCCCACCCTGTTTGATG  3780
      CTGTTAACTGGACCTGGTCTGAGGGTGTCCCAAAGTTTTTGTCAGGGTGGGACAAACTAC

MroI
                               |
                              BseAI
                               |
                              Bsp13I
                               |
                              BspEI
                               |
                              Kpn2I
                               |
                              AccIII
                               |
3781  AGGCACTGCACAGAGACCTAGCAGACTTCCGGATCCAGCACCCAGACTTGATCCTGCTAC  3840
      TCCGTGACGTGTCTCTGGATCGTCTGAAGGCCTAGGTCGTGGGTCTGAACTAGGACGATG

3841  AGTACGTGGATGACTTACTGCTGGCCGCCACTTCTGAGCTAGACTGCCAACAAGGTACTC  3900
      TCATGCACCTACTGAATGACGACCGGCGGTGAAGACTCGATCTGACGGTTGTTCCATGAG
```

FIGURE 1D-10

3901 GGGCCCTGTTACAAACCCTAGGGAACCTCGGGTATCGGGCCTCGGCCAAGAAAGCCCAAA 3960
     CCCGGGACAATGTTTGGGATCCCTTGGAGCCCATAGCCCGGAGCCGGTTCTTTCGGGTTT

3961 TTTGCCAGAAACAGGTCAAGTATCTGGGGTATCTTCTAAAAGAGGGTCAGAGATGGCTGA 4020
     AAACGGTCTTTGTCCAGTTCATAGACCCCATAGAAGATTTTCTCCCAGTCTCTACCGACT

4021 CTGAGGCCAGAAAAGAGACTGTGATGGGGCAGCCTACTCCGAAGACCCCTCGACAACTAA 4080
     GACTCCGGTCTTTTCTCTGACACTACCCCGTCGGATGAGGCTTCTGGGGAGCTGTTGATT

4081 GGGAGTTCCTAGGGACGGCAGGCTTCTGTCGCCTCTGGATCCCTGGGTTTGCAGAAATGG 4140
     CCCTCAAGGATCCCTGCCGTCCGAAGACAGCGGAGACCTAGGGACCCAAACGTCTTTACC

4141 CAGCCCCCTTGTACCCTCTCACCAAAACGGGGACTCTGTTTAATTGGGGCCCAGACCAAC 4200
     GTCGGGGGAACATGGGAGAGTGGTTTTGCCCCTGAGACAAATTAACCCCGGGTCTGGTTG

4201 AAAAGGCCTATCAAGAAATCAAGCAAGCTCTTCTAACTGCCCCAGCCCTGGGGTTGCCAG 4260
     TTTTCCGGATAGTTCTTTAGTTCGTTCGAGAAGATTGACGGGGTCGGGACCCCAACGGTC

SalI
                               |
4261 ATTTGACTAAGCCCTTTGAACTCTTTGTCGACGAGAAGCAGGGCTACGCCAAAGGTGTCC 4320
     TAAACTGATTCGGGAAACTTGAGAAACAGCTGCTCTTCGTCCCGATGCGGTTTCCACAGG

4321 TAACGCAAAAACTGGGACCTTGGCCGTCGGCCGGTGGCCTACCTGTCCAAAAAGCTAGACC 4380
     ATTGCGTTTTTGACCCTGGAACCGCAGCCGGCCACCGGATGGACAGGTTTTTCGATCTGG

4381 CAGTAGCAGCTGGGTGGCCCCCTTGCCTACGGATGGTAGCAGCCATTGCCGTACTGACAA 4440
     GTCATCGTCGACCCACCGGGGGAACGGATGCCTACCATCGTCGGTAACGGCATGACTGTT

4441 AGGATGCAGGCAAGCTAACCATGGGACAGCCACTAGTCATTCTGGCCCCCATGCAGTAG 4500
     TCCTACGTCCGTTCGATTGGTACCCTGTCGGTGATCAGTAAGACCGGGGGTACGTCATC

4501 AGGCACTAGTCAAACAACCCCCGACCGCTGGCTTTCCAACGCCCGGATGACTCACTATC 4560
     TCCGTGATCAGTTTGTTGGGGGCTGGCGACCGAAAGGTTGCGGGCCTACTGAGTGATAG

4561 AGGCCTTGCTTTTGGACACGGACCGGGTCCAGTTCGGACCGGTGGTAGCCCTGAACCCGG 4620
     TCCGGAACGAAAACCTGTGCCTGGCCCAGGTCAAGCCTGGCCACCATCGGGACTTGGGCC

4621 CTACGCTGCTCCCACTGCCTGAGGAAGGGCTGCAACACAACTGCCTTGATATCCTGGCCG 4680
     GATGCGACGAGGGTGACGGACTCCTTCCCGACGTTGTGTTGACGGAACTATAGGACCGGC

4681 AAGCCCACGGAACCCGACCCGACCTAACGGACCAGCCGCTCCCAGACGCCGACCACACCT 4740
     TTCGGGTGCCTTGGGCTGGGCTGGATTGCCTGGTCGGCGAGGGTCTGCGGCTGGTGTGGA

4741 GGTACACGGATGGAAGCAGTCTCTTACAAGAGGGACAGCGTAAGGCGGGAGCTGCGGTGA 4800
     CCATGTGCCTACCTTCGTCAGAGAATGTTCTCCCTGTCGCATTCCGCCCTCGACGCCACT

FIGURE 1D-11

```
                                        BlpI
                                        |
                                        CelII
                                        |
                                        Bpu1102I
                                        |
                                        Bsp1720I
                                        |
4801 CCACCGAGACCGAGGTAATCTGGGCTAAAGCCCTGCCAGCCGGGACATCCGCTCAGCGGG 4860
     GGTGGCTCTGGCTCCATTAGACCCGATTTCGGGACGGTCGGCCCTGTAGGCGAGTCGCCC

4861 CTGAACTGATAGCACTCACCCAGGCCCTAAAGATGGCAGAAGGTAAGAAGCTAAATGTTT 4920
     GACTTGACTATCGTGAGTGGGTCCGGGATTTCTACCGTCTTCCATTCTTCGATTTACAAA

4921 ATACTGATAGCCGTTATGCTTTTGCTACTGCCCATATCCATGGAGAAATATACAGAAGGC 4980
     TATGACTATCGGCAATACGAAAACGATGACGGGTATAGGTACCTCTTTATATGTCTTCCG

4981 GTGGGTTGCTCACATCAGAAGGCAAAGAGATCAAAAATAAAGACGAGATCTTGGCCCTAC 5040
     CACCCAACGAGTGTAGTCTTCCGTTTCTCTAGTTTTTATTTCTGCTCTAGAACCGGGATG

5041 TAAAAGCCCTCTTTCTGCCCAAAAGACTTAGCATAATCCATTGTCCAGGACATCAAAAGG 5100
     ATTTTCGGGAGAAAGACGGGTTTTCTGAATCGTATTAGGTAACAGGTCCTGTAGTTTTCC

5101 CACACAGCGCCGAGGCTAGAGCCAACGGATGGCTGACCAAGCGGCCCGAAAGGCAGCCA 5160
     CTGTGTCGCGGCTCCGATCTCGGTTGGCCTACCGACTGGTTCGCCGGGCTTTCCGTCGGT

5161 TCACAGAGACTCCAGACACCTCTACCCTCCTCATAGAAAATTCATCACCCTACACCTCAG 5220
     AGTGTCTCTGAGGTCTGTGGAGATGGGAGGAGTATCTTTTAAGTAGTGGGATGTGGAGTC

5221 AACATTTTCATTACACAGTGACTGATATAAAGGACCTAACCAAGTTGGGGGCCATTTATG 5280
     TTGTAAAAGTAATGTGTCACTGACTATATTTCCTGGATTGGTTCAACCCCCGGTAAATAC

5281 ATAAAACAAAGAAGTATTGGGTCTACCAAGGAAAACCTGTGATGCCTGACCAGTTTACTT 5340
     TATTTTGTTTCTTCATAACCCAGATGGTTCCTTTTGGACACTACGGACTGGTCAAATGAA

5341 TTGAATTATTAGACTTTCTTCATCAGCTGACTCACCTCAGCTTCTCAAAAATGAAGGCTC 5400
     AACTTAATAATCTGAAAGAAGTAGTCGACTGAGTGGAGTCGAAGAGTTTTTACTTCCGAG

5401 TCCTAGAGAGAAGCCACAGTCCCTACTACATGCTGAACCGGGATCGAACACTCAAAAATA 5460
     AGGATCTCTCTTCGGTGTCAGGGATGATGTACGACTTGGCCCTAGCTTGTGAGTTTTTAT
```

FIGURE 1D-12

```
5461  TCACTGAGACCTGCAAAGCTTGTGCACAAGTCAACGCCAGCAAGTCTGCCGTTAAACAGG  5520
      AGTGACTCTGGACGTTTCGAACACGTGTTCAGTTGCGGTCGTTCAGACGGCAATTTGTCC

SacII
                            |
                          SgrBI
                            |
                          Cfr42I
                            |
                          Sfr303I
                            |
                          KspI
                            |
5521  GAACTAGGGTCCGCGGGCATCGGCCCGGCACTCATTGGGAGATCGATTTCACCGAGATAA  5580
      CTTGATCCCAGGCGCCCGTAGCCGGGCCGTGAGTAACCCTCTAGCTAAAGTGGCTCTATT

5581  AGCCCGGATTGTATGGCTATAAATATCTTCTAGTTTTTATAGATACCTTTTCTGGCTGGA  5640
      TCGGGCCTAACATACCGATATTTATAGAAGATCAAAAATATCTATGGAAAAGACCGACCT

5641  TAGAAGCCTTCCCAACCAAGAAAGAAACCGCCAAGGTCGTAACCAAGAAGCTACTAGAGG  5700
      ATCTTCGGAAGGGTTGGTTCTTTCTTTGGCGGTTCCAGCATTGGTTCTTCGATGATCTCC

PaeI
                            |
                          BbuI
                            |
                          SpaHI
                            |
                          SphI
                            |
5701  AGATCTTCCCCAGGTTCGGCATGCCTCAGGTATTGGGAACTGACAATGGGCCTGCCTTCG  5760
      TCTAGAAGGGGTCCAAGCCGTACGGAGTCCATAACCCTTGACTGTTACCCGGACGGAAGC

6901  CTTCCAAGGGGCTACTCGAGGGGGCAGATGCAACCCTCTAGTCCTAGAATTCACTGATGC  6960
      GAAGGTTCCCCGATGAGCTCCCCCGTCTACGTTGGGAGATCAGGATCTTAAGTGACTACG

6961  AGGAAAAAAGGCTAACTGGGACGGGCCCAAATCGTGGGGACTGAGACTGTACCGGACAGG  7020
      TCCTTTTTTCCGATTGACCCTGCCCGGGTTTAGCACCCCTGACTCTGACATGGCCTGTCC

7021  AACAGATCCTATTACCATGTTCTCCCTGACCCGGCAGGTCCTTAATGTGGGACCCCGAGT  7080
      TTGTCTAGGATAATGGTACAAGAGGGACTGGGCCGTCCAGGAATTACACCCTGGGGCTCA

7081  CCCCATAGGGCCCAACCCAGTATTACCCGACCAAAGACTCCCTTCCTCACCAATAGAGAT  7140
      GGGGTATCCCGGGTTGGGTCATAATGGGCTGGTTTCTGAGGGAAGGAGTGGTTATCTCTA

7141  TGTACCGGCTCCACAGCCACCTAGCCCCCTCAATACCAGTTACCCCCCTTCCACTACCAG  7200
      ACATGGCCGAGGTGTCGGTGGATCGGGGAGTTATGGTCAATGGGGGAAGGTGATGGTC

7201  TACACCCTCAACCTCCCCTACAAGTCCAAGTGTCCCACAGCCACCCCCAGGAACTGGAGA  7260
      ATGTGGGAGTTGGAGGGGATGTTCAGGTTCACAGGGTGTCGGTGGGGTCCTTGACCTCT

7261  TAGACTACTAGCTCTAGTCAAAGGAGCCTATCAGGCGCTTAACCTCACCAATCCCGACAA  7320
      ATCTGATGATCGAGATCAGTTTCCTCGGATAGTCCGCGAATTGGAGTGGTTAGGGCTGTT
```

FIGURE 1D-13

```
7321 GACCCAAGAATGTTGGCTGTGCTTAGTGTCGGGACCTCCTTATTACGAAGGAGTAGCGGT 7380
     CTGGGTTCTTACAACCGACACGAATCACAGCCCTGGAGGAATAATGCTTCCTCATCGCCA

7381 CGTGGGCACTTATACCAATCATTCCACCGCTCCGGCCAACTGTACGGCCACTTCCCAACA 7440
     GCACCCGTGAATATGGTTAGTAAGGTGGCGAGGCCGGTTGACATGCCGGTGAAGGGTTGT
```

EcoT22I
                                      |
                                    NsiI
                                      |
                                    Mph1103I
                                      |
                                    Zsp2I
                                      |
                                    BfrBI
                                     | |
```
7441 TAAGCTTACCCTATCTGAAGTGACAGGACAGGGCCTATGCATGGGGCAGTACCTAAAAC 7500
     ATTCGAATGGGATAGACTTCACTGTCCTGTCCCGGATACGTACCCCCGTCATGGATTTTG
```

NaeI
                                      |
                                    PdiI
                                      |
                                    MroNI
                                     | |
                                    NgoMIV
                                     | |
```
7501 TCACCAGGCCTTATGTAACACCACCCAAAGCGCCGGCTCAGGATCCTACTACCTTGCAGC 7560
     AGTGGTCCGGAATACATTGTGGTGGGTTTCGCGGCCGAGTCCTAGGATGATGGAACGTCG
```

AleI
                                                                |
                                                              OliI
                                                                |
```
7561 ACCCGCCGGAACAATGTGGGCTTGCAGCACTGGATTGACTCCCTGCTTGTCCACCACGGT 7620
     TGGGCGGCCTTGTTACACCCGAACGTCGTGACCTAACTGAGGGACGAACAGGTGGTGCCA

7621 GCTCAATCTAACCACAGATTATTGTGTATTAGTTGAACTCTGGCCCAGAGTAATTTACCA 7680
     CGAGTTAGATTGGTGTCTAATAACACATAATCAACTTGAGACCGGGTCTCATTAAATGGT
```

FIGURE 1D-14

```
6901  CTTCCAAGGGGCTACTCGAGGGGGCAGATGCAACCCTCTAGTCCTAGAATTCACTGATGC  6960
      GAAGGTTCCCCGATGAGCTCCCCGTCTACGTTGGGAGATCAGGATCTTAAGTGACTACG

6961  AGGAAAAAAGGCTAACTGGGACGGGCCCAAATCGTGGGGACTGAGACTGTACCGGACAGG  7020
      TCCTTTTTTCCGATTGACCCTGCCCGGGTTTAGCACCCCTGACTCTGACATGGCCTGTCC

7021  AACAGATCCTATTACCATGTTCTCCCTGACCCGGCAGGTCCTTAATGTGGGACCCCGAGT  7080
      TTGTCTAGGATAATGGTACAAGAGGGACTGGGCCGTCCAGGAATTACACCCTGGGGCTCA

7081  CCCCATAGGGCCCAACCCAGTATTACCCGACCAAAGACTCCCTTCCTCACCAATAGAGAT  7140
      GGGGTATCCCGGGTTGGGTCATAATGGGCTGGTTTCTGAGGGAAGGAGTGGTTATCTCTA

7141  TGTACCGGCTCCACAGCCACCTAGCCCCCTCAATACCAGTTACCCCCCTTCCACTACCAG  7200
      ACATGGCCGAGGTGTCGGTGGATCGGGGGAGTTATGGTCAATGGGGGGAAGGTGATGGTC

7201  TACACCCTCAACCTCCCCTACAAGTCCAAGTGTCCACAGCCACCCCCAGGAACTGGAGA  7260
      ATGTGGGAGTTGGAGGGGATGTTCAGGTTCACAGGGTGTCGGTGGGGTCCTTGACCTCT

7261  TAGACTACTAGCTCTAGTCAAAGGAGCCTATCAGGCGCTTAACCTCACCAATCCCGACAA  7320
      ATCTGATGATCGAGATCAGTTTCCTCGGATAGTCCGCGAATTGGAGTGGTTAGGGCTGTT

7321  GACCCAAGAATGTTGGCTGTGCTTAGTGTCGGGACCTCCTTATTACGAAGGAGTAGCGGT  7380
      CTGGGTTCTTACAACCGACACGAATCACAGCCCTGGAGGAATAATGCTTCCTCATCGCCA

7381  CGTGGGCACTTATACCAATCATTCCACCGCTCCGGCCAACTGTACGGCCACTTCCCAACA  7440
      GCACCCGTGAATATGGTTAGTAAGGTGGCGAGGCCGGTTGACATGCCGGTGAAGGGTTGT

EcoT22I
                                                |
                                              NsiI
                                                |
                                              Mph1103I
                                                |
                                              Zsp2I
                                                |
                                              BfrBI
                                               | |
7441  TAAGCTTACCCTATCTGAAGTGACAGGACAGGGCCTATGCATGGGGGCAGTACCTAAAAC  7500
      ATTCGAATGGGATAGACTTCACTGTCCTGTCCCGGATACGTACCCCCGTCATGGATTTTG

NaeI
                                                |
                                              PdiI
                                                |
                                              MroNI
                                               | |
                                              NgoMIV
                                               | |
7501  TCACCAGGCCTTATGTAACACCACCCAAAGCGCCGGCTCAGGATCCTACTACCTTGCAGC  7560
      AGTGGTCCGGAATACATTGTGGTGGGTTTCGCGGCCGAGTCCTAGGATGATGGAACGTCG
```

FIGURE 1D-15

```
                                                                    AleI
                                                                    |
                                                                    OliI
                                                                    |
     7561   ACCCGCCGGAACAATGTGGGCTTGCAGCACTGGATTGACTCCCTGCTTGTCCACCACGGT 7620
            TGGGCGGCCTTGTTACACCCGAACGTCGTGACCTAACTGAGGGACGAACAGGTGGTGCCA

7621   GCTCAATCTAACCACAGATTATTGTGTATTAGTTGAACTCTGGCCCAGAGTAATTTACCA 7680
            CGAGTTAGATTGGTGTCTAATAACACATAATCAACTTGAGACCGGGTCTCATTAAATGGT

7681   CTCCCCCGATTATATGTATGGTCAGCTTGAACAGCGTACCAAATATAAAGAGAGCCAGT 7740
            GAGGGGGCTAATATACATACCAGTCGAACTTGTCGCATGGTTTATATTTCTCTCGGTCA

7741   ATCATTGACCCTGGCCCTTCTACTAGGAGGATTAACCATGGGAGGGATTGCAGCTGGAAT 7800
            TAGTAACTGGGACCGGGAAGATGATCCTCCTAATTGGTACCCTCCCTAACGTCGACCTTA

7801   AGGGACGGGGACCACTGCCTTAATTAAAACCCAGCAGTTTGAGCAGCTTCATGCCGCTAT 7860
            TCCCTGCCCCTGGTGACGGAATTAATTTTGGGTCGTCAAACTCGTCGAAGTACGGCGATA

7861   CCAGACAGACCTCAACGAAGTCGAAAAGTCAATTACCAACCTAGAAAAGTCACTGACCTC 7920
            GGTCTGTCTGGAGTTGCTTCAGCTTTTCAGTTAATGGTTGGATCTTTTCAGTGACTGGAG

7921   GTTGTCTGAAGTAGTCCTACAGAACCGCAGAGGCCTAGATTTGCTATTCCTAAAGGAGGG 7980
            CAACAGACTTCATCAGGATGTCTTGGCGTCTCCGGATCTAAACGATAAGGATTTCCTCCC

7981   AGGTCTCTGCGCAGCCCTAAAAGAAGAATGTTGTTTTTATGCAGACCACACGGGGCTAGT 8040
            TCCAGAGACGCGTCGGGATTTTCTTCTTACAACAAAAATACGTCTGGTGTGCCCCGATCA

8041   GAGAGACAGCATGGCCAAATTAAGAGAAAGGCTTAATCAGAGACAAAAACTATTTGAGAC 8100
            CTCTCTGTCGTACCGGTTTAATTCTCTTTCCGAATTAGTCTCTGTTTTTGATAAACTCTG

NspV
                            |
                            BstBI
                            |
                            Bsp119I
                            |
                            AsuII
                            |
                            Csp45I
                            |
                            SfuI
                            |
                            Bpu14I
                            |
                            BspT104I
                            |
     8101   AGGCCAAGGATGGTTCGAAGGGCTGTTTAATAGATCCCCCTGGTTTACCACCTTAATCTC 8160
            TCCGGTTCCTACCAAGCTTCCCGACAAATTATCTAGGGGGACCAAATGGTGGAATTAGAG
```

FIGURE 1D-16

```
8161  CACCATCATGGGACCTCTAATAGTACTCTTACTGATCTTACTCTTTGGACCTTGCATTCT  8220
      GTGGTAGTACCCTGGAGATTATCATGAGAATGACTAGAATGAGAAACCTGGAACGTAAGA

8221  CAATCGATTGGTCCAATTTGTTAAAGACAGGATCTCAGTGGTCCAGGCTCTGGTTTTGAC  8280
      GTTAGCTAACCAGGTTAAACAATTTCTGTCCTAGAGTCACCAGGTCCGAGACCAAAACTG
                                                     IRES reg(8327,8876)>>>
                                                           |
                                                        MluI(8325)
                                                         | |
8281  TCAGCAATATCACCAGCTAAAACCCATAGAGTACGAGCCATGAACGCGTTACTGGCCGAA  8340
      AGTCGTTATAGTGGTCGATTTTGGGTATCTCATGCTCGGTACTTGCGCAATGACCGGCTT ires_emcv reg(8378,8876)>>>
                     |
8341  GCCGCTTGGAATAAGGCCGGTGTGCGTTTGTCTATATGTTATTTTCCACCATATTGCCGT  8400
      CGGCGAACCTTATTCCGGCACACGCAAACAGATATACAATAAAAGGTGGTATAACGGCA 8401  CTTTTGGCAATGTGAGGGCCCGGAAACCTGGCCCTGTCTTCTTGACGAGCATTCCTAGGG  8460
      GAAAACCGTTACACTCCCGGGCCTTTGGACCGGGACAGAAGAACTGCTCGTAAGGATCCC 8461  GTCTTTCCCCTCTCGCCAAAGGAATGCAAGGTCTGTTGAATGTCGTGAAGGAAGCAGTTC  8520
      CAGAAAGGGGAGAGCGGTTTCCTTACGTTCCAGACAACTTACAGCACTTCCTTCGTCAAG 8521  CTCTGGAAGCTTCTTGAAGACAAACAACGTCTGTAGCGACCCTTTGCAGGCAGCGGAACC  8580
      GAGACCTTCGAAGAACTTCTGTTTGTTGCAGACATCGCTGGGAAACGTCCGTCGCCTTGG 8581  CCCCACCTGGCGACAGGTGCCTCTGCGGCCAAAAGCCACGTGTATAAGATACACCTGCAA  8640
      GGGGTGGACCGCTGTCCACGGAGACGCCGGTTTTCGGTGCACATATTCTATGTGGACGTT 8641  AGGCGGCACAACCCCAGTGCCACGTTGTGAGTTGGATAGTTGTGGAAAGAGTCAAATGGC  8700
      TCCGCCGTGTTGGGGTCACGGTGCAACACTCAACCTATCAACACCTTTCTCAGTTTACCG 8701  TCTCCTCAAGCGTATTCAACAAGGGGCTGAAGGATGCCCAGAAGGTACCCCATTGTATGG  8760
      AGAGGAGTTCGCATAAGTTGTTCCCCGACTTCCTACGGGTCTTCCATGGGTAACATACC 8761  GATCTGATCTGGGCCTCGGTGCACATGCTTTACATGTGTTTAGTCGAGGTTAAAAAAAC  8820
      CTAGACTAGACCCCGGAGCCACGTGTACGAAATGTACACAAATCAGCTCCAATTTTTTG
```

FIGURE 1D-17

```
                                                           yCD2 (8877,9353)>>>
                                                           |
                                                           PsiI(8874)
                                                           | |
      8821  GTCTAGGCCCCCGAACCACGGGGACGTGGTTTTCCTTTGAAAAACACGATTATAANTGC 8880
            CAGATCCGGGGGCTTGGTGCCCCTGCACCAAAAGGAAACTTTTTGTGCTAATATTTACC

8881  TGACCGGCGGCATGGCCTCCAAGTCGGATCAAAAGGGCATGGATATCGCTTACGAGGACG 8940
            ACTGGCCGCCGTACCGGAGGTTCAGCCTAGTTTTCCCGTACCTATAGCGAATGCTCCTGC

8941  CCCTGCTGGGCTACAAGGAGGGCGGGCTGCCTATCGGCGGCTGTCTGATCAACAACAAGC 9000
            GGGACGACCCGATGTTCCTCCCGCCGCACGGATAGCCGCCGACAGACTAGTTGTTGTTCG

9001  ACGGCAGTGTGCTCGGCACGGGCCACAACATGAGCTTCCAGAAGGGCTCCGCCACCCTGC 9060
            TGCCGTCACACGAGCCGTGCCCGGTGTTGTACTCGAAGGTCTTCCCGAGGCGGTGGGACG

9061  ACGGCGAGATCTCCACCCTGGAGAACTGTGGCAGGCTGGAGGGCAAGGTGTACAAGGACA 9120
            TGCCGCTCTAGAGGTGGGACCTCTTGACACCGTCCGACCTCCCGTTCCACATGTTCCTGT

9121  CCACCCTGTACACCACCCTGTCCCCTTGTGACATGTGTACCGGCGCTATCATCATGTACG 9180
            GGTGGGACATGTGGTGGGACAGGGGAACACTGTACACATGGCCGCGATAGTAGTACATGC
9181  GCATCCCTAGGTGTGTGATCGGCGAGAACGTGAACTTCAAGTCCAAGGGCGAGAAGTACC 9240
      CGTAGGGATCCACACAGTAGCCGCTCTTGCACTTGAAGTTCAGGTTCCCGCTCTTCATGG

9241  TCCAAACCAGGGGCCACCAGGTGGTCGTTGTTGACCATGAGAGCTGTAAGAAGCTGATGA 9300
      AGGTTTGGTCCCCGGTGCTCCACCAGCAACAACTGCTACTCTCGACATTCTTCGACTACT

NotI(9356)
                                                           |
                                                           CciNI
                                                           |
9301  AGCAGTTCATCGACGAGAGGCCTCAGGACTGGTTCGAGGATATCGGCGAGTAAGCGGCCG 9360
      TCGTCAAGTAGCTGCTCTCCGGAGTCCTGACCAAGCTCCTATAGCCGCTCATTCGCCGGC

U3 Region(9405,9854)>>>
                                                           |
9361  CAGATAAAATAAAAGATTTTATTTAGTCTCCAGAAAAAGGGGGGAATGAAAGACCCCACC 9420
      GTCTATTTTATTTTCTAAAATAAATCAGAGGTCTTTTTCCCCCCTTACTTTCTGGGGTGG
```

FIGURE 1D-18

```
                              BmtI
                               |
                            NheI
                             | |
                         AsuNHI      5_LTR2 other(9447,9998)>>>>
                             | |      |
9421  TGTAGGTTTGGCAAGCTAGCTTAAGTAACGCCATTTTGCAAGGCATGGAAAAATACATAA  9480
      ACATCCAAACCGTTCGATCGAATTCATTGCGGTAAAACGTTCCGTACCTTTTTATGTATT 9481  CTGAGAATAGAGAAGTTCAGATCAAGGTCAGGAACAGATGGAACAGCTGAATATGGGCCA  9540
      GACTCTTATCTCTTCAAGTCTAGTTCCAGTCCTTGTCTACCTTGTCGACTTATACCCGGT 9541  AACAGGATATCTGTGGTAAGCAGTTCCTGCCCCGGCTCAGGGCCAAGAACAGATGGAACA  9600
      TTGTCCTATAGACACCATTCGTCAAGGACGGGGCCGAGTCCCGGTTCTTGTCTACCTTGT 9601  GCTGAATATGGGCCAAACAGGATATCTGTGGTAAGCAGTTCCTGCCCCGGCTCAGGGCCA  9660
      CGACTTATACCCGGTTTGTCCTATAGACACCATTCGTCAAGGACGGGGCCGAGTCCCGGT 9661  AGAACAGATGGTCCCCAGATGCGGTCCAGCCCTCAGCAGTTTCTAGAGAACCATCAGATG  9720
      TCTTGTCTACCAGGGGTCTACGCCAGGTCGGGAGTCGTCAAAGATCTCTTGGTAGTCTAC 9721  TTTCCAGGGTGCCCCAAGGACCTGAAATGACCCTGTGCCTTATTTGAACTAACCAATCAG  9780
      AAAGGTCCCACGGGGTTCCTGGACTTTACTGGGACACGGAATAAACTTGATTGGTTAGTC SacI
                                             |
                                            SstI
                                             |
                           PauI            Psp124BI
                            |                |
                           BsePI           EcoICRI
                            |                | |
                           BssHII           Ecl136II
                            |                | |
9781  TTCGCTTCTCGCTTCTGTTCGCGCGCTTCTGCTCCCCGAGCTCAATAAAAGAGCCCACAA  9840
      AAGCGAAGAGCGAAGACAAGCGCGCGAAGACGAGGGGCTCGAGTTATTTTCTCGGGTGTT R Region(9855,9921)>>>>
                |
9841  CCCCTCACTCGGGGCGCCAGTCCTCCGATTGACTGAGTCGCCCGGGTACCCGTGTATCCA  9900
      GGGGAGTGAGCCCCGCGGTCAGGAGGCTAACTGACTCAGCGGGCCCATGGGCACATAGGT U5 Region(9922,9998)>>>>
              |
9901  ATAAACCCTCTTGCAGTTGCATCCGACTTGTGGTCTCGCTGTTCCTTGGGAGGGTCTCCT  9960
      TATTTGGGAGAACGTCAACGTAGGCTGAACACCAGAGCGACAAGGAACCCTCCCAGAGGA 9961  CTGAGTGATTGACTACCCGTCAGCGGGGGTCTTTCATTACATGTGAGCAAAAGGCCAGCA 10020
      GACTCACTAACTGATGGGCAGTCGCCCCCAGAAAGTAATGTACACTCGTTTTCCGGTCGT
```

FIGURE 1D-19 pBR322 origin(10045,10664)<<<

10021 AAAGGCCAGGAACCGTAAAAAGGCCGCGTTGCTGGCGTTTTTCCATAGGCTCCGCCCCC 10080
      TTTCCGGTCCTTGGCATTTTTCCGGCGCAACGACCGCAAAAAGGTATCCGAGGCGGGGG

10081 TGACGAGCATCACAAAAATCGACGCTCAAGTCAGAGGTGGCGAAACCCGACAGGACTATA 10140
      ACTGCTCGTAGTGTTTTTAGCTGCGAGTTCAGTCTCCACCGCTTTGGGCTGTCCTGATAT

10141 AAGATACCAGGCGTTTCCCCCTGGAAGCTCCCTCGTGCGCTCTCCTGTTCCGACCCTGCC 10200
      TTCTATGGTCCGCAAAGGGGGACCTTCGAGGGAGCACGCGAGAGGACAAGGCTGGGACGG

10201 GCTTACCGGATACCTGTCCGCCTTTCTCCCTTCGGGAAGCGTGGCGCTTTCTCAATGCTC 10260
      CGAATGGCCTATGGACAGGCGGAAAGAGGGAAGCCCTTCGCACCGCGAAAGAGTTACGAG

10261 ACGCTGTAGGTATCTCAGTTCGGTGTAGGTCGTTCGCTCCAAGCTGGGCTGTGTGCACGA 10320
      TGCGACATCCATAGAGTCAAGCCACATCCAGCAAGCGAGGTTCGACCCGACACACGTGCT

10321 ACCCCCCGTTCAGCCCGACCGCTGCGCCTTATCCGGTAACTATCGTCTTGAGTCCAACCC 10380
      TGGGGGGCAAGTCGGGCTGGCGACGCGGAATAGGCCATTGATAGCAGAACTCAGGTTGGG

10381 GGTAAGACACGACTTATCGCCACTGGCAGCAGCCACTGGTAACAGGATTAGCAGAGCGAG 10440
      CCATTCTGTGCTGAATAGCGGTGACCGTCGTCGGTGACCATTGTCCTAATCGTCTCGCTC

10441 GTATGTAGGCGGTGCTACAGAGTTCTTGAAGTGGTGGCCTAACTACGGCTACACTAGAAG 10500
      CATACATCCGCCACGATGTCTCAAGAACTTCACCACCGGATTGATGCCGATGTGATCTTC

10501 GACAGTATTTGGTATCTGCGCTCTGCTGAAGCCAGTTACCTTCGGAAAAAGAGTTGGTAG 10560
      CTGTCATAAACCATAGACGCGAGACGACTTCGGTCAATGGAAGCCTTTTTCTCAACCATC

10561 CTCTTGATCCGGCAAACAAACCACCGCTGGTAGCGGTGGTTTTTTTGTTTGCAAGCAGCA 10620
      GAGAACTAGGCCGTTTGTTTGGTGGCGACCATCGCCACCAAAAAAACAAACGTTCGTCGT

10621 GATTACGCGCAGAAAAAAAGGATCTCAAGAAGATCCTTTGATCTTTTCTACGGGGTCTGA 10680
      CTAATGCGCGTCTTTTTTTCCTAGAGTTCTTCTAGGAAACTAGAAAAGATGCCCCAGACT

10681 CGCTCAGTGGAACGAAAACTCACGTTAAGGGATTTTGGTCATGAGATTATCAAAAAGGAT 10740
      GCGAGTCACCTTGCTTTTGAGTGCAATTCCCTAAAACCAGTACTCTAATAGTTTTTCCTA

10741 CTTCACCTAGATCCTTTTAAATTAAAAATGAAGTTTTAAATCAATCTAAAGTATATATGA 10800
      GAAGTGGATCTAGGAAAATTTAATTTTTACTTCAAAATTTAGTTAGATTTCATATATACT

FIGURE 1D-20

```
                      amp marker(10819,11679)<<<
                      |
10801 GTAAACTTGGTCTGACAGTTACCAATGCTTAATCAGTGAGGCACCTATCTCAGCGATCTG 10860
      CATTTGAACCAGACTGTCAATGGTTACGAATTAGTCACTCCGTGGATAGAGTCGCTAGAC 10861 TCTATTTCGTTCATCCATAGTTGCCTGACTCCCCGTCGTGTAGATAACTACGATACGGGA 10920
      AGATAAAGCAAGTAGGTATCAACGGACTGAGGGGCAGCACATCTATTGATGCTATGCCCT 10921 GGGCTTACCATCTGGCCCCAGTGCTGCAATGATACCGCGAGACCCACGCTCACCGGCTCC 10980
      CCCGAATGGTAGACCGGGGTCACGACGTTACTATGGCGCTCTGGGTGCGAGTGGCCGAGG 10981 AGATTTATCAGCAATAAACCAGCCAGCCGGAAGGGCCGAGCGCAGAAGTGGTCCTGCAAC 11040
      TCTAAATAGTCGTTATTTGGTCGGTCGGCCTTCCCGGCTCGCGTCTTCACCAGGACGTTG 11041 TTTATCCGCCTCCATCCAGTCTATTAATTGTTGCCGGGAAGCTAGAGTAAGTAGTTCGCC 11100
      AAATAGGCGGAGGTAGGTCAGATAATTAACAACGGCCCTTCGATCTCATTCATCAAGCGG 11101 AGTTAATAGTTTGCGCAACGTTGTTGCCATTGCTGCAGGCATCGTGGTGTCACGCTCGTC 11160
      TCAATTATCAAACGCGTTGCAACAACGGTAACGACGTCCGTAGCACCACAGTGCGAGCAG 11161 GTTTGGTATGGCTTCATTCAGCTCCGGTTCCCAACGATCAAGGCGAGTTACATGATCCCC 11220
      CAAACCATACCGAAGTAAGTCGAGGCCAAGGGTTGCTAGTTCCGCTCAATGTACTAGGGG 11221 CATGTTGTGCAAAAAAGCGGTTAGCTCCTTCGGTCCTCCGATCGTTGTCAGAAGTAAGTT 11280
      GTACAACACGTTTTTTCGCCAATCGAGGAAGCCAGGAGGCTAGCAACAGTCTTCATTCAA 11281 GGCCGCAGTGTTATCACTCATGGTTATGGCAGCACTGCATAATTCTCTTACTGTCATGCC 11340
      CCGGCGTCACAATAGTGAGTACCAATACCGTCGTGACGTATTAAGAGAATGACAGTACGG 11341 ATCCGTAAGATGCTTTTCTGTGACTGGTGAGTACTCAACCAAGTCATTCTGAGAATAGTG 11400
      TAGGCATTCTACGAAAAGACACTGACCACTCATGAGTTGGTTCAGTAAGACTCTTATCAC 11401 TATGCGGCGACCGAGTTGCTCTTGCCCGGCGTCAACACGGGATAATACCGCGCCACATAG 11460
      ATACGCCGCTGGCTCAACGAGAACGGGCCGCAGTTGTGCCCTATTATGGCGCGGTGTATC 11461 CAGAACTTTAAAAGTGCTCATCATTGGAAAACGTTCTTCGGGGCGAAAACTCTCAAGGAT 11520
      GTCTTGAAATTTTCACGAGTAGTAACCTTTTGCAAGAAGCCCCGCTTTTGAGAGTTCCTA 11521 CTTACCGCTGTTGAGATCCAGTTCGATGTAACCCACTCGTGCACCCAACTGATCTTCAGC 11580
      GAATGGCGACAACTCTAGGTCAAGCTACATTGGGTGAGCACGTGGGTTGACTAGAAGTCG 11581 ATCTTTTACTTTCACCAGCGTTTCTGGGTGAGCAAAAACAGGAAGGCAAAATGCCGCAAA 11640
      TAGAAAATGAAAGTGGTCGCAAAGACCCACTCGTTTTGTCCTTCCGTTTTACGGCGTTT 11641 AAAGGGAATAAGGGCGACACGGAAATGTTGAATACTCATACTCTTCCTTTTTCAATATTA 11700
      TTTCCCTTATTCCCGCTGTGCCTTTACAACTTATGAGTATGAGAAGGAAAAAGTTATAAT
```

FIGURE 1D-21

```
                                            amp prom(11721,11749)<<<
                                            |
11701 TTGAAGCATTTATCAGGGTTATTGTCTCATGAGCGGATACATATTTGAATGTATTTAGAA 11760
      AACTTCGTAAATAGTCCCAATAACAGAGTACTCGCCTATGTATAAACTTACATAAATCTT 11761 AAATAAACAAATAGGGGTTCCGCGCACATTTCCCCGAAAAGTGCCACCTGACGTCTAAGA 11820
      TTTATTTGTTTATCCCCAAGGCGCGTGTAAAGGGGCTTTTCACGGTGGACTGCAGATTCT 11821 AACCATTATTATCATGACATTAACCTATAAAAATAGGCGTATCACGAGGCCCTTTCGTCT 11880
      TTGGTAATAATAGTACTGTAATTGGATATTTTTATCCGCATAGTGCTCCGGGAAAGCAGA

11881 TCAAGAATTCAT 11892
      AGTTCTTAAGTA
```

FIGURE 1D-22

1. Separate synthesis of CDopt and UPRT genes with PSI1/Not1 sites

2. Digest with PSI1 and perform blunt end ligation

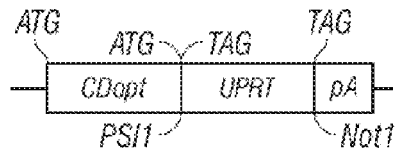

3. Deletion of CDopt gene STOP and UPRT START codon by site directed mutagenesis

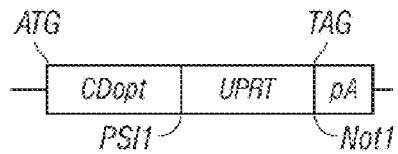

4. CDopt-UPRT gene size: 1.3 kb

FIGURE 2A

1. Synthesis of CDopt-LINKER-UPRT: Site directed mutagenesis insertion of linker 2. CDopt-Linker-UPRT gene size: 1.36 kb 1. Separate synthesis of CDopt gene and OPRT domain with PSI1/Not1 sites 2. Digest with PSI1 and perform blunt end ligation 3. Deletion of CDopt gene STOP and OPRT START codon by site directed mutagenesis 4. CDopt-OPRT gene size: 1.3 kb 1. Synthesis of CDopt-LINKER-OPRT: Site directed mutagenesis insertion of linker 2. CD-OPRT gene size: 1.33 kb 1 - U87 + AC3-yCD2 (V)
2 - U87 + ACE-yCD (V)
3 - U87 (uninfected)
4 - Molecular Weight Standards

SEQUENCE LISTING

<160> NUMBER OF SEQ ID NOS: 54

<210> SEQ ID NO 1
<211> LENGTH: 477
<212> TYPE: DNA
<213> ORGANISM: Saccharomyces cerevisiae
<220> FEATURE:
<221> NAME/KEY: CDS
<222> LOCATION: (1)..(477)

<400> SEQUENCE: 1

```
atg gtg aca ggg gga atg gca agc aag tgg gat cag aag ggt atg gac      48
Met Val Thr Gly Gly Met Ala Ser Lys Trp Asp Gln Lys Gly Met Asp
1               5                   10                  15 att gcc tat gag gag gcg gcc tta ggt tac aaa gag ggt ggt gtt cct      96
Ile Ala Tyr Glu Glu Ala Ala Leu Gly Tyr Lys Glu Gly Gly Val Pro
                20                  25                  30 att ggc gga tgt ctt atc aat aac aaa gac gga agt gtt ctc ggt cgt     144
Ile Gly Gly Cys Leu Ile Asn Asn Lys Asp Gly Ser Val Leu Gly Arg
            35                  40                  45 ggt cac aac atg aga ttt caa aag gga tcc gcc aca cta cat ggt gag     192
Gly His Asn Met Arg Phe Gln Lys Gly Ser Ala Thr Leu His Gly Glu
        50                  55                  60 atc tcc act ttg gaa aac tgt ggg aga tta gag ggc aaa gtg tac aaa     240
Ile Ser Thr Leu Glu Asn Cys Gly Arg Leu Glu Gly Lys Val Tyr Lys
65                  70                  75                  80 gat acc act ttg tat acg acg ctg tct cca tgc gac atg tgt aca ggt     288
Asp Thr Thr Leu Tyr Thr Thr Leu Ser Pro Cys Asp Met Cys Thr Gly
                85                  90                  95 gcc atc atc atg tat ggt att cca cgc tgt gtt gtc ggt gag aac gtt     336
Ala Ile Ile Met Tyr Gly Ile Pro Arg Cys Val Val Gly Glu Asn Val
            100                 105                 110 aat ttc aaa agt aag ggc gag aaa tat tta caa act aga ggt cac gag     384
Asn Phe Lys Ser Lys Gly Glu Lys Tyr Leu Gln Thr Arg Gly His Glu
        115                 120                 125 gtt gtt gtt gtt gac gat gag agg tgt aaa aag atc atg aaa caa ttt     432
Val Val Val Val Asp Asp Glu Arg Cys Lys Lys Ile Met Lys Gln Phe
    130                 135                 140 atc gat gaa aga cct cag gat tgg ttt gaa gat att ggt gag tag         477
Ile Asp Glu Arg Pro Gln Asp Trp Phe Glu Asp Ile Gly Glu
145                 150                 155
```

<210> SEQ ID NO 2
<211> LENGTH: 158
<212> TYPE: PRT
<213> ORGANISM: Saccharomyces cerevisiae

<400> SEQUENCE: 2

```
Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
                20                  25                  30

Ile Gly Gly Cys Leu Ile Asn Asn Lys Asp Gly Ser Val Leu Gly Arg
            35                  40                  45

Gly His Asn Met Arg Phe Gln Lys Gly Ser Ala Thr Leu His Gly Glu
        50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95
```

```
Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155

<210> SEQ ID NO 3
<211> LENGTH: 477
<212> TYPE: DNA
<213> ORGANISM: Artificial Sequence
<220> FEATURE:
<223> OTHER INFORMATION: Engineered cytosine deaminase
<220> FEATURE:
<221> NAME/KEY: CDS
<222> LOCATION: (1)..(477)

<400> SEQUENCE: 3 atg gtg aca ggg gga atg gca agc aag tgg gat cag aag ggt atg gac    48
Met Val Thr Gly Gly Met Ala Ser Lys Trp Asp Gln Lys Gly Met Asp
1               5                   10                  15 att gcc tat gag gag gcg tta tta ggt tac aaa gag ggt ggt gtt cct    96
Ile Ala Tyr Glu Glu Ala Leu Leu Gly Tyr Lys Glu Gly Gly Val Pro
            20                  25                  30 att ggc gga tgt ctt atc aat aac aaa gac gga agt gtt ctc ggt cgt   144
Ile Gly Gly Cys Leu Ile Asn Asn Lys Asp Gly Ser Val Leu Gly Arg
        35                  40                  45 ggt cac aac atg aga ttt caa aag gga tcc gcc aca cta cat ggt gag   192
Gly His Asn Met Arg Phe Gln Lys Gly Ser Ala Thr Leu His Gly Glu
    50                  55                  60 atc tcc act ttg gaa aac tgt ggg aga tta gag ggc aaa gtg tac aaa   240
Ile Ser Thr Leu Glu Asn Cys Gly Arg Leu Glu Gly Lys Val Tyr Lys
65                  70                  75                  80 gat acc act ttg tat acg acg ctg tct cca tgc gac atg tgt aca ggt   288
Asp Thr Thr Leu Tyr Thr Thr Leu Ser Pro Cys Asp Met Cys Thr Gly
                85                  90                  95 gcc atc atc atg tat ggt att cca cgc tgt gtc atc ggt gag aac gtt   336
Ala Ile Ile Met Tyr Gly Ile Pro Arg Cys Val Ile Gly Glu Asn Val
            100                 105                 110 aat ttc aaa agt aag ggc gag aaa tat tta caa act aga ggt cac gag   384
Asn Phe Lys Ser Lys Gly Glu Lys Tyr Leu Gln Thr Arg Gly His Glu
        115                 120                 125 gtt gtt gtt gtt gac gat gag agg tgt aaa aag tta atg aaa caa ttt   432
Val Val Val Val Asp Asp Glu Arg Cys Lys Lys Leu Met Lys Gln Phe
    130                 135                 140 atc gat gaa aga cct cag gat tgg ttt gaa gat att ggt gag tag       477
Ile Asp Glu Arg Pro Gln Asp Trp Phe Glu Asp Ile Gly Glu
145                 150                 155

<210> SEQ ID NO 4
<211> LENGTH: 158
<212> TYPE: PRT
<213> ORGANISM: Artificial Sequence
<220> FEATURE:
<223> OTHER INFORMATION: Synthetic Construct

<400> SEQUENCE: 4

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
```

```
                20                  25                  30
Ile Gly Gly Cys Leu Ile Asn Asn Lys Asp Gly Ser Val Leu Gly Arg
            35                  40                  45

Gly His Asn Met Arg Phe Gln Lys Gly Ser Ala Thr Leu His Gly Glu
        50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu
145                 150                 155

<210> SEQ ID NO 5
<211> LENGTH: 480
<212> TYPE: DNA
<213> ORGANISM: Artificial Sequence
<220> FEATURE:
<223> OTHER INFORMATION: Human codon optimized cytosine deaminase
<220> FEATURE:
<221> NAME/KEY: CDS
<222> LOCATION: (1)..(480)

<400> SEQUENCE: 5 atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15 atc gct tac gag gag gcc gca ctg ggc tac aag gag ggc ggc gtg cct       96
Ile Ala Tyr Glu Glu Ala Ala Leu Gly Tyr Lys Glu Gly Gly Val Pro
                20                  25                  30 atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
            35                  40                  45 ggc cac aac atg agg ttc cag aag ggc tcc gcc acc ctg cac ggc gag      192
Gly His Asn Met Arg Phe Gln Lys Gly Ser Ala Thr Leu His Gly Glu
        50                  55                  60 atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95 gct atc atc atg tac ggc atc cct agg tgt gtg gtc ggc gag aac gtg      336
Ala Ile Ile Met Tyr Gly Ile Pro Arg Cys Val Val Gly Glu Asn Val
            100                 105                 110 aac ttc aag tcc aag ggc gag aag tac ctg caa acc agg ggc cac gag      384
Asn Phe Lys Ser Lys Gly Glu Lys Tyr Leu Gln Thr Arg Gly His Glu
        115                 120                 125 gtg gtg gtt gtt gac gat gag agg tgt aag aag atc atg aag cag ttc      432
Val Val Val Val Asp Asp Glu Arg Cys Lys Lys Ile Met Lys Gln Phe
    130                 135                 140 atc gac gag agg cct cag gac tgg ttc gag gat atc ggc gag tga taa      480
Ile Asp Glu Arg Pro Gln Asp Trp Phe Glu Asp Ile Gly Glu
145                 150                 155
```

<210> SEQ ID NO 6
<211> LENGTH: 158
<212> TYPE: PRT
<213> ORGANISM: Artificial Sequence
<220> FEATURE:
<223> OTHER INFORMATION: Synthetic Construct

<400> SEQUENCE: 6

```
Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155
```

<210> SEQ ID NO 7
<211> LENGTH: 756
<212> TYPE: DNA
<213> ORGANISM: Saccharomyces cerevisiae
<220> FEATURE:
<221> NAME/KEY: CDS
<222> LOCATION: (1)..(756)

<400> SEQUENCE: 7

```
atg aac ccg tta ttc ttt ttg gct tct cca ttc ttg tac ctt aca tat     48
Met Asn Pro Leu Phe Phe Leu Ala Ser Pro Phe Leu Tyr Leu Thr Tyr
1               5                   10                  15 ctt ata tat tat cca aac aaa ggg tct ttc gtt agc aaa cct aga aat     96
Leu Ile Tyr Tyr Pro Asn Lys Gly Ser Phe Val Ser Lys Pro Arg Asn
            20                  25                  30 ctg caa aaa atg tct tcg gaa cca ttt aag aac gtc tac ttg cta cct    144
Leu Gln Lys Met Ser Ser Glu Pro Phe Lys Asn Val Tyr Leu Leu Pro
        35                  40                  45 caa aca aac caa ttg ctg ggt ttg tac acc atc atc aga aat aag aat    192
Gln Thr Asn Gln Leu Leu Gly Leu Tyr Thr Ile Ile Arg Asn Lys Asn
    50                  55                  60 aca act aga cct gat ttc att ttc tac tcc gat aga atc atc aga ttg    240
Thr Thr Arg Pro Asp Phe Ile Phe Tyr Ser Asp Arg Ile Ile Arg Leu
65                  70                  75                  80 ttg gtt gaa gaa ggt ttg aac cat cta cct gtg caa aag caa att gtg    288
Leu Val Glu Glu Gly Leu Asn His Leu Pro Val Gln Lys Gln Ile Val
                85                  90                  95 gaa act gac acc aac gaa aac ttc gaa ggt gtc tca ttc atg ggt aaa    336
Glu Thr Asp Thr Asn Glu Asn Phe Glu Gly Val Ser Phe Met Gly Lys
            100                 105                 110 atc tgt ggt gtt tcc att gtc aga gct ggt gaa tcg atg gag caa gga    384
Ile Cys Gly Val Ser Ile Val Arg Ala Gly Glu Ser Met Glu Gln Gly
```

```
                        115                      120                      125
tta aga gac tgt tgt agg tct gtg cgt atc ggt aaa att tta att caa       432
Leu Arg Asp Cys Cys Arg Ser Val Arg Ile Gly Lys Ile Leu Ile Gln
    130                     135                     140 agg gac gag gag act gct tta cca aag tta ttc tac gaa aaa tta cca       480
Arg Asp Glu Glu Thr Ala Leu Pro Lys Leu Phe Tyr Glu Lys Leu Pro
145                     150                     155                     160 gag gat ata tct gaa agg tat gtc ttc cta tta gac cca atg ctg gcc       528
Glu Asp Ile Ser Glu Arg Tyr Val Phe Leu Leu Asp Pro Met Leu Ala
                165                     170                     175 acc ggt ggt agt gct atc atg gct aca gaa gtc ttg att aag aga ggt       576
Thr Gly Gly Ser Ala Ile Met Ala Thr Glu Val Leu Ile Lys Arg Gly
            180                     185                     190 gtt aag cca gag aga att tac ttc tta aac cta atc tgt agt aag gaa       624
Val Lys Pro Glu Arg Ile Tyr Phe Leu Asn Leu Ile Cys Ser Lys Glu
        195                     200                     205 ggg att gaa aaa tac cat gcc gcc ttc cca gag gtc aga att gtt act       672
Gly Ile Glu Lys Tyr His Ala Ala Phe Pro Glu Val Arg Ile Val Thr
    210                     215                     220 ggt gcc ctc gac aga ggt cta gat gaa aac aag tat cta gtt cca ggg       720
Gly Ala Leu Asp Arg Gly Leu Asp Glu Asn Lys Tyr Leu Val Pro Gly
225                     230                     235                     240 ttg ggt gac ttt ggt gac aga tac tac tgt gtt taa                       756
Leu Gly Asp Phe Gly Asp Arg Tyr Tyr Cys Val
                245                     250

<210> SEQ ID NO 8
<211> LENGTH: 251
<212> TYPE: PRT
<213> ORGANISM: Saccharomyces cerevisiae

<400> SEQUENCE: 8

Met Asn Pro Leu Phe Phe Leu Ala Ser Pro Phe Leu Tyr Leu Thr Tyr
1               5                   10                  15

Leu Ile Tyr Tyr Pro Asn Lys Gly Ser Phe Val Ser Lys Pro Arg Asn
            20                  25                  30

Leu Gln Lys Met Ser Ser Glu Pro Phe Lys Asn Val Tyr Leu Leu Pro
        35                  40                  45

Gln Thr Asn Gln Leu Leu Gly Leu Tyr Thr Ile Ile Arg Asn Lys Asn
    50                  55                  60

Thr Thr Arg Pro Asp Phe Ile Phe Tyr Ser Asp Arg Ile Ile Arg Leu
65                  70                  75                  80

Leu Val Glu Glu Gly Leu Asn His Leu Pro Val Gln Lys Gln Ile Val
                85                  90                  95

Glu Thr Asp Thr Asn Glu Asn Phe Glu Gly Val Ser Phe Met Gly Lys
            100                 105                 110

Ile Cys Gly Val Ser Ile Val Arg Ala Gly Glu Ser Met Glu Gln Gly
        115                 120                 125

Leu Arg Asp Cys Cys Arg Ser Val Arg Ile Gly Lys Ile Leu Ile Gln
    130                 135                 140

Arg Asp Glu Glu Thr Ala Leu Pro Lys Leu Phe Tyr Glu Lys Leu Pro
145                 150                 155                 160

Glu Asp Ile Ser Glu Arg Tyr Val Phe Leu Leu Asp Pro Met Leu Ala
                165                 170                 175

Thr Gly Gly Ser Ala Ile Met Ala Thr Glu Val Leu Ile Lys Arg Gly
            180                 185                 190

Val Lys Pro Glu Arg Ile Tyr Phe Leu Asn Leu Ile Cys Ser Lys Glu
        195                 200                 205
```

-continued

```
Gly Ile Glu Lys Tyr His Ala Ala Phe Pro Glu Val Arg Ile Val Thr
    210                 215                 220
Gly Ala Leu Asp Arg Gly Leu Asp Glu Asn Lys Tyr Leu Val Pro Gly
225                 230                 235                 240
Leu Gly Asp Phe Gly Asp Arg Tyr Tyr Cys Val
                245                 250

<210> SEQ ID NO 9
<211> LENGTH: 1443
<212> TYPE: DNA
<213> ORGANISM: homo sapiens
<220> FEATURE:
<221> NAME/KEY: CDS
<222> LOCATION: (1)..(1443)

<400> SEQUENCE: 9 atg gct gtt gct cgt gct gct ctt ggt cct ctt gtt act ggt ctt tat    48
Met Ala Val Ala Arg Ala Ala Leu Gly Pro Leu Val Thr Gly Leu Tyr
1               5                   10                  15 gat gtt caa gct ttt aaa ttt ggt gat ttt gtt ctt aaa tct ggt ctt    96
Asp Val Gln Ala Phe Lys Phe Gly Asp Phe Val Leu Lys Ser Gly Leu
            20                  25                  30 tct tct cct att tat att gat ctt cgt ggt att gtt tct cgt cct cgt   144
Ser Ser Pro Ile Tyr Ile Asp Leu Arg Gly Ile Val Ser Arg Pro Arg
        35                  40                  45 ctt ctt tct caa gtt gct gat att ctt ttt caa act gct caa aat gct   192
Leu Leu Ser Gln Val Ala Asp Ile Leu Phe Gln Thr Ala Gln Asn Ala
    50                  55                  60 ggt att tct ttt gat act gtt tgt ggt gtt cct tat act gct ctt cct   240
Gly Ile Ser Phe Asp Thr Val Cys Gly Val Pro Tyr Thr Ala Leu Pro
65                  70                  75                  80 ctt gct act gtt att tgt tct act aat caa att cct atg ctt att cgt   288
Leu Ala Thr Val Ile Cys Ser Thr Asn Gln Ile Pro Met Leu Ile Arg
                85                  90                  95 cgt aaa gaa act aaa gat tat ggt act aaa cgt ctt gtt gaa ggt act   336
Arg Lys Glu Thr Lys Asp Tyr Gly Thr Lys Arg Leu Val Glu Gly Thr
            100                 105                 110 att aat cct ggt gaa act tgt ctt att att gaa gat gtt gtt act tct   384
Ile Asn Pro Gly Glu Thr Cys Leu Ile Ile Glu Asp Val Val Thr Ser
        115                 120                 125 ggt tct tct gtt ctt gaa act gtt gaa gtt ctt caa aaa gaa ggt ctt   432
Gly Ser Ser Val Leu Glu Thr Val Glu Val Leu Gln Lys Glu Gly Leu
    130                 135                 140 aaa gtt act gat gct att gtt ctt ctt gat cgt gaa caa ggt ggt aaa   480
Lys Val Thr Asp Ala Ile Val Leu Leu Asp Arg Glu Gln Gly Gly Lys
145                 150                 155                 160 gat aaa ctt caa gct cat ggt att cgt ctt cat tct gtt tgt act ctt   528
Asp Lys Leu Gln Ala His Gly Ile Arg Leu His Ser Val Cys Thr Leu
                165                 170                 175 tct aaa atg ctt gaa att ctt gaa caa caa aaa aaa gtt gat gct gaa   576
Ser Lys Met Leu Glu Ile Leu Glu Gln Gln Lys Lys Val Asp Ala Glu
            180                 185                 190 act gtt ggt cgt gtt aaa cgt ttt att caa gaa aat gtt ttt gtt gct   624
Thr Val Gly Arg Val Lys Arg Phe Ile Gln Glu Asn Val Phe Val Ala
        195                 200                 205 gct aat cat aat ggt tct cct ctt tct att aaa gaa gct cct aaa gaa   672
Ala Asn His Asn Gly Ser Pro Leu Ser Ile Lys Glu Ala Pro Lys Glu
    210                 215                 220 ctt tct ttt ggt gct cgt gct gaa ctt cct cgt att cat cct gtt gct   720
Leu Ser Phe Gly Ala Arg Ala Glu Leu Pro Arg Ile His Pro Val Ala
225                 230                 235                 240
```

```
tct aaa ctt ctt cgt ctt atg caa aaa aaa gaa act aat ctt tgt ctt    768
Ser Lys Leu Leu Arg Leu Met Gln Lys Lys Glu Thr Asn Leu Cys Leu
            245                 250                 255 tct gct gat gtt tct ctt gct cgt gaa ctt ctt caa ctt gct gat gct    816
Ser Ala Asp Val Ser Leu Ala Arg Glu Leu Leu Gln Leu Ala Asp Ala
        260                 265                 270 ctt ggt cct tct att tgt atg ctt aaa act cat gtt gat att ctt aat    864
Leu Gly Pro Ser Ile Cys Met Leu Lys Thr His Val Asp Ile Leu Asn
    275                 280                 285 gat ttt act ctt gat gtt atg aaa gaa ctt att act ctt gct aaa tgt    912
Asp Phe Thr Leu Asp Val Met Lys Glu Leu Ile Thr Leu Ala Lys Cys
290                 295                 300 cat gaa ttt ctt att ttt gaa gat cgt aaa ttt gct gat att ggt aat    960
His Glu Phe Leu Ile Phe Glu Asp Arg Lys Phe Ala Asp Ile Gly Asn
305                 310                 315                 320 act gtt aaa aaa caa tat gaa ggt ggt att ttt aaa att gct tct tgg   1008
Thr Val Lys Lys Gln Tyr Glu Gly Gly Ile Phe Lys Ile Ala Ser Trp
                325                 330                 335 gct gat ctt gtt aat gct cat gtt gtt cct ggt tct ggt gtt gtt aaa   1056
Ala Asp Leu Val Asn Ala His Val Val Pro Gly Ser Gly Val Val Lys
            340                 345                 350 ggt ctt caa gaa gtt ggt ctt cct ctt cat cgt ggt tgt ctt ctt att   1104
Gly Leu Gln Glu Val Gly Leu Pro Leu His Arg Gly Cys Leu Leu Ile
        355                 360                 365 gct gaa atg tct tct act ggt tct ctt gct act ggt gat tat act cgt   1152
Ala Glu Met Ser Ser Thr Gly Ser Leu Ala Thr Gly Asp Tyr Thr Arg
    370                 375                 380 gct gct gtt cgt atg gct gaa gaa cat tct gaa ttt gtt gtt ggt ttt   1200
Ala Ala Val Arg Met Ala Glu Glu His Ser Glu Phe Val Val Gly Phe
385                 390                 395                 400 att tct ggt tct cgt gtt tct atg aaa cct gaa ttt ctt cat ctt act   1248
Ile Ser Gly Ser Arg Val Ser Met Lys Pro Glu Phe Leu His Leu Thr
                405                 410                 415 cct ggt gtt caa ctt gaa gct ggt ggt gat aat ctt ggt caa caa tat   1296
Pro Gly Val Gln Leu Glu Ala Gly Gly Asp Asn Leu Gly Gln Gln Tyr
            420                 425                 430 aat tct cct caa gaa gtt att ggt aaa cgt ggt tct gat att att att   1344
Asn Ser Pro Gln Glu Val Ile Gly Lys Arg Gly Ser Asp Ile Ile Ile
        435                 440                 445 gtt ggt cgt ggt att att tct gct gct gat cgt ctt gaa gct gct gaa   1392
Val Gly Arg Gly Ile Ile Ser Ala Ala Asp Arg Leu Glu Ala Ala Glu
    450                 455                 460 atg tat cgt aaa gct gct tgg gaa gct tat ctt tct cgt ctt ggt gtt   1440
Met Tyr Arg Lys Ala Ala Trp Glu Ala Tyr Leu Ser Arg Leu Gly Val
465                 470                 475                 480 taa                                                                1443

<210> SEQ ID NO 10
<211> LENGTH: 480
<212> TYPE: PRT
<213> ORGANISM: homo sapiens

<400> SEQUENCE: 10

Met Ala Val Ala Arg Ala Ala Leu Gly Pro Leu Val Thr Gly Leu Tyr
1               5                   10                  15

Asp Val Gln Ala Phe Lys Phe Gly Asp Phe Val Leu Lys Ser Gly Leu
            20                  25                  30

Ser Ser Pro Ile Tyr Ile Asp Leu Arg Gly Ile Val Ser Arg Pro Arg
        35                  40                  45
```

```
Leu Leu Ser Gln Val Ala Asp Ile Leu Phe Gln Thr Ala Gln Asn Ala
 50                  55                  60

Gly Ile Ser Phe Asp Thr Val Cys Gly Val Pro Tyr Thr Ala Leu Pro
 65                  70                  75                  80

Leu Ala Thr Val Ile Cys Ser Thr Asn Gln Ile Pro Met Leu Ile Arg
                 85                  90                  95

Arg Lys Glu Thr Lys Asp Tyr Gly Thr Lys Arg Leu Val Glu Gly Thr
            100                 105                 110

Ile Asn Pro Gly Glu Thr Cys Leu Ile Glu Asp Val Val Thr Ser
            115                 120                 125

Gly Ser Ser Val Leu Glu Thr Val Glu Val Leu Gln Lys Glu Gly Leu
        130                 135                 140

Lys Val Thr Asp Ala Ile Val Leu Leu Asp Arg Glu Gln Gly Gly Lys
145                 150                 155                 160

Asp Lys Leu Gln Ala His Gly Ile Arg Leu His Ser Val Cys Thr Leu
                165                 170                 175

Ser Lys Met Leu Glu Ile Leu Glu Gln Gln Lys Lys Val Asp Ala Glu
            180                 185                 190

Thr Val Gly Arg Val Lys Arg Phe Ile Gln Glu Asn Val Phe Val Ala
            195                 200                 205

Ala Asn His Asn Gly Ser Pro Leu Ser Ile Lys Glu Ala Pro Lys Glu
210                 215                 220

Leu Ser Phe Gly Ala Arg Ala Glu Leu Pro Arg Ile His Pro Val Ala
225                 230                 235                 240

Ser Lys Leu Leu Arg Leu Met Gln Lys Lys Thr Asn Leu Cys Leu
            245                 250                 255

Ser Ala Asp Val Ser Leu Ala Arg Glu Leu Leu Gln Leu Ala Asp Ala
            260                 265                 270

Leu Gly Pro Ser Ile Cys Met Leu Lys Thr His Val Asp Ile Leu Asn
            275                 280                 285

Asp Phe Thr Leu Asp Val Met Lys Glu Leu Ile Thr Leu Ala Lys Cys
            290                 295                 300

His Glu Phe Leu Ile Phe Glu Asp Arg Lys Phe Ala Asp Ile Gly Asn
305                 310                 315                 320

Thr Val Lys Lys Gln Tyr Glu Gly Gly Ile Phe Lys Ile Ala Ser Trp
                325                 330                 335

Ala Asp Leu Val Asn Ala His Val Val Pro Gly Ser Gly Val Val Lys
            340                 345                 350

Gly Leu Gln Glu Val Gly Leu Pro Leu His Arg Gly Cys Leu Leu Ile
            355                 360                 365

Ala Glu Met Ser Ser Thr Gly Ser Leu Ala Thr Gly Asp Tyr Thr Arg
            370                 375                 380

Ala Ala Val Arg Met Ala Glu Glu His Ser Glu Phe Val Val Gly Phe
385                 390                 395                 400

Ile Ser Gly Ser Arg Val Ser Met Lys Pro Glu Phe Leu His Leu Thr
                405                 410                 415

Pro Gly Val Gln Leu Glu Ala Gly Gly Asp Asn Leu Gly Gln Gln Tyr
            420                 425                 430

Asn Ser Pro Gln Glu Val Ile Gly Lys Arg Gly Ser Asp Ile Ile Ile
            435                 440                 445

Val Gly Arg Gly Ile Ile Ser Ala Ala Asp Arg Leu Glu Ala Ala Glu
        450                 455                 460

Met Tyr Arg Lys Ala Ala Trp Glu Ala Tyr Leu Ser Arg Leu Gly Val
465                 470                 475                 480
```

<210> SEQ ID NO 11
<211> LENGTH: 1227
<212> TYPE: DNA
<213> ORGANISM: Artificial Sequence
<220> FEATURE:
<223> OTHER INFORMATION: Fusion construct CDopt-UPRT
<220> FEATURE:
<221> NAME/KEY: CDS
<222> LOCATION: (1)..(1227)

<400> SEQUENCE: 11

```
atg gtg acc ggc ggc atg gcc tcc aag tgg gat caa aag ggc atg gat      48
Met Val Thr Gly Gly Met Ala Ser Lys Trp Asp Gln Lys Gly Met Asp
1               5                   10                  15 atc gct tac gag gag gcc ctg ctg ggc tac aag gag ggc ggt gtg cct      96
Ile Ala Tyr Glu Glu Ala Leu Leu Gly Tyr Lys Glu Gly Gly Val Pro
                20                  25                  30 atc ggc ggc tgt ctg atc aac aac aag gac ggc agt gtg ctg ggc agg     144
Ile Gly Gly Cys Leu Ile Asn Asn Lys Asp Gly Ser Val Leu Gly Arg
            35                  40                  45 ggc cac aac atg agg ttc cag aag ggc tcc gcc acc ctg cac ggc gag     192
Gly His Asn Met Arg Phe Gln Lys Gly Ser Ala Thr Leu His Gly Glu
        50                  55                  60 atc tcc acc ctg gag aac tgt ggc agg ctg gag ggc aag gtg tac aag     240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc     288
Asp Thr Thr Leu Tyr Thr Thr Leu Ser Pro Cys Asp Met Cys Thr Gly
                85                  90                  95 gct atc atc atg tac ggc atc cct agg tgt gtg atc ggc gag aac gtg     336
Ala Ile Ile Met Tyr Gly Ile Pro Arg Cys Val Ile Gly Glu Asn Val
                100                 105                 110 aac ttc aag tcc aag ggc gag aag tac ctg caa acc agg ggc cac gag     384
Asn Phe Lys Ser Lys Gly Glu Lys Tyr Leu Gln Thr Arg Gly His Glu
            115                 120                 125 gtg gtg gtt gtt gac gat gag agg tgt aag aag ctg atg aag cag ttc     432
Val Val Val Val Asp Asp Glu Arg Cys Lys Lys Leu Met Lys Gln Phe
        130                 135                 140 atc gac gag agg cct cag gac tgg ttc gag gat atc ggc gag aac ccg     480
Ile Asp Glu Arg Pro Gln Asp Trp Phe Glu Asp Ile Gly Glu Asn Pro
145                 150                 155                 160 tta ttc ttt ttg gct tct cca ttc ttg tac ctt aca tat ctt ata tat     528
Leu Phe Phe Leu Ala Ser Pro Phe Leu Tyr Leu Thr Tyr Leu Ile Tyr
                165                 170                 175 tat cca aac aaa ggg tct ttc gtt agc aaa cct aga aat ctg caa aaa     576
Tyr Pro Asn Lys Gly Ser Phe Val Ser Lys Pro Arg Asn Leu Gln Lys
                180                 185                 190 atg tct tcg gaa cca ttt aag aac gtc tac ttg cta cct caa aca aac     624
Met Ser Ser Glu Pro Phe Lys Asn Val Tyr Leu Leu Pro Gln Thr Asn
            195                 200                 205 caa ttg ctg ggt ttg tac acc atc atc aga aat aag aat aca act aga     672
Gln Leu Leu Gly Leu Tyr Thr Ile Ile Arg Asn Lys Asn Thr Thr Arg
        210                 215                 220 cct gat ttc att ttc tac tcc gat aga atc atc aga ttg ttg gtt gaa     720
Pro Asp Phe Ile Phe Tyr Ser Asp Arg Ile Ile Arg Leu Leu Val Glu
225                 230                 235                 240 gaa ggt ttg aac cat cta cct gtg caa aag caa att gtg gaa act gac     768
Glu Gly Leu Asn His Leu Pro Val Gln Lys Gln Ile Val Glu Thr Asp
                245                 250                 255 acc aac gaa aac ttc gaa ggt gtc tca ttc atg ggt aaa atc tgt ggt     816
Thr Asn Glu Asn Phe Glu Gly Val Ser Phe Met Gly Lys Ile Cys Gly
```

```
                      260                 265                 270
gtt tcc att gtc aga gct ggt gaa tcg atg gag caa gga tta aga gac         864
Val Ser Ile Val Arg Ala Gly Glu Ser Met Glu Gln Gly Leu Arg Asp
        275                 280                 285 tgt tgt agg tct gtg cgt atc ggt aaa att tta att caa agg gac gag         912
Cys Cys Arg Ser Val Arg Ile Gly Lys Ile Leu Ile Gln Arg Asp Glu
    290                 295                 300 gag act gct tta cca aag tta ttc tac gaa aaa tta cca gag gat ata         960
Glu Thr Ala Leu Pro Lys Leu Phe Tyr Glu Lys Leu Pro Glu Asp Ile
305                 310                 315                 320 tct gaa agg tat gtc ttc cta tta gac cca atg ctg gcc acc ggt ggt        1008
Ser Glu Arg Tyr Val Phe Leu Leu Asp Pro Met Leu Ala Thr Gly Gly
                325                 330                 335 agt gct atc atg gct aca gaa gtc ttg att aag aga ggt gtt aag cca        1056
Ser Ala Ile Met Ala Thr Glu Val Leu Ile Lys Arg Gly Val Lys Pro
            340                 345                 350 gag aga att tac ttc tta aac cta atc tgt agt aag gaa ggg att gaa        1104
Glu Arg Ile Tyr Phe Leu Asn Leu Ile Cys Ser Lys Glu Gly Ile Glu
        355                 360                 365 aaa tac cat gcc gcc ttc cca gag gtc aga att gtt act ggt gcc ctc        1152
Lys Tyr His Ala Ala Phe Pro Glu Val Arg Ile Val Thr Gly Ala Leu
    370                 375                 380 gac aga ggt cta gat gaa aac aag tat cta gtt cca ggg ttg ggt gac        1200
Asp Arg Gly Leu Asp Glu Asn Lys Tyr Leu Val Pro Gly Leu Gly Asp
385                 390                 395                 400 ttt ggt gac aga tac tac tgt gtt taa                                    1227
Phe Gly Asp Arg Tyr Tyr Cys Val
                405

<210> SEQ ID NO 12
<211> LENGTH: 408
<212> TYPE: PRT
<213> ORGANISM: Artificial Sequence
<220> FEATURE:
<223> OTHER INFORMATION: Synthetic Construct

<400> SEQUENCE: 12

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Asn Pro
145                 150                 155                 160

Leu Phe Phe Leu Ala Ser Pro Phe Leu Tyr Leu Thr Tyr Leu Ile Tyr
                165                 170                 175
```

```
Tyr Pro Asn Lys Gly Ser Phe Val Ser Lys Pro Arg Asn Leu Gln Lys
                180                 185                 190

Met Ser Ser Glu Pro Phe Lys Asn Val Tyr Leu Leu Pro Gln Thr Asn
            195                 200                 205

Gln Leu Leu Gly Leu Tyr Thr Ile Ile Arg Asn Lys Asn Thr Thr Arg
210                 215                 220

Pro Asp Phe Ile Phe Tyr Ser Asp Arg Ile Ile Arg Leu Leu Val Glu
225                 230                 235                 240

Glu Gly Leu Asn His Leu Pro Val Gln Lys Gln Ile Val Glu Thr Asp
                245                 250                 255

Thr Asn Glu Asn Phe Glu Gly Val Ser Phe Met Gly Lys Ile Cys Gly
            260                 265                 270

Val Ser Ile Val Arg Ala Gly Glu Ser Met Glu Gln Gly Leu Arg Asp
        275                 280                 285

Cys Cys Arg Ser Val Arg Ile Gly Lys Ile Leu Ile Gln Arg Asp Glu
    290                 295                 300

Glu Thr Ala Leu Pro Lys Leu Phe Tyr Glu Lys Leu Pro Glu Asp Ile
305                 310                 315                 320

Ser Glu Arg Tyr Val Phe Leu Leu Asp Pro Met Leu Ala Thr Gly Gly
                325                 330                 335

Ser Ala Ile Met Ala Thr Glu Val Leu Ile Lys Arg Gly Val Lys Pro
            340                 345                 350

Glu Arg Ile Tyr Phe Leu Asn Leu Ile Cys Ser Lys Glu Gly Ile Glu
        355                 360                 365

Lys Tyr His Ala Ala Phe Pro Glu Val Arg Ile Val Thr Gly Ala Leu
    370                 375                 380

Asp Arg Gly Leu Asp Glu Asn Lys Tyr Leu Val Pro Gly Leu Gly Asp
385                 390                 395                 400

Phe Gly Asp Arg Tyr Tyr Cys Val
                405

<210> SEQ ID NO 13
<211> LENGTH: 1287
<212> TYPE: DNA
<213> ORGANISM: Artificial Sequence
<220> FEATURE:
<223> OTHER INFORMATION: Fusion construction - CDopt - linker - UPRT
<220> FEATURE:
<221> NAME/KEY: CDS
<222> LOCATION: (1)..(1287)

<400> SEQUENCE: 13 atg gtg acc ggc ggc atg gcc tcc aag tgg gat caa aag ggc atg gat      48
Met Val Thr Gly Gly Met Ala Ser Lys Trp Asp Gln Lys Gly Met Asp
1               5                  10                  15 atc gct tac gag gag gcc ctg ctg ggc tac aag gag ggc ggt gtg cct      96
Ile Ala Tyr Glu Glu Ala Leu Leu Gly Tyr Lys Glu Gly Gly Val Pro
            20                  25                  30 atc ggc ggc tgt ctg atc aac aac aag gac ggc agt gtg ctg ggc agg     144
Ile Gly Gly Cys Leu Ile Asn Asn Lys Asp Gly Ser Val Leu Gly Arg
        35                  40                  45 ggc cac aac atg agg ttc cag aag ggc tcc gcc acc ctg cac ggc gag     192
Gly His Asn Met Arg Phe Gln Lys Gly Ser Ala Thr Leu His Gly Glu
    50                  55                  60 atc tcc acc ctg gag aac tgt ggc agg ctg gag ggc aag gtg tac aag     240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc     288
```

-continued

| | | |
|---|---|---|
| Asp Thr Thr Leu Tyr Thr Thr Leu Ser Pro Cys Asp Met Cys Thr Gly<br>                  85                    90                  95 | | |
| gct atc atc atg tac ggc atc cct agg tgt gtg atc ggc gag aac gtg<br>Ala Ile Ile Met Tyr Gly Ile Pro Arg Cys Val Ile Gly Glu Asn Val<br>                100                   105                 110 | | 336 |
| aac ttc aag tcc aag ggc gag aag tac ctg caa acc agg ggc cac gag<br>Asn Phe Lys Ser Lys Gly Glu Lys Tyr Leu Gln Thr Arg Gly His Glu<br>           115                   120                 125 | | 384 |
| gtg gtg gtt gtt gac gat gag agg tgt aag aag ctg atg aag cag ttc<br>Val Val Val Val Asp Asp Glu Arg Cys Lys Lys Leu Met Lys Gln Phe<br>130                   135                   140 | | 432 |
| atc gac gag agg cct cag gac tgg ttc gag gat atc ggc gag tcc ggc<br>Ile Asp Glu Arg Pro Gln Asp Trp Phe Glu Asp Ile Gly Glu Ser Gly<br>145                 150                   155                 160 | | 480 |
| ggc ggc gcc tcc ggc ggc ggc gcc tcc ggc ggc ggc gcc tcc ggc ggc<br>Gly Gly Ala Ser Gly Gly Gly Ala Ser Gly Gly Gly Ala Ser Gly Gly<br>                 165                   170                 175 | | 528 |
| ggc gcc aac ccg tta ttc ttt ttg gct tct cca ttc ttg tac ctt aca<br>Gly Ala Asn Pro Leu Phe Phe Leu Ala Ser Pro Phe Leu Tyr Leu Thr<br>           180                         185                 190 | | 576 |
| tat ctt ata tat tat cca aac aaa ggg tct ttc gtt agc aaa cct aga<br>Tyr Leu Ile Tyr Tyr Pro Asn Lys Gly Ser Phe Val Ser Lys Pro Arg<br>         195                   200                 205 | | 624 |
| aat ctg caa aaa atg tct tcg gaa cca ttt aag aac gtc tac ttg cta<br>Asn Leu Gln Lys Met Ser Ser Glu Pro Phe Lys Asn Val Tyr Leu Leu<br>210                 215                   220 | | 672 |
| cct caa aca aac caa ttg ctg ggt ttg tac acc atc atc aga aat aag<br>Pro Gln Thr Asn Gln Leu Leu Gly Leu Tyr Thr Ile Ile Arg Asn Lys<br>225                 230                   235                 240 | | 720 |
| aat aca act aga cct gat ttc att ttc tac tcc gat aga atc atc aga<br>Asn Thr Thr Arg Pro Asp Phe Ile Phe Tyr Ser Asp Arg Ile Ile Arg<br>                 245                   250                 255 | | 768 |
| ttg ttg gtt gaa gaa ggt ttg aac cat cta cct gtg caa aag caa att<br>Leu Leu Val Glu Glu Gly Leu Asn His Leu Pro Val Gln Lys Gln Ile<br>           260                   265                 270 | | 816 |
| gtg gaa act gac acc aac gaa aac ttc gaa ggt gtc tca ttc atg ggt<br>Val Glu Thr Asp Thr Asn Glu Asn Phe Glu Gly Val Ser Phe Met Gly<br>         275                   280                 285 | | 864 |
| aaa atc tgt ggt gtt tcc att gtc aga gct ggt gaa tcg atg gag caa<br>Lys Ile Cys Gly Val Ser Ile Val Arg Ala Gly Glu Ser Met Glu Gln<br>290                 295                   300 | | 912 |
| gga tta aga gac tgt tgt agg tct gtg cgt atc ggt aaa att tta att<br>Gly Leu Arg Asp Cys Cys Arg Ser Val Arg Ile Gly Lys Ile Leu Ile<br>305                 310                   315                 320 | | 960 |
| caa agg gac gag gag act gct tta cca aag tta ttc tac gaa aaa tta<br>Gln Arg Asp Glu Glu Thr Ala Leu Pro Lys Leu Phe Tyr Glu Lys Leu<br>                 325                   330                 335 | | 1008 |
| cca gag gat ata tct gaa agg tat gtc ttc cta tta gac cca atg ctg<br>Pro Glu Asp Ile Ser Glu Arg Tyr Val Phe Leu Leu Asp Pro Met Leu<br>           340                      345                 350 | | 1056 |
| gcc acc ggt ggt agt gct atc atg gct aca gaa gtc ttg att aag aga<br>Ala Thr Gly Gly Ser Ala Ile Met Ala Thr Glu Val Leu Ile Lys Arg<br>         355                   360                 365 | | 1104 |
| ggt gtt aag cca gag aga att tac ttc tta aac cta atc tgt agt aag<br>Gly Val Lys Pro Glu Arg Ile Tyr Phe Leu Asn Leu Ile Cys Ser Lys<br>370                 375                   380 | | 1152 |
| gaa ggg att gaa aaa tac cat gcc gcc ttc cca gag gtc aga att gtt<br>Glu Gly Ile Glu Lys Tyr His Ala Ala Phe Pro Glu Val Arg Ile Val<br>385                 390                   395                 400 | | 1200 |
| act ggt gcc ctc gac aga ggt cta gat gaa aac aag tat cta gtt cca | | 1248 |

```
Thr Gly Ala Leu Asp Arg Gly Leu Asp Glu Asn Lys Tyr Leu Val Pro
            405                 410                 415 ggg ttg ggt gac ttt ggt gac aga tac tac tgt gtt taa                  1287
Gly Leu Gly Asp Phe Gly Asp Arg Tyr Tyr Cys Val
            420                 425

<210> SEQ ID NO 14
<211> LENGTH: 428
<212> TYPE: PRT
<213> ORGANISM: Artificial Sequence
<220> FEATURE:
<223> OTHER INFORMATION: Synthetic Construct

<400> SEQUENCE: 14

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ser Gly
145                 150                 155                 160

Gly Gly Ala Ser Gly Gly Gly Ala Ser Gly Gly Gly Ala Ser Gly Gly
                165                 170                 175

Gly Ala Asn Pro Leu Phe Phe Leu Ala Ser Pro Phe Leu Tyr Leu Thr
            180                 185                 190

Tyr Leu Ile Tyr Tyr Pro Asn Lys Gly Ser Phe Val Ser Lys Pro Arg
        195                 200                 205

Asn Leu Gln Lys Met Ser Ser Glu Pro Phe Lys Asn Val Tyr Leu Leu
    210                 215                 220

Pro Gln Thr Asn Gln Leu Leu Gly Leu Tyr Thr Ile Ile Arg Asn Lys
225                 230                 235                 240

Asn Thr Thr Arg Pro Asp Phe Ile Phe Tyr Ser Asp Arg Ile Ile Arg
                245                 250                 255

Leu Leu Val Glu Glu Gly Leu Asn His Leu Pro Val Gln Lys Gln Ile
            260                 265                 270

Val Glu Thr Asp Thr Asn Glu Asn Phe Glu Gly Val Ser Phe Met Gly
        275                 280                 285

Lys Ile Cys Gly Val Ser Ile Val Arg Ala Gly Glu Ser Met Glu Gln
    290                 295                 300

Gly Leu Arg Asp Cys Cys Arg Ser Val Arg Ile Gly Lys Ile Leu Ile
305                 310                 315                 320

Gln Arg Asp Glu Glu Thr Ala Leu Pro Lys Leu Phe Tyr Glu Lys Leu
                325                 330                 335
```

-continued

```
        Pro Glu Asp Ile Ser Glu Arg Tyr Val Phe Leu Asp Pro Met Leu
                    340                 345                 350

Ala Thr Gly Gly Ser Ala Ile Met Ala Thr Glu Val Leu Ile Lys Arg
                355                 360                 365

Gly Val Lys Pro Glu Arg Ile Tyr Phe Leu Asn Leu Ile Cys Ser Lys
                370                 375                 380

Glu Gly Ile Glu Lys Tyr His Ala Ala Phe Pro Glu Val Arg Ile Val
        385                 390                 395                 400

Thr Gly Ala Leu Asp Arg Gly Leu Asp Glu Asn Lys Tyr Leu Val Pro
                        405                 410                 415

Gly Leu Gly Asp Phe Gly Asp Arg Tyr Tyr Cys Val
                        420                 425

<210> SEQ ID NO 15
<211> LENGTH: 1200
<212> TYPE: DNA
<213> ORGANISM: Artificial Sequence
<220> FEATURE:
<223> OTHER INFORMATION: Fusion Construct - CDopt3 - OPRT
<220> FEATURE:
<221> NAME/KEY: CDS
<222> LOCATION: (1)..(1200)

<400> SEQUENCE: 15 atg gtg acc ggc ggc atg gcc tcc aag tgg gat caa aag ggc atg gat        48
Met Val Thr Gly Gly Met Ala Ser Lys Trp Asp Gln Lys Gly Met Asp
1               5                   10                  15 atc gct tac gag gag gcc ctg ctg ggc tac aag gag ggc ggc gtg cct        96
Ile Ala Tyr Glu Glu Ala Leu Leu Gly Tyr Lys Glu Gly Gly Val Pro
                20                  25                  30 atc ggc ggc tgt ctg atc aac aac aag gac ggc agt gtg ctg ggc agg       144
Ile Gly Gly Cys Leu Ile Asn Asn Lys Asp Gly Ser Val Leu Gly Arg
            35                  40                  45 ggc cac aac atg agg ttc cag aag ggc tcc gcc acc ctg cac ggc gag       192
Gly His Asn Met Arg Phe Gln Lys Gly Ser Ala Thr Leu His Gly Glu
        50                  55                  60 atc tcc acc ctg gag aac tgt ggc agg ctg gag ggc aag gtg tac aag       240
Ile Ser Thr Leu Glu Asn Cys Gly Arg Leu Glu Gly Lys Val Tyr Lys
65                  70                  75                  80 gac acc acc ctg tac acc acc ctg tcc cct tgt gac atg tgt acc ggc       288
Asp Thr Thr Leu Tyr Thr Thr Leu Ser Pro Cys Asp Met Cys Thr Gly
                85                  90                  95 gct atc atc atg tac ggc atc cct agg tgt gtg atc ggc gag aac gtg       336
Ala Ile Ile Met Tyr Gly Ile Pro Arg Cys Val Ile Gly Glu Asn Val
                100                 105                 110 aac ttc aag tcc aag ggc gag aag tac ctg caa acc agg ggc cac gag       384
Asn Phe Lys Ser Lys Gly Glu Lys Tyr Leu Gln Thr Arg Gly His Glu
            115                 120                 125 gtg gtg gtt gtt gac gat gag agg tgt aag aag ctg atg aag cag ttc       432
Val Val Val Val Asp Asp Glu Arg Cys Lys Lys Leu Met Lys Gln Phe
        130                 135                 140 atc gac gag agg cct cag gac tgg ttc gag gat atc ggc gag gcg gtc       480
Ile Asp Glu Arg Pro Gln Asp Trp Phe Glu Asp Ile Gly Glu Ala Val
145                 150                 155                 160 gct cgt gca gct ttg ggg cca ttg gtg acg ggt ctg tac gac gtg cag       528
Ala Arg Ala Ala Leu Gly Pro Leu Val Thr Gly Leu Tyr Asp Val Gln
                165                 170                 175 gct ttc aag ttt ggg gac ttc gtg ctg aag agc ggg ctt tcc tcc ccc       576
Ala Phe Lys Phe Gly Asp Phe Val Leu Lys Ser Gly Leu Ser Ser Pro
                180                 185                 190 atc tac atc gat ctg cgg ggc atc gtg tct cga ccg cgt ctt ctg agt       624
```

```
Ile Tyr Ile Asp Leu Arg Gly Ile Val Ser Arg Pro Arg Leu Leu Ser
        195                 200                 205 cag gtt gca gat att tta ttc caa act gcc caa aat gca ggc atc agt      672
Gln Val Ala Asp Ile Leu Phe Gln Thr Ala Gln Asn Ala Gly Ile Ser
210                 215                 220 ttt gac acc gtg tgt gga gtg cct tat aca gct ttg cca ttg gct aca      720
Phe Asp Thr Val Cys Gly Val Pro Tyr Thr Ala Leu Pro Leu Ala Thr
225                 230                 235                 240 gtt atc tgt tca acc aat caa att cca atg ctt att aga agg aaa gaa      768
Val Ile Cys Ser Thr Asn Gln Ile Pro Met Leu Ile Arg Arg Lys Glu
                245                 250                 255 aca aag gat tat gga act aag cgt ctt gta gaa gga act att aat cca      816
Thr Lys Asp Tyr Gly Thr Lys Arg Leu Val Glu Gly Thr Ile Asn Pro
            260                 265                 270 gga gaa acc tgt tta atc att gaa gat gtt gtc acc agt gga tct agt      864
Gly Glu Thr Cys Leu Ile Ile Glu Asp Val Val Thr Ser Gly Ser Ser
        275                 280                 285 gtt ttg gaa act gtt gag gtt ctt cag aag gag ggc ttg aag gtc act      912
Val Leu Glu Thr Val Glu Val Leu Gln Lys Glu Gly Leu Lys Val Thr
290                 295                 300 gat gcc ata gtg ctg ttg gac aga gag cag gga ggc aag gac aag ttg      960
Asp Ala Ile Val Leu Leu Asp Arg Glu Gln Gly Gly Lys Asp Lys Leu
305                 310                 315                 320 cag gcg cac ggg atc cgc ctc cac tca gtg tgt aca ttg tcc aaa atg     1008
Gln Ala His Gly Ile Arg Leu His Ser Val Cys Thr Leu Ser Lys Met
                325                 330                 335 ctg gag att ctc gag cag cag aaa aaa gtt gat gct gag aca gtt ggg     1056
Leu Glu Ile Leu Glu Gln Gln Lys Lys Val Asp Ala Glu Thr Val Gly
            340                 345                 350 aga gtg aag agg ttt att cag gag aat gtc ttt gtg gca gcg aat cat     1104
Arg Val Lys Arg Phe Ile Gln Glu Asn Val Phe Val Ala Ala Asn His
        355                 360                 365 aat ggt tct ccc ctt tct ata aag gaa gca ccc aaa gaa ctc agc ttc     1152
Asn Gly Ser Pro Leu Ser Ile Lys Glu Ala Pro Lys Glu Leu Ser Phe
370                 375                 380 ggt gca cgt gca gag ctg ccc agg atc cac cca gtt gca tcg aag taa     1200
Gly Ala Arg Ala Glu Leu Pro Arg Ile His Pro Val Ala Ser Lys
385                 390                 395

<210> SEQ ID NO 16
<211> LENGTH: 399
<212> TYPE: PRT
<213> ORGANISM: Artificial Sequence
<220> FEATURE:
<223> OTHER INFORMATION: Synthetic Construct

<400> SEQUENCE: 16

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
```

```
                    100                 105                 110
Asn Phe Lys Ser Lys Gly Glu Lys Tyr Leu Gln Thr Arg Gly His Glu
            115                 120                 125

Val Val Val Asp Asp Glu Arg Cys Lys Lys Leu Met Lys Gln Phe
        130                 135                 140

Ile Asp Glu Arg Pro Gln Asp Trp Phe Glu Asp Ile Gly Glu Ala Val
145                 150                 155                 160

Ala Arg Ala Ala Leu Gly Pro Leu Val Thr Gly Leu Tyr Asp Val Gln
            165                 170                 175

Ala Phe Lys Phe Gly Asp Phe Val Leu Lys Ser Gly Leu Ser Ser Pro
        180                 185                 190

Ile Tyr Ile Asp Leu Arg Gly Ile Val Ser Arg Pro Arg Leu Leu Ser
            195                 200                 205

Gln Val Ala Asp Ile Leu Phe Gln Thr Ala Gln Asn Ala Gly Ile Ser
        210                 215                 220

Phe Asp Thr Val Cys Gly Val Pro Tyr Thr Ala Leu Pro Leu Ala Thr
225                 230                 235                 240

Val Ile Cys Ser Thr Asn Gln Ile Pro Met Leu Ile Arg Arg Lys Glu
            245                 250                 255

Thr Lys Asp Tyr Gly Thr Lys Arg Leu Val Glu Gly Thr Ile Asn Pro
        260                 265                 270

Gly Glu Thr Cys Leu Ile Ile Glu Asp Val Val Thr Gly Ser Ser
            275                 280                 285

Val Leu Glu Thr Val Glu Val Leu Gln Lys Gly Leu Lys Val Thr
        290                 295                 300

Asp Ala Ile Val Leu Leu Asp Arg Glu Gln Gly Gly Lys Asp Lys Leu
305                 310                 315                 320

Gln Ala His Gly Ile Arg Leu His Ser Val Cys Thr Leu Ser Lys Met
            325                 330                 335

Leu Glu Ile Leu Glu Gln Lys Lys Val Asp Ala Glu Thr Val Gly
            340                 345                 350

Arg Val Lys Arg Phe Ile Gln Glu Asn Val Phe Val Ala Ala Asn His
        355                 360                 365

Asn Gly Ser Pro Leu Ser Ile Lys Glu Ala Pro Lys Glu Leu Ser Phe
        370                 375                 380

Gly Ala Arg Ala Glu Leu Pro Arg Ile His Pro Val Ala Ser Lys
385                 390                 395

<210> SEQ ID NO 17
<211> LENGTH: 1260
<212> TYPE: DNA
<213> ORGANISM: Artificial Sequence
<220> FEATURE:
<223> OTHER INFORMATION: Fusion Construct - CDopt3 - linker - OPRT
<220> FEATURE:
<221> NAME/KEY: CDS
<222> LOCATION: (1)..(1260)

<400> SEQUENCE: 17 atg gtg acc ggc ggc atg gcc tcc aag tgg gat caa aag ggc atg gat    48
Met Val Thr Gly Gly Met Ala Ser Lys Trp Asp Gln Lys Gly Met Asp
1               5                   10                  15 atc gct tac gag gag gcc ctg ctg ggc tac aag gag ggc ggc gtg cct    96
Ile Ala Tyr Glu Glu Ala Leu Leu Gly Tyr Lys Glu Gly Gly Val Pro
            20                  25                  30 atc ggc ggc tgt ctg atc aac aac aag gac ggc agt gtg ctg ggc agg   144
Ile Gly Gly Cys Leu Ile Asn Asn Lys Asp Gly Ser Val Leu Gly Arg
        35                  40                  45
```

```
ggc cac aac atg agg ttc cag aag ggc tcc gcc acc ctg cac ggc gag      192
Gly His Asn Met Arg Phe Gln Lys Gly Ser Ala Thr Leu His Gly Glu
         50                  55                  60 atc tcc acc ctg gag aac tgt ggc agg ctg gag ggc aag gta tac aag      240
Ile Ser Thr Leu Glu Asn Cys Gly Arg Leu Glu Gly Lys Val Tyr Lys
 65                  70                  75                  80 gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                 85                  90                  95 gct atc atc atg tac ggc atc cct agg tgt gtg atc ggc gag aac gtg      336
Ala Ile Ile Met Tyr Gly Ile Pro Arg Cys Val Ile Gly Glu Asn Val
                100                 105                 110 aac ttc aag tcc aag ggc gag aag tac ctg caa acc agg ggc cac gag      384
Asn Phe Lys Ser Lys Gly Glu Lys Tyr Leu Gln Thr Arg Gly His Glu
        115                 120                 125 gtg gtg gtt gtt gac gat gag agg tgt aag aag ctg atg aag cag ttc      432
Val Val Val Val Asp Asp Glu Arg Cys Lys Lys Leu Met Lys Gln Phe
    130                 135                 140 atc gac gag agg cct cag gac tgg ttc gag gat atc ggc gag tcc ggc      480
Ile Asp Glu Arg Pro Gln Asp Trp Phe Glu Asp Ile Gly Glu Ser Gly
145                 150                 155                 160 ggc ggc gcc tcc ggc ggc ggc gcc tcc ggc ggc ggc gcc tcc ggc ggc      528
Gly Gly Ala Ser Gly Gly Gly Ala Ser Gly Gly Gly Ala Ser Gly Gly
                165                 170                 175 ggc gcc gcg gtc gct cgt gca gct ttg ggg cca ttg gtg acg ggt ctg      576
Gly Ala Ala Val Ala Arg Ala Ala Leu Gly Pro Leu Val Thr Gly Leu
                180                 185                 190 tac gac gtg cag gct ttc aag ttt ggg gac ttc gtg ctg aag agc ggg      624
Tyr Asp Val Gln Ala Phe Lys Phe Gly Asp Phe Val Leu Lys Ser Gly
            195                 200                 205 ctt tcc tcc ccc atc tac atc gat ctg cgg ggc atc gtg tct cga ccg      672
Leu Ser Ser Pro Ile Tyr Ile Asp Leu Arg Gly Ile Val Ser Arg Pro
        210                 215                 220 cgt ctt ctg agt cag gtt gca gat att tta ttc caa act gcc caa aat      720
Arg Leu Leu Ser Gln Val Ala Asp Ile Leu Phe Gln Thr Ala Gln Asn
225                 230                 235                 240 gca ggc atc agt ttt gac acc gtg tgt gga gtg cct tat aca gct ttg      768
Ala Gly Ile Ser Phe Asp Thr Val Cys Gly Val Pro Tyr Thr Ala Leu
                245                 250                 255 cca ttg gct aca gtt atc tgt tca acc aat caa att cca atg ctt att      816
Pro Leu Ala Thr Val Ile Cys Ser Thr Asn Gln Ile Pro Met Leu Ile
                260                 265                 270 aga agg aaa gaa aca aag gat tat gga act aag cgt ctt gta gaa gga      864
Arg Arg Lys Glu Thr Lys Asp Tyr Gly Thr Lys Arg Leu Val Glu Gly
            275                 280                 285 act att aat cca gga gaa acc tgt tta atc att gaa gat gtt gtc acc      912
Thr Ile Asn Pro Gly Glu Thr Cys Leu Ile Ile Glu Asp Val Val Thr
        290                 295                 300 agt gga tct agt gtt ttg gaa act gtt gag gtt ctt cag aag gag ggc      960
Ser Gly Ser Ser Val Leu Glu Thr Val Glu Val Leu Gln Lys Glu Gly
305                 310                 315                 320 ttg aag gtc act gat gcc ata gtg ctg ttg gac aga gag cag gga ggc     1008
Leu Lys Val Thr Asp Ala Ile Val Leu Leu Asp Arg Glu Gln Gly Gly
                325                 330                 335 aag gac aag ttg cag gcg cac ggg atc cgc ctc cac tca gtg tgt aca     1056
Lys Asp Lys Leu Gln Ala His Gly Ile Arg Leu His Ser Val Cys Thr
                340                 345                 350 ttg tcc aaa atg ctg gag att ctc gag cag cag aaa aaa gtt gat gct     1104
Leu Ser Lys Met Leu Glu Ile Leu Glu Gln Gln Lys Lys Val Asp Ala
            355                 360                 365
```

```
gag aca gtt ggg aga gtg aag agg ttt att cag gag aat gtc ttt gtg      1152
Glu Thr Val Gly Arg Val Lys Arg Phe Ile Gln Glu Asn Val Phe Val
    370                 375                 380 gca gcg aat cat aat ggt tct ccc ctt tct ata aag gaa gca ccc aaa      1200
Ala Ala Asn His Asn Gly Ser Pro Leu Ser Ile Lys Glu Ala Pro Lys
385                 390                 395                 400 gaa ctc agc ttc ggt gca cgt gca gag ctg ccc agg atc cac cca gtt      1248
Glu Leu Ser Phe Gly Ala Arg Ala Glu Leu Pro Arg Ile His Pro Val
                405                 410                 415 gca tcg aag taa                                                       1260
Ala Ser Lys <210> SEQ ID NO 18
<211> LENGTH: 419
<212> TYPE: PRT
<213> ORGANISM: Artificial Sequence
<220> FEATURE:
<223> OTHER INFORMATION: Synthetic Construct

<400> SEQUENCE: 18

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Val Pro
            20                  25                  30

Ile Gly Gly Cys Leu Ile Asn Asn Lys Asp Gly Ser Val Leu Gly Arg
            35                  40                  45

Gly His Asn Met Arg Phe Gln Lys Gly Ser Ala Thr Leu His Gly Glu
        50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ser Gly
145                 150                 155                 160

Gly Gly Ala Ser Gly Gly Ala Ser Gly Gly Ala Ser Gly Gly
                165                 170                 175

Gly Ala Ala Val Ala Arg Ala Ala Leu Gly Pro Leu Val Thr Gly Leu
            180                 185                 190

Tyr Asp Val Gln Ala Phe Lys Phe Gly Asp Phe Val Leu Lys Ser Gly
        195                 200                 205

Leu Ser Ser Pro Ile Tyr Ile Asp Leu Arg Gly Ile Val Ser Arg Pro
    210                 215                 220

Arg Leu Leu Ser Gln Val Ala Asp Ile Leu Phe Gln Thr Ala Gln Asn
225                 230                 235                 240

Ala Gly Ile Ser Phe Asp Thr Val Cys Gly Val Pro Tyr Thr Ala Leu
                245                 250                 255

Pro Leu Ala Thr Val Ile Cys Ser Thr Asn Gln Ile Pro Met Leu Ile
            260                 265                 270

Arg Arg Lys Glu Thr Lys Asp Tyr Gly Thr Lys Arg Leu Val Glu Gly
        275                 280                 285
```

```
Thr Ile Asn Pro Gly Glu Thr Cys Leu Ile Ile Glu Asp Val Val Thr
    290                 295                 300
Ser Gly Ser Ser Val Leu Glu Thr Val Glu Val Leu Gln Lys Glu Gly
305                 310                 315                 320
Leu Lys Val Thr Asp Ala Ile Val Leu Leu Asp Arg Glu Gln Gly Gly
                325                 330                 335
Lys Asp Lys Leu Gln Ala His Gly Ile Arg Leu His Ser Val Cys Thr
            340                 345                 350
Leu Ser Lys Met Leu Glu Ile Leu Glu Gln Gln Lys Lys Val Asp Ala
        355                 360                 365
Glu Thr Val Gly Arg Val Lys Arg Phe Ile Gln Glu Asn Val Phe Val
    370                 375                 380
Ala Ala Asn His Asn Gly Ser Pro Leu Ser Ile Lys Glu Ala Pro Lys
385                 390                 395                 400
Glu Leu Ser Phe Gly Ala Arg Ala Glu Leu Pro Arg Ile His Pro Val
                405                 410                 415
Ala Ser Lys

<210> SEQ ID NO 19
<211> LENGTH: 11892
<212> TYPE: DNA
<213> ORGANISM: Artificial Sequence
<220> FEATURE:
<223> OTHER INFORMATION: RCR Vector - pAC3-yCD2

<400> SEQUENCE: 19
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta caactccgcc ccattgacgc aaatgggcg gtaggcgtgt     540
acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actaccgtc agcggggtc       720
tttcatttgg gggctcgtcc gggatcggga gaccctgcc cagggaccac cgacccacca     780
ccgggaggta agctggccag caacttatct gtgtctgtcc gattgtctag tgtctatgac     840
tgattttatg cgcctgcgtc ggtactagtt agctaactag ctctgtatct ggcggacccg     900
tggtggaact gacgagttcg aacacccgg ccgcaaccct gggagacgtc ccagggactt     960
cgggggccgt ttttgtggcc cgacctgagt ccaaaaatcc cgatcgtttt ggactctttg    1020
gtgcaccccc cttagaggag ggatatgtgg ttctggtagg agacgagaac ctaaaacagt    1080
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaga    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
```

```
ctgcagaatg gccaaccttt aacgtcggat ggccgcgaga cggcaccttt aaccgagacc    1380
tcatcaccca ggttaagatc aaggtctttt cacctggccc gcatggacac ccagaccagg    1440
tcccctacat cgtgacctgg gaagccttgg cttttgaccc ccctccctgg gtcaagccct    1500
ttgtacaccc taagcctccg cctcctcttc tccatccgc cccgtctctc ccccttgaac    1560
ctcctcgttc gaccccgcct cgatcctccc tttatccagc cctcactcct tctctaggcg    1620
ccaaacctaa acctcaagtt ctttctgaca gtggggggcc gctcatcgac ctacttacag    1680
aagacccccc gccttatagg acccaagac cacccccttc cgacagggac ggaaatggtg    1740
gagaagcgac ccctgcggga gaggcaccgg acccctcccc aatggcatct cgcctacgtg    1800
ggagacggga gcccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttcttttttct gaagatccag gtaaactgac agctctgatc gagtctgttc    1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc gggggcaac    2880 ccgtcacctt cctggtagat actggggccc aacactccgt gctgacccaa atcctggac    2940 ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagccccac atacagagac    3420
tgttggacca gggaatactg gtaccctgcc agtccccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600 cgtcсccacca gtggtacact gtgctgatt aaaggatgc cttttctgc ctgagactcc    3660 accccaccag tcagcctctc ttcgcctttg agtggagaga tccagagatg ggaatctcag    3720
```

```
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaaccta gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gcccttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggcccaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca gcggcccga aaggcagcca    5160 tcacagagac tccagacacc tctaccctcc tcatagaaaa ttcatcaccc tacacctcag    5220
aacattttca ttacacagtg actgatataa aggacctaac caagttgggg gccatttatg    5280 ataaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggccggca ctcattggga gatcgatttc accgagataa    5580
agcccggatt gtatggctat aaatatcttc tagtttttat agatacctt tctggctgga    5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttgggat tgattggaaa ttacattgtg    5820
catacagacc ccaaagctca ggccaggtag aaagaatgaa tagaaccatc aaggagactt    5880
taactaaatt aacgcttgca actggctcta gagactgggg gctcctactc cccttagccc    5940
tgtaccgagc ccgcaacacg ccgggccccc atggcctcac cccatatgag atcttatatg    6000 ggcaccccc gccccttgta aacttccctg acctgacat gacaagagtt actaacagcc    6060
cctctctcca agctcactta caggctctct acttagtcca gcacgaagtc tggagacctc    6120
```

```
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt agacggcatc gcagcttgga    6300
tacacgccgc ccacgtgaag gctgccgacc ccggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttg acttttacgt gtgccctggg cataccgtaa agtcggggtg    6720
tgggggacca ggagagggct actgtggtaa atgggggtgt gaaaccaccg acaggctta    6780 ctggaagccc acatcatcgt gggacctaat ctcccttaag cgcggtaaca cccctgggga    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagccccct caataccagt taccccccctt ccactaccag    7200 tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680 ctccccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat tgctattcc taaaggaggg    7980 aggtctctgc gcagccctaa agaagaatg ttgttttat gcagaccaca cggggctagt    8040
gagagacagc atggccaaat taagagaaag gcttaatcag agacaaaaac tatttgagac    8100
aggccaagga tggttcgaag ggctgtttaa tagatcccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca tgaacgcgtt actgccgaa    8340 gccgcttgga ataaggccgg tgtgcgtttg tctatatgtt attttccacc atattgccgt    8400
cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
```

```
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgaccggcgg catggcctcc aagtgggatc aaaagggcat ggatatcgct tacgaggagg    8940
ccctgctggg ctacaaggag ggcggcgtgc ctatcggcgg ctgtctgatc aacaacaagg    9000
acggcagtgt gctgggcagg ggccacaaca tgaggttcca aagggctcc gccaccctgc    9060
acggcgagat ctccaccctg gagaactgtg gcaggctgga gggcaaggtg tacaaggaca    9120
ccaccctgta caccaccctg tcccttgtg acatgtgtac cggcgctatc atcatgtacg    9180
gcatccctag gtgtgtgatc ggcgagaacg tgaacttcaa gtccaaggc gagaagtacc    9240
tgcaaaccag gggccacgag gtggtggttg ttgacgatga gaggtgtaag aagctgatga    9300
agcagttcat cgacgagagg cctcaggact ggttcgagga tatcggcgag taagcggccg    9360
cagataaaat aaaagatttt atttagtctc cagaaaaagg ggggaatgaa agaccccacc    9420
tgtaggtttg gcaagctagc ttaagtaacg ccatttttgca aggcatggaa aatacataa    9480
ctgagaatag agaagttcag atcaaggtca ggaacagatg gaacagctga atatgggcca    9540
aacaggatat ctgtggtaag cagttcctgc cccggctcag ggccaagaac agatggaaca    9600
gctgaatatg ggccaaacag gatatctgtg gtaagcagtt cctgccccgg ctcagggcca    9660
agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctccccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcggggt ctttcattac atgtgagcaa aaggccagca    10020
aaaggccagg aaccgtaaaa aggccgcgtt gctggcgttt ttccataggc tccgcccccc    10080
tgacgagcat cacaaaaatc gacgctcaag tcagaggtgg cgaaacccga caggactata    10140
aagataccag gcgtttcccc ctggaagctc cctcgtgcgc tctcctgttc cgaccctgcc    10200
gcttaccgga tacctgtccg cctttctccc ttcgggaagc gtggcgcttt ctcaatgctc    10260
acgctgtagg tatctcagtt cggtgtaggt cgttcgctcc aagctgggct gtgtgcacga    10320
accccccgtt cagcccgacc gctgcgcctt atccggtaac tatcgtcttg agtccaaccc    10380
ggtaagacac gacttatcgc cactggcagc agccactggt aacaggatta gcagagcgag    10440
gtatgtaggc ggtgctacag agttcttgaa gtggtggcct aactacggct acactagaag    10500
gacagtattt ggtatctgcg ctctgctgaa gccagttacc ttcggaaaaa gagttggtag    10560
ctcttgatcc ggcaaacaaa ccaccgctgg tagcggtggt ttttttgttt gcaagcagca    10620
gattacgcgc agaaaaaaag gatctcaaga agatcctttg atcttttcta cggggtctga    10680
cgctcagtgg aacgaaaact cacgttaagg gattttggtc atgagattat caaaaaggat    10740
cttcacctag atccttttaa attaaaaatg aagttttaaa tcaatctaaa gtatatatga    10800
gtaaacttgg tctgacagtt accaatgctt aatcagtgag gcacctatct cagcgatctg    10860
tctatttcgt tcatccatag ttgcctgact ccccgtcgtg tagataacta cgatacggga    10920
```

```
gggcttacca tctggcccca gtgctgcaat gataccgcga gacccacgct caccggctcc   10980
agatttatca gcaataaacc agccagccgg aagggccgag cgcagaagtg gtcctgcaac   11040
tttatccgcc tccatccagt ctattaattg ttgccgggaa gctagagtaa gtagttcgcc   11100
agttaatagt ttgcgcaacg ttgttgccat tgctgcaggc atcgtggtgt cacgctcgtc   11160
gtttggtatg gcttcattca gctccggttc ccaacgatca aggcgagtta catgatcccc   11220
catgttgtgc aaaaaagcgg ttagctcctt cggtcctccg atcgttgtca gaagtaagtt   11280
ggccgcagtg ttatcactca tggttatggc agcactgcat aattctctta ctgtcatgcc   11340
atccgtaaga tgcttttctg tgactggtga gtactcaacc aagtcattct gagaatagtg   11400
tatgcggcga ccgagttgct cttgcccggc gtcaacacgg gataataccg cgccacatag   11460
cagaacttta aaagtgctca tcattggaaa acgttcttcg gggcgaaaac tctcaaggat   11520
cttaccgctg ttgagatcca gttcgatgta acccactcgt gcacccaact gatcttcagc   11580
atcttttact ttcaccagcg tttctgggtg agcaaaaaca ggaaggcaaa atgccgcaaa   11640
aaagggaata agggcgacac ggaaatgttg aatactcata ctcttccttt tcaatatta   11700
ttgaagcatt tatcagggtt attgtctcat gagcggatac atatttgaat gtatttagaa   11760
aaataaacaa ataggggttc cgcgcacatt tccccgaaaa gtgccacctg acgtctaaga   11820
aaccattatt atcatgacat taacctataa aaataggcgt atcacgaggc cctttcgtct   11880
tcaagaattc at                                                       11892

<210> SEQ ID NO 20
<211> LENGTH: 11892
<212> TYPE: DNA
<213> ORGANISM: Artificial Sequence
<220> FEATURE:
<223> OTHER INFORMATION: RCR Vector - pAC3-yCD

<400> SEQUENCE: 20
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcggggtc    720
tttcatttgg gggctcgtcc gggatcggga accccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc caggggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
```

```
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaga    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaaccttt aacgtcggat ggccgcgaga cggcacctt aaccgagacc     1380
tcatcaccca ggttaagatc aaggtctttt cacctggccc gcatggacac ccagaccagg    1440
tcccctacat cgtgacctgg gaagccttgg cttttgaccc ccctccctgg gtcaagccct    1500
ttgtacaccc taagcctccg cctcctcttc tccatccgc cccgtctctc ccccttgaac     1560
ctcctcgttc gaccccgcct cgatcctccc tttatccagc cctcactcct tctctaggcg    1620
ccaaacctaa acctcaagtt ctttctgaca gtgggggggcc gctcatcgac ctacttacag   1680
aagacccccc gccttatagg gacccaagac cacccccttc cgacagggac ggaaatggtg    1740
gagaagcgac ccctgcggga gaggcaccgg acccctcccc aatggcatct cgcctacgtg    1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttctttttct gaagatccag gtaaactgac agctctgatc gagtctgttc    1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg gctaaagat tgtcccaaga    2760
aaccacgagg acctcgggga ccaagacccc agacctccct cctgacccta gatgactagg    2820
gaggtcaggg tcaggagccc ccccctgaac ccaggataac cctcaaagtc ggggggcaac    2880
ccgtcacctt cctggtagat actggggccc aacactccgt gctgacccaa atcctggac    2940
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag catcggctac atgagacctc aaaagagcca gatgtttctc    3240
tagggtccac atggctgtct gattttcctc aggcctgggc ggaaaccggg gcatgggac    3300
tggcagttcg ccaagctcct ctgatcatac ctctgaaagc aacctctacc cccgtgtcca    3360
taaaacaata cccccatgtca caagaagcca gactggggat caagcccac atacagagac    3420
tgttggacca gggaatactg gtaccctgcc agtcccctg gaacacgccc ctgctacccg    3480
```

```
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttctgc ctgagactcc     3660 accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaaccta gggaacctcg ggtatcgggc ctcggccaag aaagcccaaa     3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gccctttgaa ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agacttctt catcagctga ctcacctcag cttctcaaaa atgaaggctc      5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccgca ctcattggga gatcgatttc accgagataa     5580 agccccggatt gtatggctat aaatatcttc tagtttttat agatacctttt ctggctgga    5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgtttgggat tgattggaaa ttacattgtg    5820
catacagacc ccaaagctca ggccaggtag aaagaatgaa tagaaccatc aaggagactt    5880
```

```
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccaccg ccctcaaagt agacggcatc gcagcttgga     6300
tacacgccgc ccacgtgaag gctgccgacc ccggggggtgg accatcctct agactgacat   6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggacttttg acttttacgt gtgccctggg cataccgtaa agtcggggtg    6720
tgggggacca ggagagggct actgtggtaa atggggggtgt gaaaccaccg gacaggctta   6780
ctggaagccc acatcatcgt gggacctaat ctcccttaag cgcggtaaca cccccctggga  6840
cacgggatgc tctaaagttg cctgtggccc ctgctacgac ctctccaaag tatccaattc    6900
cttccagggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg acccccgagt    7080
ccccataggg cccaacccag tattacccga ccaaagactc ccttcctcac caatagagat    7140
tgtaccggct ccacagccac ctagcccct caataccagt tacccccctt ccactaccag     7200
tacaccctca acctccccta caagtccaag tgtcccacag ccaccccccag gaactggaga   7260
tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctccccccgat tatatgtatg gtcagcttga acagcgtacc aaatataaaa gagagccagt   7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat tgctattcc taaaggaggg    7980
aggtctctgc gcagccctaa agaagaatg ttgttttat gcagaccaca cggggctagt      8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggtttttga    8280
```

```
tcagcaatat caccagctaa aacccataga gtacgagcca tgaacgcgtt actggccgaa    8340
gccgcttgga ataaggccgg tgtgcgtttg tctatatgtt attttccacc atattgccgt    8400
cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgacaggggg aatggcaagc aagtgggatc agaagggtat ggacattgcc tatgaggagg    8940
cggccttagg ttacaaagag ggtggtgttc ctattggcgg atgtcttatc aataacaaag    9000
acggaagtgt tctcggtcgt ggtcacaaca tgagatttca aaagggatcc gccacactac    9060
atggtgagat ctccactttg gaaaactgtg ggagattaga gggcaaagtg tacaaagata    9120
ccactttgta tacgacgctg tctccatgcg acatgtgtac aggtgccatc atcatgtatg    9180
gtattccacg ctgtgttgtc ggtgagaacg ttaatttcaa aagtaagggc gagaaatatt    9240
tacaaactag aggtcacgag gttgttgttg ttgacgatga gaggtgtaaa aagatcatga    9300
aacaatttat cgatgaaaga cctcaggatt ggtttgaaga tattggtgag taggcggccg    9360
cagataaaat aaaagatttt atttagtctc cagaaaaagg ggggaatgaa agaccccacc    9420
tgtaggtttg gcaagctagc ttaagtaacg ccatttttgca aggcatggaa aaatacataa    9480
ctgagaatag agaagttcag atcaaggtca ggaacagatg gaacagctga atatgggcca    9540
aacaggatat ctgtggtaag cagttcctgc cccggctcag ggccaagaac agatggaaca    9600
gctgaatatg gccaaacag gatatctgtg gtaagcagtt cctgccccgg ctcagggcca    9660
agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctccccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcgggggt ctttcattac atgtgagcaa aaggccagca   10020
aaaggccagg aaccgtaaaa aggccgcgtt gctggcgttt ttccataggc tccgccccc   10080 tgacgagcat cacaaaaatc gacgctcaag tcagaggtgg cgaaacccga caggactata   10140
aagataccag gcgtttcccc ctggaagctc cctcgtgcgc tctcctgttc cgaccctgcc   10200
gcttaccgga tacctgtccg cctttctccc ttcgggaagc gtggcgcttt ctcaatgctc   10260
acgctgtagg tatctcagtt cggtgtaggt cgttcgctcc aagctgggct gtgtgcacga   10320
accccccgtt cagcccgacc gctgcgcctt atccggtaac tatcgtcttg agtccaaccc   10380
ggtaagacac gacttatcgc cactggcagc agccactggt aacaggatta gcagagcgag   10440
gtatgtaggc ggtgctacag agttcttgaa gtggtggcct aactacggct acactagaag   10500
gacagtattt ggtatctgcg ctctgctgaa gccagttacc ttcggaaaaa gagttggtag   10560
ctcttgatcc ggcaaacaaa ccaccgctgg tagcggtggt ttttttgttt gcaagcagca   10620
gattacgcgc agaaaaaaag gatctcaaga agatcctttg atcttttcta cggggtctga   10680
```

-continued

```
cgctcagtgg aacgaaaact cacgttaagg gattttggtc atgagattat caaaaaggat    10740
cttcacctag atccttttaa attaaaaatg aagttttaaa tcaatctaaa gtatatatga    10800
gtaaacttgg tctgacagtt accaatgctt aatcagtgag gcacctatct cagcgatctg    10860
tctatttcgt tcatccatag ttgcctgact ccccgtcgtg tagataacta cgatacggga    10920
gggcttacca tctggcccca gtgctgcaat gataccgcga gacccacgct caccggctcc    10980
agatttatca gcaataaacc agccagccgg aagggccgag cgcagaagtg gtcctgcaac    11040
tttatccgcc tccatccagt ctattaattg ttgccgggaa gctagagtaa gtagttcgcc    11100
agttaatagt ttgcgcaacg ttgttgccat tgctgcaggc atcgtggtgt cacgctcgtc    11160
gtttggtatg gcttcattca gctccggttc ccaacgatca aggcgagtta catgatcccc    11220
catgttgtgc aaaaaagcgg ttagctcctt cggtcctccg atcgttgtca gaagtaagtt    11280
ggccgcagtg ttatcactca tggttatggc agcactgcat aattctctta ctgtcatgcc    11340
atccgtaaga tgcttttctg tgactggtga gtactcaacc aagtcattct gagaatagtg    11400
tatgcggcga ccgagttgct cttgcccggc gtcaacacgg gataataccg cgccacatag    11460
cagaacttta aaagtgctca tcattggaaa acgttcttcg gggcgaaaac tctcaaggat    11520
cttaccgctg ttgagatcca gttcgatgta acccactcgt gcacccaact gatcttcagc    11580
atcttttact tcaccagcg tttctgggtg agcaaaaaca ggaaggcaaa atgccgcaaa    11640
aaagggaata agggcgacac ggaaatgttg aatactcata ctcttccttt ttcaatatta    11700
ttgaagcatt tatcagggtt attgtctcat gagcggatac atatttgaat gtatttagaa    11760
aaataaacaa ataggggttc cgcgcacatt tccccgaaaa gtgccacctg acgtctaaga    11820
aaccattatt atcatgacat taacctataa aaataggcgt atcacgaggc cctttcgtct    11880
tcaagaattc at                                                        11892
```

<210> SEQ ID NO 21
<211> LENGTH: 12007
<212> TYPE: DNA
<213> ORGANISM: Artificial Sequence
<220> FEATURE:
<223> OTHER INFORMATION: RCR Vector - pACE-CD

<400> SEQUENCE: 21

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actacccgtc agcggggggtc     720 tttcatttgg gggctcgtcc gggatcggga gacccctgcc cagggaccac cgacccacca     780
ccgggaggta agctggccag caacttatct gtgtctgtcc gattgtctag tgtctatgac     840
```

```
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc tccatccgc cccgtctctc cccttgaac    1560 ctcctcgttc gaccccgcct cgatcctccc tttatccagc cctcactcct tctctaggcg   1620
ccaaacctaa acctcaagtt cttttctgaca gtgggggggcc gctcatcgac ctacttacag   1680 aagaccccc gccttatagg gacccaagac cacccccttc cgacagggac ggaaatggtg    1740
gagaagcgac ccctgcggga gaggcaccgg acccctcccc aatggcatct cgcctacgtg   1800
ggagacggga gcccctgtg ccgactcca ctacctcgca ggcattcccc ctccgcgcag    1860
gaggaaacgg acagcttcaa tactggccgt tctcctcttc tgacctttac aactggaaaa   1920
ataataaccc ttcttttttct gaagatccag gtaaactgac agctctgatc gagtctgttc   1980
tcatcaccca tcagcccacc tgggacgact gtcagcagct gttggggact ctgctgaccg   2040
gagaagaaaa acaacggtg ctcttagagg ctagaaaggc ggtgcggggc gatgatgggc    2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa acaagacgc    2460 ttggagattt ggttagagag gcagaaaaga tctttaataa cgagaaacc ccggaagaaa    2520 gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc cccctgaac ccaggataac cctcaaagtc gggggggcaac    2880 ccgtcacctt cctggtagat actgggggcc aacactccgt gctgacccaa aatcctggac   2940
ccctaagtga taagtctgcc tgggtccaag gggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag catcggctac atgagacctc aaaagagcca gatgtttctc   3240
```

-continued

```
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagcccac  atacagagac    3420 tgttggacca gggaatactg gtaccctgcc agtcccctg  gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttctgc  ctgagactcc    3660 accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaaccta  gggaacctcg ggtatcgggc ctcggccaag aaagcccaaa    3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140 cagcccctt  gtaccctctc accaaaacgg ggactctgtt taattgggc  ccagaccaac    4200 aaaaggccta tcaagaaatc aagcaagctc ttctaactgc cccagccctg gggttgccag    4260
atttgactaa gcccttgaa  ctctttgtcg acgagaagca gggctacgcc aaaggtgtcc    4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cggacatccc gctcagcggg    4860
ctgaactgat agcactcacc caggccctaa agatggcaga aggtaagaag ctaaatgttt    4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccgca  ctcattggga gatcgatttc accgagataa    5580 agccccggatt gtatggctat aaatatcttc tagttttat  agataccttt tctggctgga    5640
```

```
tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc accccaccg ccctcaaagt agacggcatc gcagcttgga    6300
tacacgccgc ccacgtgaag gctgccgacc ccggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggacttttg acttttacgt gtgccctggg cataccgtaa agtcggggtg    6720
tgggggacca ggagagggct actgtggtaa atggggggtgt gaaaccaccg gacaggctta    6780
ctggaagccc acatcatcgt gggacctaat ctcccttaag cgcggtaaca cccctggga    6840 cacgggatgc tctaaagttg cctgtggccc ctgctacgac ctctccaaag tatccaattc    6900
cttccagggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080 ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atggggcag tacctaaaac    7500 tcaccaggcc ttatgtaaca ccacccaaag cgccggctca ggatcctact accttgcagc    7560
acccgccgga caatgtgggg cttgcagcac tggattgact ccctgcttgt ccaccacggt    7620
gctcaatcta accacagatt attgtgtatt agttgaactc tggcccagag taatttacca    7680 ctccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgttttttat gcagaccaca cggggctagt    8040
```

```
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgatta gtccaatttg ttaaagacag gatatcagtg gtccaggctc tagttttgac    8280
tcaacaatat caccagctga agcctataga gtacgagcca tgacgtacgt tactggccga    8340
agccgcttgg aataaggccg gtgtgcgttt gtctatatgt tattttccac catattgccg    8400
tcttttggca atgtgagggc ccggaaacct ggccctgtct tcttgacgag cattcctagg    8460
ggtctttccc ctctcgccaa aggaatgcaa gtctgttga atgtcgtgaa ggaagcagtt     8520
cctctggaag cttcttgaag acaaacaacg tctgtagcga ccctttgcag gcagcggaac    8580
cccccacctg gcgacaggtg cctctgcggc caaaagccac gtgtataaga tacacctgca    8640
aaggcggcac aaccccagtg ccacgttgtg agttggatag ttgtggaaag agtcaaatgg    8700
ctctcctcaa gcgtattcaa caaggggctg aaggatgccc agaaggtacc ccattgtatg    8760
ggatctgatc tggggcctcg gtgcacatgc tttacatgtg tttagtcgag gttaaaaaaa    8820
cgtctaggcc ccccgaacca cggggacgtg gttttccttt gaaaaacacg ataataccat    8880
ggtgacaggg ggaatggcaa gcaagtggga tcagaagggt atggacattg cctatgagga    8940
ggcggcctta ggttacaaag agggtggtgt tcctattggc ggatgtctta tcaataacaa    9000
agacggaagt gttctcggtc gtggtcacaa catgagattt caaaagggat ccgccacact    9060
acatggtgag atctccactt tggaaaactg tgggagatta gagggcaaag tgtacaaaga    9120
taccactttg tatacgacgc tgtctccatg cgacatgtgt acaggtgcca tcatcatgta    9180
tggtattcca cgctgtgttg tcggtgagaa cgttaatttc aaaagtaagg gcgagaaata    9240
tttacaaact agaggtcacg aggttgttgt tgttgacgat gagaggtgta aaaagatcat    9300
gaaacaattt atcgatgaaa gacctcagga ttggtttgaa gatattggtg agtaggcggc    9360
cgcgccatag ataaaataaa agatttatt tagtctccag aaaaagggg gaatgaaaga     9420 ccccacctgt aggtttggca agctagctta agtaacgcca ttttgcaagg catggaaaaa    9480
tacataactg agaatagaga agttcagatc aaggtcagga acagatggaa cagctgaata    9540
tgggccaaac aggatatctg tggtaagcag ttcctgcccc ggctcagggc caagaacaga    9600
tggaacagct gaatatgggc caaacaggat atctgtggta agcagttcct gccccggctc    9660
agggccaaga acagatggtc ccagatgcg gtccagccct cagcagtttc tagagaacca     9720
tcagatgttt ccaggtgcc ccaaggacct gaaatgaccc tgtgccttgt ttaaactaac      9780
caatcagttc gcttctcgct tctgttcgcg cgcttctgct ccccgagctc aataaaagag    9840
cccacaaccc ctcactcggg cgccagtcc tccgattgac tgagtcgccc gggtacccgt      9900
gtatccaata aaccctcttg cagttgcatc cgacttgtgg tctcgctgtt ccttgggagg    9960
gtctcctctg agtgattgac tacccgtcag cggggggtctt tcatttgggg gctcgtccgg   10020
gatcgggaga cccctgccca gggaccaccg acccaccacc gggaggtaag ctggctgcct    10080
cgcgcgtttc ggtgatgacg gtgaaaacct ctgacatgtg agcaaaaggc cagcaaaagg    10140
ccaggaaccg taaaaaggcc gcgttgctgg cgttttttcca taggctccgc ccccctgacg   10200
agcatcacaa aaatcgacgc tcaagtcaga ggtggcgaaa cccgacagga ctataaagat    10260
accaggcgtt tcccctgga agctccctcg tgcgctctcc tgttccgacc ctgccgctta     10320
ccggatacct gtccgccttt ctcccttcgg gaagcgtggc gctttctcaa tgctcacgct    10380
gtaggtatct cagttcggtg taggtcgttc gctccaagct gggctgtgtg cacgaaccc    10440
```

```
ccgttcagcc cgaccgctgc gccttatccg gtaactatcg tcttgagtcc aacccggtaa    10500
gacacgactt atcgccactg gcagcagcca ctggtaacag gattagcaga gcgaggtatg    10560
taggcggtgc tacagagttc ttgaagtggt ggcctaacta cggctacact agaaggacag    10620
tatttggtat ctgcgctctg ctgaagccag ttaccttcgg aaaaagagtt ggtagctctt    10680
gatccggcaa acaaaccacc gctggtagcg gtggttttt tgtttgcaag cagcagatta     10740
cgcgcagaaa aaaggatct caagaagatc ctttgatctt ttctacgggg tctgacgctc      10800
agtggaacga aaactcacgt taagggattt tggtcatgag attatcaaaa aggatcttca    10860
cctagatcct tttaaattaa aaatgaagtt ttaaatcaat ctaaagtata tatgagtaaa    10920
cttggtctga cagttaccaa tgcttaatca gtgaggcacc tatctcagcg atctgtctat    10980
ttcgttcatc catagttgcc tgactccccg tcgtgtagat aactacgata cgggagggct    11040
taccatctgg ccccagtgct gcaatgatac cgcgagaccc acgctcaccg gctccagatt    11100
tatcagcaat aaaccagcca gccggaaggg ccgagcgcag aagtggtcct gcaactttat    11160
ccgcctccat ccagtctatt aattgttgcc gggaagctag agtaagtagt tcgccagtta    11220
atagtttgcg caacgttgtt gccattgctg caggcatcgt ggtgtcacgc tcgtcgtttg    11280
gtatggcttc attcagctcc ggttcccaac gatcaaggcg agttacatga tcccccatgt    11340
tgtgcaaaaa agcggttagc tccttcggtc ctccgatcgt tgtcagaagt aagttggccg    11400
cagtgttatc actcatggtt atggcagcac tgcataattc tcttactgtc atgccatccg    11460
taagatgctt ttctgtgact ggtgagtact caaccaagtc attctgagaa tagtgtatgc    11520
ggcgaccgag ttgctcttgc ccggcgtcaa cacgggataa taccgcgcca catagcagaa    11580
ctttaaaagt gctcatcatt ggaaaacgtt cttcggggcg aaaactctca aggatcttac    11640
cgctgttgag atccagttcg atgtaaccca ctcgtgcacc caactgatct tcagcatctt    11700
ttactttcac cagcgtttct gggtgagcaa aaacaggaag gcaaaatgcc gcaaaaaagg    11760
gaataagggc gacacggaaa tgttgaatac tcatactctt cctttttcaa tattattgaa    11820
gcatttatca gggttattgt ctcatgagcg gatacatatt tgaatgtatt tagaaaaata    11880
aacaaatagg ggttccgcgc acatttcccc gaaaagtgcc acctgacgtc taagaaacca    11940
ttattatcat gacattaacc tataaaaata ggcgtatcac gaggcccttt cgtcttcaag    12000
aattcat                                                              12007
```

<210> SEQ ID NO 22
<211> LENGTH: 11893
<212> TYPE: DNA
<213> ORGANISM: Artificial Sequence
<220> FEATURE:
<223> OTHER INFORMATION: RCR Vector - pAC3-yCD2

<400> SEQUENCE: 22

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
```

```
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga daccoctgcc cagggaccac cgacccacca    780 ccggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960 cggggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt tgctttcgg tttgggaccg aagccgcgcc gcgcgtcttg    1140
tctgctgcag catcgttctg tgttgtctct gtctgactgt gtttctgtat ttgtctgaaa    1200
atatgggcca gactgttacc actcccttaa gtttgacctt aggtcactgg aaagatgtcg    1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440 tccctacat cgtgacctgg gaagccttgg cttttgaccc ccctccctgg gtcaagccct    1500
ttgtacaccc taagcctccg cctcctcttc tccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680 aagaccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttcttttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc gggggcaac    2880
```

```
ccgtcacctt cctggtagat actggggccc aacactccgt gctgacccaa aatcctggac      2940
ccctaagtga taagtctgcc tgggtccaag gggctactgg aggaaagcgg tatcgctgga      3000
ccacggatcg caaagtacat ctagctaccg gtaaggtcac ccactctttc ctccatgtac      3060
cagactgtcc ctatcctctg ttaggaagag atttgctgac taaactaaaa gcccaaatcc      3120
actttgaggg atcaggagcc caggttatgg gaccaatggg gcagcccctg caagtgttga      3180
ccctaaatat agaagatgag tatcggctac atgagacctc aaaagagcca gatgtttctc      3240
tagggtccac atggctgtct gattttcctc aggcctgggc ggaaaccggg ggcatgggac      3300
tggcagttcg ccaagctcct ctgatcatac ctctgaaagc aacctctacc cccgtgtcca      3360
taaaacaata ccccatgtca caagaagcca gactggggat caagccccac atacagagac      3420
tgttggacca gggaatactg gtaccctgcc agtcccctg gaacacgccc ctgctacccg      3480
ttaagaaacc agggactaat gattataggc ctgtccagga tctgagagaa gtcaacaagc      3540
gggtggaaga catccacccc accgtgccca acccttacaa cctcttgagc gggctcccac      3600
cgtcccacca gtggtacact gtgcttgatt taaaggatgc cttttctgc ctgagactcc      3660
accccaccag tcagcctctc ttcgcctttg agtggagaga tccagagatg ggaatctcag      3720
gacaattgac ctggaccaga ctcccacagg gtttcaaaaa cagtcccacc ctgtttgatg      3780
aggcactgca cagagaccta gcagacttcc ggatccagca cccagacttg atcctgctac      3840
agtacgtgga tgacttactg ctggccgcca cttctgagct agactgccaa caaggtactc      3900
gggccctgtt acaaaccta gggaacctcg ggtatcgggc ctcggccaag aaagcccaaa      3960
tttgccagaa acaggtcaag tatctggggt atcttctaaa agagggtcag agatggctga      4020
ctgaggccag aaaagagact gtgatggggc agcctactcc gaagacccct cgacaactaa      4080
gggagttcct agggacggca ggcttctgtc gcctctggat ccctgggttt gcagaaatgg      4140
cagccccctt gtaccctctc accaaaacgg ggactctgtt taattgggc ccagaccaac      4200
aaaaggccta tcaagaaatc aagcaagctc ttcctaactgc cccagccctg gggttgccag      4260
atttgactaa gcccttttgaa ctctttgtcg acgagaagca gggctacgcc aaaggtgtcc      4320
taacgcaaaa actgggacct tggcgtcggc cggtggccta cctgtccaaa aagctagacc      4380
cagtagcagc tgggtggccc ccttgcctac ggatggtagc agccattgcc gtactgacaa      4440
aggatgcagg caagctaacc atgggacagc cactagtcat tctggccccc catgcagtag      4500
aggcactagt caaacaaccc cccgaccgct ggctttccaa cgcccggatg actcactatc      4560
aggccttgct tttggacacg gaccgggtcc agttcggacc ggtggtagcc ctgaacccgg      4620
ctacgctgct cccactgcct gaggaagggc tgcaacacaa ctgccttgat atcctggccg      4680
aagcccacgg aacccgaccc gacctaacgg accagccgct cccagacgcc gaccacacct      4740
ggtacacgga tggaagcagt ctcttacaag agggacagcg taaggcggga gctgcggtga      4800
ccaccgagac cgaggtaatc tgggctaaag ccctgccagc cggacatcc gctcagcggg      4860
ctgaactgat agcactcacc caggccctaa agatggcaga aggtaagaag ctaaatgttt      4920
atactgatag ccgttatgct tttgctactg cccatatcca tggagaaata tacagaaggc      4980
gtgggttgct cacatcagaa ggcaaagaga tcaaaaataa agacgagatc ttggccctac      5040
taaaagcccc ctttctgccc aaaagactta gcataatcca ttgtccagga catcaaaagg      5100
gacacagcgc cgaggctaga ggcaaccgga tggctgacca agcggcccga aaggcagcca      5160
tcacagagac tccagacacc tctaccctcc tcatagaaaa ttcatcaccc tacacctcag      5220
aacatttca ttacacagtg actgatataa aggacctaac caagttgggg gccatttatg      5280
```

```
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacctttt tctggctgga    5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt agacggcatc gcagcttgga    6300
tacacgccgc ccacgtgaag gctgccgacc ccggggggtgg accatcctct agactgacat    6360
ggcgcgttca acgctctcaa aaccccctca agataagatt aacccgtgga agcccttaat    6420
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttg acttttacgt gtgccctggg cataccgtaa agtcggggtg    6720
tgggggacca ggagagggct actgtggtaa atggggggtgt gaaaccaccg gacaggctta    6780
ctggaagccc acatcatcgt gggacctaat ctcccttaag cgcggtaaca cccccctggga    6840 cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg gaccccgagt    7080
ccccataggg cccaacccag tattacccga ccaaagactc ccttcctcac caatagagat    7140
tgtaccggct ccacagccac ctagcccccct caataccagt tacccccctt ccactaccag    7200
tacaccctca acctcccta caagtccaag tgtcccacag ccaccccccag gaactggaga    7260 tagactacta gctctagtca aaggagccta tcaggcgctt aacctcacca atccccgacaa    7320 gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
```

```
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat aagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtt actggccgaa   8340
gccgcttgga ataaggccgg tgtgcgtttg tctatatgtt attttccacc atattgccgt   8400
cttttggcaa tgtgagggcc cggaaacctg gccctgtctt cttgacgagc attcctaggg   8460
gtctttcccc tctcgccaaa ggaatgcaag gtctgttgaa tgtcgtgaag gaagcagttc   8520
ctctggaagc ttcttgaaga caaacaacgt ctgtagcgac cctttgcagg cagcggaacc   8580
ccccacctgg cgacaggtgc ctctgcggcc aaaagccacg tgtataagat acacctgcaa   8640
aggcggcaca accccagtgc cacgttgtga gttggatagt tgtggaaaga gtcaaatggc   8700
tctcctcaag cgtattcaac aaggggctga aggatgccca gaaggtaccc cattgtatgg   8760
gatctgatct ggggcctcgg tgcacatgct ttacatgtgt ttagtcgagg ttaaaaaaac   8820
gtctaggccc cccgaaccac ggggacgtgg ttttccttcg aaaaacacga ttataaatgg   8880
tgaccggcgg catggcctcc aagtgggatc aaaagggcat ggatatcgct tacgaggagg   8940
ccctgctggg ctacaaggag ggcggcgtgc ctatcggcgg ctgtctgatc aacaacaagg   9000
acggcagtgt gctgggcagg ggccacaaca tgaggttcca gaagggctcc gccaccctgc   9060
acggcgagat ctccaccctg gagaactgtg gcaggctgga gggcaaggtg tacaaggaca   9120
ccaccctgta caccaccctg tccccttgtg acatgtgtac cggcgctatc atcatgtacg   9180
gcatccctag gtgtgtgatc ggcgagaacg tgaacttcaa gtccaagggc gagaagtacc   9240
tgcaaaccag gggccacgag gtggtggttg ttgacgatga gaggtgtaag aagctgatga   9300
agcagttcat cgacgagagg cctcaggact ggttcgagga tatcggcgag taagcggccg   9360
cagataaaat aaaagatttt atttagtctc cagaaaaagg ggggaatgaa agaccccacc   9420
tgtaggtttg gcaagctagc ttaagtaacg ccattttgca aggcatggaa aaatacataa   9480
ctgagaatag agaagttcag atcaaggtca ggaacagatg aacagctga atatgggcca   9540 aacaggatat ctgtggtaag cagttcctgc cccggctcag gccaagaac agatggaaca   9600 gctgaatatg gccaaacag gatatctgtg gtaagcagtt cctgccccgg ctcagggcca   9660
agaacagatg gtccccagat gcggtccagc cctcagcagt ttctagagaa ccatcagatg   9720
tttccagggt gccccaagga cctgaaatga ccctgtgcct tatttgaact aaccaatcag   9780
ttcgcttctc gcttctgttc gcgcgcttct gctccccgag ctcaataaaa gagcccacaa   9840
cccctcactc ggggcgccag tcctccgatt gactgagtcg cccgggtacc cgtgtatcca   9900
ataaaccctc ttgcagttgc atccgacttg tggtctcgct gttccttggg agggtctcct   9960
ctgagtgatt gactacccgt cagcgggggt ctttcattac atgtgagcaa aaggccagca   10020
aaaggccagg aaccgtaaaa aggccgcgtt gctggcgttt ttccataggc tccgcccccc   10080
```

-continued

```
tgacgagcat cacaaaaatc gacgctcaag tcagaggtgg cgaaacccga caggactata    10140
aagataccag gcgttt cccc ctggaagctc cctcgtgcgc tctcctgttc cgaccctgcc    10200
gcttaccgga tacctgtccg ccttt ctccc ttcgggaagc gtggcgcttt ctcatagctc    10260
acgctgtagg tatctcagtt cggtgtaggt cgttcgctcc aagctgggct gtgtgcacga    10320
accccccgtt cagcccgacc gctgcgcctt atccggtaac tatcgtcttg agtccaaccc    10380
ggtaagacac gacttatcgc cactggcagc agccactggt aacaggatta gcagagcgag    10440
gtatgtaggc ggtgctacag agttcttgaa gtggtggcct aactacggct acactagaag    10500
gacagtattt ggtatctgcg ctctgctgaa gccagttacc ttcggaaaaa gagttggtag    10560
ctcttgatcc ggcaaacaaa ccaccgctgg tagcggtggt ttttttgttt gcaagcagca    10620
gattacgcgc agaaaaaaag gatctcaaga agatcctttg atcttttcta cggggtctga    10680
cgctcagtgg aacgaaaact cacgttaagg gattttggtc atgagattat caaaaaggat    10740
cttcacctag atcctttt aa attaaaaatg aagtttt aaa tcaatctaaa gtatatatga    10800
gtaaacttgg tctgacagtt accaatgctt aatcagtgag gcacctatct cagcgatctg    10860
tctatttcgt tcatccatag ttgcctgact ccccgtcgtg tagataacta cgatacggga    10920
gggcttacca tctggcccca gtgctgcaat gataccgcga ccccacgct caccggctcc    10980 agatttatca gcaataaacc agccagccgg aagggccgag cgcagaagtg gtcctgcaac    11040
tttatccgcc tccatccagt ctattaattg ttgccgggaa gctagagtaa gtagttcgcc    11100
agttaatagt ttgcgcaacg ttgttgccat tgctgcaggc atcgtggtgt cacgctcgtc    11160
gtttggtatg gcttcattca gctccggttc ccaacgatca aggcgagtta catgatcccc    11220
catgttgtgc aaaaaagcgg ttagctcctt cggtcctccg atcgttgtca gaagtaagtt    11280
ggccgcagtg ttatcactca tggttatggc agcactgcat aattctctta ctgtcatgcc    11340
atccgtaaga tgcttttctg tgactggtga gtactcaacc aagtcattct gagaatagtg    11400
tatgcggcga ccgagttgct cttgcccggc gtcaacacgg gataataccg cgccacatag    11460
cagaacttta aaagtgctca tcattggaaa acgttcttcg gggcgaaaac tctcaaggat    11520
cttaccgctg ttgagatcca gttcgatgta acccactcgt gcacccaact gatcttcagc    11580
atcttttact ttcaccagcg tttctgggtg agcaaaaaca ggaaggcaaa atgccgcaaa    11640
aaagggaata agggcgacac ggaaatgttg aatactcata ctcttccttt ttcaatatta    11700
ttgaagcatt tatcagggtt attgtctcat gagcggatac atatttgaat gtatttagaa    11760
aaataaacaa ataggggttc cgcgcacatt tccccgaaaa gtgccacctg acgtctaaga    11820
aaccattatt atcatgacat taacctataa aaataggcgt atcacgaggc cctttcgtct    11880
tcaagaattc cat                                                       11893
```

<210> SEQ ID NO 23
<211> LENGTH: 5
<212> TYPE: PRT
<213> ORGANISM: Artificial Sequence
<220> FEATURE:
<223> OTHER INFORMATION: Peptide linker

<400> SEQUENCE: 23

Gly Gly Gly Gly Ser
1               5

<210> SEQ ID NO 24
<211> LENGTH: 5
<212> TYPE: PRT
<213> ORGANISM: Artificial Sequence

```
<220> FEATURE:
<223> OTHER INFORMATION: Peptide linker

<400> SEQUENCE: 24

Ser Gly Gly Gly Gly
1               5

<210> SEQ ID NO 25
<211> LENGTH: 12
<212> TYPE: PRT
<213> ORGANISM: Artificial Sequence
<220> FEATURE:
<223> OTHER INFORMATION: Peptide linker

<400> SEQUENCE: 25

Gly Lys Ser Ser Gly Ser Gly Ser Glu Ser Lys Ser
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Peptide linker

<400> SEQUENCE: 26

Gly Ser Thr Ser Gly Ser Gly Lys Ser Ser Glu Gly Lys Gly
1               5                   10

<210> SEQ ID NO 27
<211> LENGTH: 18
<212> TYPE: PRT
<213> ORGANISM: Artificial Sequence
<220> FEATURE:
<223> OTHER INFORMATION: Peptide linker

<400> SEQUENCE: 27

Gly Ser Thr Ser Gly Ser Gly Lys Ser Ser Glu Gly Ser Gly Ser Thr
1               5                   10                  15

Lys Gly

<210> SEQ ID NO 28
<211> LENGTH: 18
<212> TYPE: PRT
<213> ORGANISM: Artificial Sequence
<220> FEATURE:
<223> OTHER INFORMATION: Peptide linker

<400> SEQUENCE: 28

Gly Ser Thr Ser Gly Ser Gly Lys Pro Gly Ser Gly Glu Gly Ser Thr
1               5                   10                  15

Lys Gly

<210> SEQ ID NO 29
<211> LENGTH: 14
<212> TYPE: PRT
<213> ORGANISM: Artificial Sequence
<220> FEATURE:
<223> OTHER INFORMATION: Peptide linker

<400> SEQUENCE: 29

Glu Gly Lys Ser Ser Gly Ser Gly Ser Glu Ser Lys Glu Phe
1               5                   10

<210> SEQ ID NO 30
<211> LENGTH: 546
```

```
<212> TYPE: DNA
<213> ORGANISM: Artificial Sequence
<220> FEATURE:
<223> OTHER INFORMATION: Cytosine deaminase coding sequence with cloning
      sites

<400> SEQUENCE: 30
aacacgatta taaatggtga caggggaat ggcaagcaag tgggatcaga agggtatgga      60
cattgcctat gaggaggcgg ccttaggtta caaagagggt ggtgttccta ttggcggatg    120
tcttatcaat aacaaagacg gaagtgttct cggtcgtggt cacaacatga gatttcaaaa    180
gggatccgcc acactacatg gtgagatctc cactttggaa aactgtggga gattagaggg    240
caaagtgtac aaagatacca ctttgtatac gacgctgtct ccatgcgaca tgtgtacagg    300
tgccatcatc atgtatggta ttccacgctg tgttgtcggt gagaacgtta atttcaaaag    360
taagggcgag aaatatttac aaactagagg tcacgaggtt gttgttgttg acgatgagag    420
gtgtaaaaag atcatgaaac aatttatcga tgaaagacct caggattggt ttgaagatat    480
tggtgagtag gcggccgcgc catagataaa ataaagatt ttatttagtc tccagaaaaa     540
gggggg                                                               546

<210> SEQ ID NO 31
<211> LENGTH: 537
<212> TYPE: DNA
<213> ORGANISM: Artificial Sequence
<220> FEATURE:
<223> OTHER INFORMATION: Cytosine deaminase codon optimized with cloning
      site

<400> SEQUENCE: 31
ttataaatgg tgaccggcgg catggcctcc aagtgggatc aaaagggcat ggatatcgct     60
tacgaggagg ccgccctggg ctacaaggag ggcggcgtgc ctatcggcgg ctgtctgatc    120
aacaacaagg acggcagtgt gctgggcagg ggccacaaca tgaggttcca gaagggctcc    180
gccaccctgc acggcgagat ctccaccctg gagaactgtg gcaggctgga gggcaaggtg    240
tacaaggaca ccaccctgta caccaccctg tccccttgtg acatgtgtac cggcgctatc    300
atcatgtacg gcatccctag ggtgtgtggt ggcgagaacg tgaacttcaa gtccaagggc    360
gagaagtacc tgcaaaccag gggccacgag gtggtggttg ttgacgatga gaggtgtaag    420
aagatcatga agcagttcat cgacgagagg cctcaggact ggttcgagga tatcggcgag    480
tgataagcgg ccgcagataa aataaagat tttatttagt ctccagaaaa agggggg        537

<210> SEQ ID NO 32
<211> LENGTH: 40
<212> TYPE: DNA
<213> ORGANISM: Artificial Sequence
<220> FEATURE:
<223> OTHER INFORMATION: Oligonucleotide Primer

<400> SEQUENCE: 32
tcgaggatat cggcgagtga aacccgttat tcttttggc                           40

<210> SEQ ID NO 33
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 33
gccaaaaaga taacgggttt cactcgccg atatcctcga                           40
```

<210> SEQ ID NO 34
<211> LENGTH: 82
<212> TYPE: DNA
<213> ORGANISM: Artificial Sequence
<220> FEATURE:
<223> OTHER INFORMATION: Oligonucleotide Primer

<400> SEQUENCE: 34
tcggcgagtg atccggcggc ggcgcctccg gcggcggcgc ctccggcggc ggcgcctccg    60
gcggcggcgc caacccgtta tt                                            82

<210> SEQ ID NO 35
<211> LENGTH: 82
<212> TYPE: DNA
<213> ORGANISM: Artificial Sequence
<220> FEATURE:
<223> OTHER INFORMATION: Oligonucleotide Primer

<400> SEQUENCE: 35
aataacgggt tggcgccgcc gccggaggcg ccgccgccgg aggcgccgcc gccggaggcg    60
ccgccgccgg atcactcgcc ga                                            82

<210> SEQ ID NO 36
<211> LENGTH: 533
<212> TYPE: DNA
<213> ORGANISM: Artificial Sequence
<220> FEATURE:
<223> OTHER INFORMATION: Cytosine deaminase heat stabilized

<400> SEQUENCE: 36
atggtgacag ggggaatggc aagcaagtgg gatcagaagg gtatggacat tgcctatgag    60
gaggcgttat taggttacaa agagggtggt gttcctattg gcggatgtct tatcaataac   120
aaagacggaa gtgttctcgg tcgtggtcac aacatgagat ttcaaaaggg atccgccaca   180
ctacatggtg agatctccac tttggaaaac tgtgggagat tagagggcaa agtgtacaaa   240
gataccactt tgtatacgac gctgtctcca tgcgacatgt gtacaggtgc catcatcatg   300
tatggtattc cacgctgtgt catcggtgag aacgttaatt tcaaaagtaa gggcgagaaa   360
tatttacaaa ctagaggtca cgaggttgtt gttgttgacg atgagaggtg taaaaagtta   420
atgaaacaat ttatcgatga aagacctcag gattggtttg aagatattgg tgagtaggcg   480
gccgcgccat agataaaata aaagatttta tttagtctcc agaaaagggg ggg          533

<210> SEQ ID NO 37
<211> LENGTH: 480
<212> TYPE: DNA
<213> ORGANISM: Artificial Sequence
<220> FEATURE:
<223> OTHER INFORMATION: CD human codon optimized heat stabilized

<400> SEQUENCE: 37
atggtgaccg gcggcatggc ctccaagtgg gatcaaaagg gcatggatat cgcttacgag    60
gaggccctgc tgggctacaa ggagggcggc gtgcctatcg gcggctgtct gatcaacaac   120
aaggacggca gtgtgctggg cagggggccac aacatgaggt tccagaaggg ctccgccacc   180
ctgcacggcg agatctccac cctggagaac tgtggcaggc tggagggcaa ggtgtacaag   240
gacaccaccc tgtacaccac cctgtcccct tgtgacatgt gtaccggcgc tatcatcatg   300
tacggcatcc ctaggtgtgt gatcggcgag aacgtgaact tcaagtccaa gggcgagaag   360
tacctgcaaa ccaggggcca cgaggtggtg gttgttgacg atgagaggtg taagaagctg   420

```
atgaagcagt tcatcgacga gaggcctcag gactggttcg aggatatcgg cgagtgataa    480
```

<210> SEQ ID NO 38
<211> LENGTH: 546
<212> TYPE: DNA
<213> ORGANISM: Artificial Sequence
<220> FEATURE:
<223> OTHER INFORMATION: CD human codon optimized heat stabilitized cloning sites

<400> SEQUENCE: 38

```
aacacgatta taaatggtga ccggcggcat ggcctccaag tgggatcaaa agggcatgga     60
tatcgcttac gaggaggccc tgctgggcta caaggagggc ggcgtgccta tcggcggctg    120
tctgatcaac aacaaggacg cagtgtgct gggcagggggc cacaacatga ggttccagaa   180
gggctccgcc accctgcacg cgagatctc caccctggag aactgtggca ggctggaggg    240
caaggtgtac aaggacacca ccctgtacac caccctgtcc ccttgtgaca tgtgtaccgg    300
cgctatcatc atgtacggca tccctaggtg tgtgatcggc gagaacgtga acttcaagtc    360
caagggcgag aagtacctgc aaaccagggg ccacgaggtg gtggttgttg acgatgagag    420
gtgtaagaag ctgatgaagc agttcatcga cgagaggcct caggactggt tcgaggatat    480
cggcgagtaa gcggccgcgc catagataaa ataaaagatt ttatttagtc tccagaaaaa    540
gggggg                                                                546
```

<210> SEQ ID NO 39
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 39

```
tcgaggatat cggcgagtga aacccgttat tcttttttggc                           40
```

<210> SEQ ID NO 40
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 40

```
gccaaaaaga taacgggttt cactcgccg atatcctcga                            40
```

<210> SEQ ID NO 41
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 41

```
ccaagctcct atagccgctc actatctact tgggcaataa gaaaaaccga ag              52
```

<210> SEQ ID NO 42
<211> LENGTH: 52
<212> TYPE: DNA
<213> ORGANISM: Artificial Sequence
<220> FEATURE:
<223> OTHER INFORMATION: Oligonucleotide Primer

<400> SEQUENCE: 42

```
ggttcgagga tatcggcgag tgatagatga acccgttatt cttttttggct tc        52
```

<210> SEQ ID NO 43
<211> LENGTH: 1296
<212> TYPE: DNA
<213> ORGANISM: Artificial Sequence
<220> FEATURE:
<223> OTHER INFORMATION: CD codon optimized-UPRT

<400> SEQUENCE: 43

```
aacacgatta taaatggtga ccggcggcat ggcctccaag tgggatcaaa agggcatgga    60
tatcgcttac gaggaggccc tgctgggcta caaggagggc ggcgtgccta tcggcggctg   120
tctgatcaac aacaaggacg cagtgtgct gggcaggggc cacaacatga ggttccagaa   180
gggctccgcc accctgcacg gcgagatctc caccctggag aactgtgca ggctggaggg   240
caaggtgtac aaggacacca ccctgtacac caccctgtcc ccttgtgaca tgtgtaccgg   300
cgctatcatc atgtacggca tccctaggtg tgtgatcggc gagaacgtga acttcaagtc   360
caagggcgag aagtacctgc aaaccagggg ccacgaggtg gtggttgttg acgatgagag   420
gtgtaagaag ctgatgaagc agttcatcga cgagaggcct caggactggt tcgaggatat   480
cggcgagaac ccgttattct ttttggcttc tccattcttg taccttacat atcttatata   540
ttatccaaac aaagggtctt tcgttagcaa acctagaaat ctgcaaaaaa tgtcttcgga   600
accatttaag aacgtctact tgctacctca acaaaccaa ttgctgggtt tgtacaccat   660
catcagaaat aagaatacaa ctagacctga tttcattttc tactccgata gaatcatcag   720
attgttggtt gaagaaggtt tgaaccatct acctgtgcaa aagcaaattg tggaaactga   780
caccaacgaa aacttcgaag gtgtctcatt catgggtaaa atctgtggtg ttttccattgt   840
cagagctggt gaatcgatgg agcaaggatt aagagactgt tgtaggtctg tgcgtatcgg   900
taaaattta attcaaaggg acgaggagac tgctttacca aagttattct acgaaaaatt   960
accagaggat atatctgaaa ggtatgtctt cctattagac ccaatgctgg ccaccggtgg  1020
tagtgctatc atggctacag aagtcttgat taagagaggt gttaagccag agagaattta  1080
cttcttaaac ctaatctgta gtaaggaagg gattgaaaaa taccatgccg ccttcccaga  1140
ggtcagaatt gttactggtg ccctcgacag aggtctagat gaaaacaagt atctagttcc  1200
agggttgggt gactttggtg acagatacta ctgtgtttaa gcggccgcgc catagataaa  1260
ataaaagatt ttatttagtc tccagaaaaa gggggg                             1296
```

<210> SEQ ID NO 44
<211> LENGTH: 82
<212> TYPE: DNA
<213> ORGANISM: Artificial Sequence
<220> FEATURE:
<223> OTHER INFORMATION: Oligonucleotide primer

<400> SEQUENCE: 44

```
tcggcgagtg atccggcggc ggcgcctccg gcggcggcgc ctccggcggc ggcgcctccg    60
gcggcggcgc caacccgtta tt                                             82
```

<210> SEQ ID NO 45
<211> LENGTH: 82
<212> TYPE: DNA
<213> ORGANISM: Artificial Sequence
<220> FEATURE:
<223> OTHER INFORMATION: Oligonucleotide primer

<400> SEQUENCE: 45

```
aataacgggt tggcgccgcc gccggaggcg ccgccgccgg aggcgccgcc gccggaggcg      60
ccgccgccgg atcactcgcc ga                                              82

<210> SEQ ID NO 46
<211> LENGTH: 1356
<212> TYPE: DNA
<213> ORGANISM: Artificial Sequence
<220> FEATURE:
<223> OTHER INFORMATION: CD human codon optimized-linker-UPRT

<400> SEQUENCE: 46
aacacgatta taaatggtga ccggcggcat ggcctccaag tgggatcaaa agggcatgga      60
tatcgcttac gaggaggccc tgctgggcta caaggagggc ggcgtgccta tcggcggctg     120
tctgatcaac aacaaggacg gcagtgtgct gggcaggggc cacaacatga ggttccagaa     180
gggctccgcc accctgcacg gcgagatctc caccctggag aactgtggca ggctggaggg     240
caaggtgtac aaggacacca ccctgtacac caccctgtcc ccttgtgaca tgtgtaccgg     300
cgctatcatc atgtacggca tccctaggtg tgtgatcggc gagaacgtga acttcaagtc     360
caagggcgag aagtacctgc aaaccagggg ccacgaggtg gtggttgttg acgatgagag     420
gtgtaagaag ctgatgaagc agttcatcga cgagaggcct caggactggt tcgaggatat     480
cggcgagtcc ggcggcggcg cctccggcgg cggcgcctcc ggcggcggcg cctccggcgg     540
cggcgccaac ccgttattct ttttggcttc tccattcttg taccttacat atcttatata     600
ttatccaaac aaagggtctt tcgttagcaa acctagaaat ctgcaaaaaa tgtcttcgga     660
accatttaag aacgtctact tgctacctca acaaaccaa ttgctgggtt tgtacaccat      720
catcagaaat aagaatacaa ctagacctga tttcattttc tactccgata gaatcatcag     780
attgttggtt gaagaaggtt tgaaccatct acctgtgcaa aagcaaattg tggaaactga     840
caccaacgaa aacttcgaag tgtctcatt catgggtaaa atctgtggtg tttccattgt      900
cagagctggt gaatcgatgg agcaaggatt aagagactgt tgtaggtctg tgcgtatcgg     960
taaaatttta attcaaaggg acgaggagac tgctttacca aagttattct acgaaaaatt    1020
accagaggat atatctgaaa ggtatgtctt cctattagac ccaatgctgg ccaccggtgg    1080
tagtgctatc atggctacag aagtcttgat taagagaggt gttaagccag agagaattta    1140
cttcttaaac ctaatctgta gtaaggaagg gattgaaaaa taccatgccg ccttcccaga    1200
ggtcagaatt gttactggtg ccctcgacag aggtctagat gaaaacaagt atctagttcc    1260
agggttgggt gactttggtg acagatacta ctgtgtttaa gcggccgcgc catagataaa    1320
ataaaagatt ttatttagtc tccagaaaaa gggggg                              1356

<210> SEQ ID NO 47
<211> LENGTH: 1269
<212> TYPE: DNA
<213> ORGANISM: Artificial Sequence
<220> FEATURE:
<223> OTHER INFORMATION: CD human codon optimized-OPRT

<400> SEQUENCE: 47
aacacgatta taaatggtga ccggcggcat ggcctccaag tgggatcaaa agggcatgga      60
tatcgcttac gaggaggccc tgctgggcta caaggagggc ggcgtgccta tcggcggctg     120
tctgatcaac aacaaggacg gcagtgtgct gggcaggggc cacaacatga ggttccagaa     180
gggctccgcc accctgcacg gcgagatctc caccctggag aactgtggca ggctggaggg     240
caaggtgtac aaggacacca ccctgtacac caccctgtcc ccttgtgaca tgtgtaccgg     300
```

```
cgctatcatc atgtacggca tccctaggtg tgtgatcggc gagaacgtga acttcaagtc    360
caagggcgag aagtacctgc aaaccagggg ccacgaggtg gtggttgttg acgatgagag    420
gtgtaagaag ctgatgaagc agttcatcga cgagaggcct caggactggt tcgaggatat    480
cggcgaggcg gtcgctcgtg cagctttggg gccattggtg acgggtctgt acgacgtgca    540
ggctttcaag tttggggact tcgtgctgaa gagcgggctt cctccccca tctacatcga    600 tctgcggggc atcgtgtctc gaccgcgtct tctgagtcag gttgcagata ttttattcca    660
aactgcccaa aatgcaggca tcagttttga caccgtgtgt ggagtgcctt atacagcttt    720
gccattggct acagttatct gttcaaccaa tcaaattcca atgcttatta aaggaaaga     780 aacaaaggat tatggaacta agcgtcttgt agaaggaact attaatccag agaaacctg     840 tttaatcatt gaagatgttg tcaccagtgg atctagtgtt ttggaaactg ttgaggttct    900
tcagaaggag ggcttgaagg tcactgatgc catagtgctg ttggacagag agcagggagg    960
caaggacaag ttgcaggcgc acgggatccg cctccactca gtgtgtacat tgtccaaaat   1020
gctggagatt ctcgagcagc agaaaaaagt tgatgctgag acagttggga gagtgaagag   1080
gtttattcag gagaatgtct ttgtggcagc gaatcataat ggttctcccc tttctataaa   1140
ggaagcaccc aaagaactca gcttcggtgc acgtgcagag ctgcccagga tccacccagt   1200
tgcatcgaag taagcggccg cgccatagat aaaataaaag attttattta gtctccagaa   1260
aaaggggg                                                           1269

<210> SEQ ID NO 48
<211> LENGTH: 1329
<212> TYPE: DNA
<213> ORGANISM: Artificial Sequence
<220> FEATURE:
<223> OTHER INFORMATION: CD codon optimized-linker-OPRT

<400> SEQUENCE: 48
aacacgatta taaatggtga ccggcggcat ggcctccaag tgggatcaaa agggcatgga     60
tatcgcttac gaggaggccc tgctgggcta caaggagggc ggcgtgccta tcggcggctg    120
tctgatcaac aacaaggacg gcagtgtgct gggcaggggc cacaacatga ggttccagaa    180
gggctccgcc accctgcacg gcgagatctc caccctggag aactgtggca ggctggaggg    240
caaggtgtac aaggacacca ccctgtacac caccctgtcc ccttgtgaca tgtgtaccgg    300
cgctatcatc atgtacggca tccctaggtg tgtgatcggc gagaacgtga acttcaagtc    360
caagggcgag aagtacctgc aaaccagggg ccacgaggtg gtggttgttg acgatgagag    420
gtgtaagaag ctgatgaagc agttcatcga cgagaggcct caggactggt tcgaggatat    480
cggcgagtcc ggcggcggcg cctccggcgg cggcgcctcc ggcggcggcg cctccggcgg    540
cggcgccgcg gtcgctcgtg cagctttggg gccattggtg acgggtctgt acgacgtgca    600
ggctttcaag tttggggact tcgtgctgaa gagcgggctt cctccccca tctacatcga    660 tctgcggggc atcgtgtctc gaccgcgtct tctgagtcag gttgcagata ttttattcca    720
aactgcccaa aatgcaggca tcagttttga caccgtgtgt ggagtgcctt atacagcttt    780
gccattggct acagttatct gttcaaccaa tcaaattcca atgcttatta aaggaaaga    840 aacaaaggat tatggaacta agcgtcttgt agaaggaact attaatccag agaaacctg    900 tttaatcatt gaagatgttg tcaccagtgg atctagtgtt ttggaaactg ttgaggttct    960
tcagaaggag ggcttgaagg tcactgatgc catagtgctg ttggacagag agcagggagg   1020
caaggacaag ttgcaggcgc acgggatccg cctccactca gtgtgtacat tgtccaaaat   1080
```

-continued

```
gctggagatt ctcgagcagc agaaaaaagt tgatgctgag acagttggga gagtgaagag    1140
gtttattcag gagaatgtct ttgtggcagc gaatcataat ggttctcccc tttctataaa    1200
ggaagcaccc aaagaactca gcttcggtgc acgtgcagag ctgcccagga tccacccagt    1260
tgcatcgaag taagcggccg cgccatagat aaaataaaag attttattta gtctccagaa    1320
aaaggggggg                                                           1329
```

<210> SEQ ID NO 49
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 49
atcatcatgt acggcatccc tag                                            23

<210> SEQ ID NO 50
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 50
tgaactgctt catcagcttc ttac                                           24

<210> SEQ ID NO 51
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 51
tcatcgtcaa caaccaccac ctcgt                                          25

<210> SEQ ID NO 52
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 52
aacctcaacc tcccctacaa gt                                             22

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 53
gttaagcgcc tgataggctc                                                20

<210> SEQ ID NO 54
<211> LENGTH: 26
<212> TYPE: DNA
<213> ORGANISM: Artificial Sequence
<220> FEATURE:
<223> OTHER INFORMATION: Oligonucleotide Primer

```
<400> SEQUENCE: 54
agccaccccc aggaactgga gataga                                            26
```

US 8,722,867 B2

GENE THERAPY VECTORS AND CYTOSINE DEAMINASES

CROSS REFERENCE TO RELATED APPLICATIONS

This application is a continuation-in-part of International Application No. PCT/US09/58510, filed Sep. 26, 2009, which application claims priority to U.S. Provisional Application Ser. No. 61/100,666, filed Sep. 26, 2008, U.S. Provisional Application Ser. No. 61/120,618, filed Dec. 8, 2008, and U.S. Provisional Application Ser. No. 61/186,823, filed Jun. 13, 2009, and further claims priority to U.S. Provisional Application Ser. No. 61/318,728, filed Mar. 29, 2010 the disclosures of which are incorporated herein by reference.

TECHNICAL FIELD

This disclosure relates to modified cytosine deaminases (CDs). The disclosure further relates to cells expressing such modified CDs and methods of using such modified CDs in the treatment of disease and disorders.

BACKGROUND

The yeast, or bacterial, cytosine deaminase converts the innocuous antibiotic pro-drug 5-FC into the cytotoxic chemotherapeutic agent 5-fluorouracil (5-FU). Humans (and mammals in general) are not known to possess a naturally occurring gene encoding an enzyme with significant cytosine deaminase activity. Yeast and bacterial cytosine deaminase have gained recognition in the treatment of cancers using gene delivery and viral vectors for the delivery of the enzyme followed by treatment with 5-FC, which is then converted by the enzyme to a cytotoxic drug (Miller et al., Can Res 62:773-780 2002; Kievit et al., Can Res 59:1417-1421 1999).

SUMMARY

Provided herein are polypeptides that convert 5-FC to 5-FU. Also provided are nucleic acid molecules that encode such polypeptides, cells expressing such polypeptides, vectors containing such polynucleotide and polypeptides and methods of synthesizing 5-FU or derivatives thereof from a suitable using such polypeptides. Accordingly, in various embodiments, isolated or recombinant polypeptides comprising a cytosine deaminase having a sequence as set forth in SEQ ID NO: 2 is provided. In other embodiments, the polypeptide comprises SEQ ID NO: 2 with a mutation selected from the group consisting of A23L, V108I, I140L and any combination thereof. In yet another embodiment, the polypeptide comprises the sequence as set forth in SEQ ID NO: 4 and includes up to 50, 25, 10, or 5 conservative amino acid substitutions excluding residues: (a) 23, 108 and 140. In general, polypeptides provided herein display cytosine deaminase activity useful for converting 5-FC to 5-FU.

The disclosure also provides polypeptide that comprises a sequence that is at least 80%, 90%, 95%, 98% or 99% identical to SEQ ID NO: 4, wherein the polypeptide has a leucine at position 23, an isoleucine at position 108 and a leucine at position 140, and wherein the polypeptide has cytosine deaminase activity. In yet another embodiment, the polypeptide comprises the sequence as set forth in SEQ ID NO: 4.

The disclosure further provides fusion constructs comprising any one of the foregoing polypeptides operably linked to a uracil phosphoribosyltransferase (UPRT) or an orotate phosphoribosyltransferase (OPRT). In one embodiment, the fusion construct comprises a first polypeptide comprising SEQ ID NO: 2 with a mutation selected from the group consisting of A23L, V108I, I140L and any combination thereof linked to a second polypeptide having UPRT or OPRT activity. In yet another embodiment, the fusion construct comprises a first polypeptide having the sequence as set forth in SEQ ID NO:4 and includes up to 50, 25, 10, or 5 conservative amino acid substitutions excluding residues: 23, 108 and 140 wherein the first polypeptide is linked to a second polypeptide having UPRT or OPRT activity. The disclosure also provides a fusion construct comprising a first polypeptide having cytosine deaminase activity and that comprise a sequence that is at least 80%, 90%, 95%, 98% or 99% identical to SEQ ID NO: 4, wherein the polypeptide has a leucine at position 23, an isoleucine at position 108 and a leucine at position 140, and wherein the first polypeptide is linked to a second polypeptide comprising UPRT or OPRT activity. In one embodiment, the polypeptides having UPRT or OPRT activity comprises a sequence as set forth in SEQ ID NO: 8 and 10, respectively, or variants thereof. In yet another embodiment, a first polypeptide comprising cytosine deaminase activity is linked to a polypeptide having UPRT or OPRT activity, wherein the polypeptides are separated by a peptide linker. In another embodiment, the fusion construct comprises a sequence selected from the group consisting of SEQ ID NO: 12, 14, 16 or 18.

The disclosure further provides polynucleotides encoding any of the foregoing polypeptides. For example, the disclosure provides a polynucleotide encoding a polypeptide comprising SEQ ID NO: 2 with a mutation selected from the group consisting of A23L, V108I, I140L and any combination thereof. In yet another embodiment, the polynucleotide encodes a polypeptide comprising a sequence as set forth in SEQ ID NO:4 and includes up to 50, 25, 10, or 5 conservative amino acid substitutions excluding residues: (a) 23, 108 and 140. In a further embodiment, the disclosure provides a polynucleotide encoding a polypeptide comprising a sequence that is at least 80%, 90%, 95%, 98% or 99% identical to SEQ ID NO: 4, wherein the polypeptide has a leucine at position 23, an isoleucine at position 108 and a leucine at position 140, and wherein the polypeptide has cytosine deaminase activity. In yet another embodiment, the polynucleotide encodes a polypeptide comprising SEQ ID NO: 4. In a further embodiment, the polynucleotide encodes a polypeptide comprising a sequence as set forth in SEQ ID NO: 4, 6, 8, 10, 11, 12, or 13.

The disclosure provides a human codon optimized polynucleotide encoding a cytosine deaminase. In one embodiment, the human codon optimized polynucleotide comprises a sequence as set forth in SEQ ID NO: 3. In yet another embodiment, the polynucleotide comprises a sequence as set forth in SEQ ID NO:5, 7, or 9.

In other embodiments, a cytosine deaminase or fusion construct of the disclosure is delivered using a gene delivery system (GDS). In another aspect, the polynucleotide encoding a cytosine deaminase is delivered with a GDS that is a viral or viral derived vector. The viral vector can be replicating or non-replicating, and can be an adenoviral vector, a measles vector, a herpes vector, a retroviral vector (including a lentiviral vector), a rhabdoviral vector such as a Vesicular Stomatitis viral vector, a reovirus vector, a Seneca Valley Virus vector, a poxvirus vector (including animal pox or vaccinia derived vectors), a parvovirus vector (including an AAV vector), an alphavirus vector or other viral vector known to one skilled in the art. In one embodiment, the viral vector can be a replication competent retroviral vector capable of infecting replicating mammalian cells. The replication competent retroviral vector can comprise an Orthoretrovirus or more typically a gamma retrovirus vector. In one aspect, a replication competent retroviral vector comprises an internal ribosomal entry site (IRES) 5' to the polynucleotide encoding a cytosine deaminase of the disclosure. In one embodiment, the polynucleotide encoding a cytosine deaminase is 3' to a ENV polynucleotide of a retroviral vector.

In other embodiments, host cells transfected with a cytosine deaminase or fusion construct of the disclosure, or a vector that includes a polynucleotide or fusion construct of the disclosure, are provided. Host cells include eukaryotic cells such as yeast cells, insect cells, or animal cells. Host cells also include procaryotic cells such as bacterial cells.

The disclosure also provides methods of treating a cell proliferative disorder including a cancer comprising administering a polynucleotide or polypeptide of the disclosure to a subject and contacting the subject with a cytotoxic drug comprising 5-fluorocytosine (5-FC).

The disclosure provides a recombinant replication competent retrovirus (RCR) comprising: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a cassette comprising an internal ribosome entry site (IRES) operably linked to a heterologous polynucleotide, wherein the cassette is positioned 5' to the 3' LTR and 3' to the env nucleic acid domain encoding the retroviral envelope; and cis-acting sequences necessary for reverse transcription, packaging and integration in a target cell, wherein the RCR maintains higher replication competency after 6 passages compared to a pACE vector (SEQ ID NO:21). In one embodiment, the retroviral polynucleotide sequence is derived from murine leukemia virus (MLV), Moloney murine leukemia virus (MoMLV), Feline leukemia virus or Gibbon ape leukemia virus (GALV). In another embodiment, the MLV is an amphotropic MLV. In yet another embodiment, the retrovirus is an oncoretrovirus. In yet another embodiment, the target cell is a cell having a cell proliferative disorder. The cell proliferative disorder can be selected from the group consisting of, but is not limited to, lung cancer, colon-rectum cancer, breast cancer, prostate cancer, urinary tract cancer, uterine cancer, brain cancer, head and neck cancer, pancreatic cancer, melanoma, stomach cancer and ovarian cancer, rheumatoid arthritis and other autoimmune diseases. In one embodiment, the promoter comprises a CMV promoter having a sequence as set forth in SEQ ID NO:19, 20, or 22 from nucleotide 1 to about nucleotide 582 and may include modification to one or more nucleic acid bases and which is capable of directing and initiating transcription. In yet a further embodiment, the promoter comprises a sequence as set forth in SEQ ID NO:19, 20, or 22 from nucleotide 1 to about nucleotide 582. In a further embodiment, the promoter comprises a CMV-R-U5 domain polynucleotide. In one embodiment, the CMV-R-U5 domain comprises the immediately early promoter from human cytomegalovirus linked to an MLV R-U5 region. In yet another embodiment, the CMV-R-U5 domain polynucleotide comprises a sequence as set forth in SEQ ID NO:19, 20, or 22 from about nucleotide 1 to about nucleotide 1202 or sequences that are at least 95% identical to a sequence as set forth in SEQ ID NO:19, 20, or 22, wherein the polynucleotide promotes transcription of a nucleic acid molecule operably linked thereto. In another embodiment, the gag and pol of the polynucleotide are derived from an oncoretrovirus. The gag nucleic acid domain can comprise a sequence from about nucleotide number 1203 to about nucleotide 2819 of SEQ ID NO: 19 or a sequence having at least 95%, 98%, 99% or 99.8% identity thereto. The pol domain can comprise a sequence from about nucleotide number 2820 to about nucleotide 6358 of SEQ ID NO:19 or a sequence having at least 95%, 98%, 99% or 99.9% identity thereto. In one embodiment, the env domain encodes an amphoteric env protein. The env domain can comprise a sequence from about nucleotide number 6359 to about nucleotide 8323 of SEQ ID NO:19 or a sequence having at least 95%, 98%, 99% or 99.8% identity thereto. The IRES domain of the vector can be any IRES, however, in one embodiment the IRES is derived from an encephalomyocarditis virus. In a further embodiment, the IRES comprises a sequence from about nucleotide number 8327 to about nucleotide 8876 of SEQ ID NO:19 or a sequence having at least 95%, 98%, or 99% identity thereto. In yet a further embodiment, the heterologous polynucleotide comprises a polynucleotide having a sequence as set forth in SEQ ID NO:3, 5, 11, 13, 15 or 17. In a further embodiment, the heterologous sequence encodes a polypeptide comprising a sequence as set forth in SEQ ID NO:4. The heterologous nucleic acid is human codon optimized and encodes a polypeptide as set forth in SEQ ID NO:4. In a further embodiment, the heterologous nucleic acid comprises a sequence as set forth in SEQ ID NO: 19 from about nucleotide number 8877 to about 9353. In one embodiment, the 3' LTR is derived from an oncoretrovirus. In a further embodiment, the 3' LTR comprises a U3-R-U5 domain. In yet a further embodiment, the 3' LTR comprises a sequence as set forth in SEQ ID NO:19 from about nucleotide 9405 to about 9998 or a sequence that is at least 95%, 98% or 99.5% identical thereto.

The disclosure provides a polynucleotide comprising a sequence as set forth in SEQ ID NO:19, 20, or 22.

The disclosure provides an isolated polynucleotide comprising from 5' to 3': a CMV-R-U5 fusion of the immediate early promoter from human cytomegalovirus to an MLV R-U5 region; a PBS, primer binding site for reverse transcriptase; a 5' splice site; ψ packaging signal; a gag coding sequence for MLV group specific antigen; a pol coding sequence for MLV polymerase polyprotein; a 3' splice site; a 4070A env coding sequence for envelope protein of MLV strain 4070A; an internal ribosome entry site (IRES) from encephalomyocarditis virus; a modified cytosine deaminase coding sequence; a polypurine tract; and a U3-R-U5 MLV long terminal repeat.

The disclosure provides a method of treating a subject with a cell proliferative disorder comprising contacting the subject with a polynucleotide a polypeptide of the disclosure having cytosine deaminase activity under conditions such that the polynucleotide is expressed and contacting the subject with 5-fluorocytosine.

The disclosure also provides a method of treating a cell proliferative disorder in a subject comprising contacting the subject with a retrovirus of the disclosure, wherein the heterologous nucleic acid sequence encodes a therapeutic protein that inhibits proliferation of a neoplastic cell. In one embodiment, the retrovirus comprises a polynucleotide encoding a polypeptide having a sequence as set forth in SEQ ID NO:4, 12, 14, 16, or 18.

The disclosure provides a recombinant replication competent retrovirus (RCR) comprising recombinant replication competent retrovirus, wherein the vector infects the target multiple times leading to a mean of 5 or more copies of the retrovirus genome. The multiple copies provide a "super" infection useful for gene delivery and protein production in vivo and in vitro. In one embodiment, the recombinant replication competent retrovirus (RCR) comprises: a retroviral GAG protein; a retroviral POL protein; a retroviral envelope; a retroviral polynucleotide comprising Long-Terminal Repeat (LTR) sequences at the 3' end of the retroviral polynucleotide, a promoter sequence at the 5' end of the retroviral polynucleotide, said promoter being suitable for expression in a mammalian cell, a gag nucleic acid domain, a pol nucleic acid domain and an env nucleic acid domain; a cassette comprising an internal ribosome entry site (IRES) operably linked to a cytosine deaminase polynucleotide of the disclosure, wherein the cassette is positioned 5' to the 3' LTR and 3' to the env nucleic acid domain encoding the retroviral envelope; and cis-acting sequences necessary for reverse transcription, packaging and integration in a target cell, wherein the RCR maintains higher replication competency after 6 passages compared to a pACE vector (SEQ ID NO:21). In one embodiment, the retroviral polynucleotide sequence is derived from murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus (XMRV), avian reticuloendotheliosis virus (REV), or Gibbon ape leukemia virus (GALV). In another embodiment, the MLV is an amphotropic MLV. In yet another embodiment, the retrovirus is an oncoretrovirus or gamma retrovirus. In yet another embodiment, the target cell is a cell having a cell proliferative disorder. The cell proliferative disorder can be selected from the group consisting of, but is not limited to, lung cancer, colon-rectum cancer, breast cancer, prostate cancer, urinary tract cancer, uterine cancer, brain cancer, head and neck cancer, pancreatic cancer, melanoma, stomach cancer and ovarian cancer, rheumatoid arthritis and other autoimmune diseases. In one embodiment, the promoter comprises a CMV promoter having a sequence as set forth in SEQ ID NO:19, 20 or 22 from nucleotide 1 to about nucleotide 582 and may include modification to one or more nucleic acid bases and which is capable of directing and initiating transcription. In yet a further embodiment, the promoter comprises a sequence as set forth in SEQ ID NO:19, 20 or 22 from nucleotide 1 to about nucleotide 582. In a further embodiment, the promoter comprises a CMV-R-U5 domain polynucleotide. In one embodiment, the CMV-R-U5 domain comprises the immediately early promoter from human cytomegalovirus linked to an MLV R-U5 region. In yet another embodiment, the CMV-R-U5 domain polynucleotide comprises a sequence as set forth in SEQ ID NO:19, 20 or 22 from about nucleotide 1 to about nucleotide 1202 or sequences that are at least 95% identical to a sequence as set forth in SEQ ID NO:19, 20 or 22, wherein the polynucleotide promotes transcription of a nucleic acid molecule operably linked thereto. In another embodiment, the gag and pol of the polynucleotide are derived from an oncoretrovirus or gamma retrovirus. The gag nucleic acid domain can comprise a sequence from about nucleotide number 1203 to about nucleotide 2819 of SEQ ID NO: 19 or 22 or a sequence having at least 95%, 98%, 99% or 99.8% identity thereto. The pol domain can comprise a sequence from about nucleotide number 2820 to about nucleotide 6358 of SEQ ID NO:19 or 22 or a sequence having at least 95%, 98%, 99% or 99.9% identity thereto. In one embodiment, the env domain encodes an amphotropic env protein. The env domain can comprise a sequence from about nucleotide number 6359 to about nucleotide 8323 of SEQ ID NO:19 or 22 or a sequence having at least 95%, 98%, 99% or 99.8% identity thereto. The IRES domain of the vector can be any IRES, however, in one embodiment the IRES is derived from an encephalomyocarditis virus. In a further embodiment, the IRES comprises a sequence from about nucleotide number 8327 to about nucleotide 8876 of SEQ ID NO:19 or 22 or a sequence having at least 95%, 98%, or 99% identity thereto.

The disclosure provides a method of treating a cell proliferative disorder in a subject comprising contacting the subject with a retrovirus of the disclosure wherein the vector infects the target multiple times leading to a mean of 5 or more copies of the retrovirus genome.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 1A-D shows (A) a schematic of a recombinant retroviral vector of the disclosure; (B and C) a plasmid map of a polynucleotide of the disclosure; (D) a sequence of a polynucleotide of the disclosure (SEQ ID NO:19) in various formats.

FIG. 2A-D shows schemes for the generation of various embodiments of the disclosure comprising polypeptides with CD, OPRT and UPRT activity.

Like reference symbols in the various drawings indicate like elements.

DETAILED DESCRIPTION

Figure 1A:
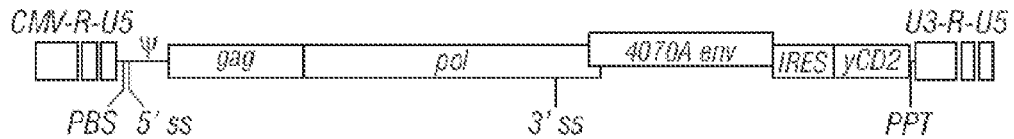

As used herein and in the appended claims, the singular forms "a," "and," and "the" include plural referents unless the context clearly dictates otherwise. Thus, for example, reference to "a cell" includes a plurality of such cells and reference to "the agent" includes reference to one or more agents known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

A cytosine deaminase (EC 3.5.4.1) is an enzyme that catalyzes the chemical reaction

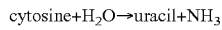

Thus, the two substrates of this enzyme are cytosine and $H_2O$, whereas its two products are uracil and $NH_3$. This enzyme belongs to the family of hydrolases, those acting on carbon-nitrogen bonds other than peptide bonds, specifically in cyclic amidines. The systematic name of this enzyme class is cytosine aminohydrolase. This enzyme is also called isocytosine deaminase. This enzyme participates in pyrimidine metabolism.

More particularly, cytosine deaminase is an enzyme involved in the metabolic pathway for pyrimidines, through which exogenous cytosine is transformed, via hydrolytic deamination, into uracil. Cytosine deaminase (CDase or CD) activities have been demonstrated in prokaryotes and lower eukaryotes, but they are absent in mammals (Koechlin et al., 1966, Biochem. Pharmacol. 15, 435-446; Polak et al., 1976, Chemotherapy 22, 137-153). The FCY1 gene of *Saccharomyces cerevisiae* (*S. cerevisiae*) and the coda gene of *E. coli*, which encode, respectively, the CDase of these two organisms, are known and their sequences are published (EP 402 108; Erbs et al., 1997, Curr. Genet. 31, 1-6; WO 93/01281). CDase also deaminates a cytosine analogue, 5-fluorocytosine (5-FC) to 5-fluorouracil (5-FU), which is a highly cytotoxic compound, in particular when it is converted to 5-fluoro-UMP (5-FUMP). Cells which lack CDase activity, due either to an inactivating mutation of the gene encoding the enzyme or to their natural deficiency for this enzyme (for example mammalian cells) are resistant to 5-FC (Jund and Lacroute, 1970, J. Bacteriol. 102, 607-615; Kilstrup et al., 1989, J. Bacteriol., 171, 2124-2127). On the other hand, it has been demonstrated that it is possible to transmit 5-FC sensitivity to mammalian cells into which the sequence encoding a CDase activity has been transferred (Huber et al., 1993, Cancer Res. 53, 4619-4626; Mullen et al., 1992, Proc. Natl. Acad. Sci. USA 89, 33-37; WO 93/01281). Accordingly, the use of CD is advantageous in the context of gene therapy, in particular anticancer gene therapy.

However, 5-FC sensitivity varies a great deal depending on the cell lines. Low sensitivity is observed, for example, in PANC-1 (carcinoma of the pancreas) and SK-BR-3 (breast adenocarcinoma) human tumor lines transduced with a retrovirus expressing the coda gene of *E. coli* (Harris et al., 1994, Gene Therapy 1, 170-175). This phenomenon is explained by the absence or poor endogenous conversion of the 5-FU formed by the enzymatic action of the CDase, to cytotoxic 5-FUMP. This step, which is normally carried out in mammalian cells by orotate phosphorybosyltransferase (OPRTase), may be absent in certain tumors and thus make gene therapy based on CDase ineffective. In prokaryotes and lower eukaryotes, uracil is transformed into UMP through the action of uracil phosphoribosyltransferase (UPRTase activity). This enzyme also converts 5-FU to 5-FUMP. Importantly, bacterial uracil phosphoribosyltransferase (UPRT) is functionally equivalent to orotate phosphoribosyltransferase (OPRT) or uridine-5'-monophosphate synthase of mammalian cells. These enzymes mediate the conversion of 5-fluorouracil (5-FU) (a fluorinated analog of uracil) to 5-fluorouridine 5' monophosphate (5-FUMP). 5-fluorouridine 5' monophosphate is subsequently converted to 5-FdUDP and FdUTP via the mammalian de novo pyrimidine pathway. Each 5-FdUTP is an irreversible inhibitor of thymidylate synthase (Thy-A) and results in dTTP starvation. It is widely accepted that this conversion is one of the requisite pathways to achieve cytotoxic effects of 5-fluorouracil and that bacterially uracil phosphoribosyltransferase of bacterial origin is able to convert 5-fluorouracil to the same active metabolite as does mammalian orotate phosphoribosyltransferase. In the absence of UPRTase activity or OPRTase activity, the 5-FU, originating from the deamination of the 5-FC by the CDase, is not transformed into cytotoxic 5-FUMP (Jund and Lacroute, 1970, J. Bacteriol. 102, 607-615).

As described herein, the disclosure provides polynucleotides encoding polypeptides and polypeptides comprising a fusion of a first polypeptide having cytosine deaminase activity and a second polypeptide comprising UPRT or OPRT activity. Such fusion constructs are useful for converting uracil, or a derivative thereof, into a monophosphate analogue, and in particular 5-FU into 5-FUMP.

As will be described in more detail below, the disclosure is based, at least in part, on the generation and expression of novel polypeptides that catalyze the conversion 5-FC to 5-FU. In one embodiment, novel polypeptides that have been engineered to have improved catalytic properties for the conversion of 5-FC to 5-FU are provided. Such polypeptides include variants that have been altered to include amino acid substitutions at specified residues. While these variants will be described in more detail below, it is understood that polypeptides of the disclosure may contain one or more modified amino acids. The presence of modified amino acids may be advantageous in, for example, (a) increasing polypeptide in vivo half-life, (b) reducing or increasing polypeptide antigenicity, and (c) increasing polypeptide storage stability. Amino acid(s) are modified, for example, co-translationally or post-translationally during recombinant production (e.g., N-linked glycosylation at N—X—S/T motifs during expression in mammalian cells) or modified by synthetic means. Accordingly, A "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

Recombinant methods for producing, isolating, and using the modified CD polypeptides and polynucleotides of the disclosure are described herein. In addition to recombinant production, the polypeptides may be produced by direct peptide synthesis using solid-phase techniques (e.g., Stewart et al. (1969) Solid-Phase Peptide Synthesis (WH Freeman Co, San Francisco); and Merrifield (1963) J. Am. Chem. Soc. 85: 2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer.

By way of illustration, the nucleic acid sequences encoding the UPRTases of *E. coli* (Anderson et al., 1992, Eur. J. Biochem 204, 51-56), of *Lactococcus lactis* (Martinussen and Hammer, 1994, J. Bacteriol. 176, 6457-6463), of *Mycobacterium bovis* (Kim et al., 1997, Biochem Mol. Biol. Int 41, 1117-1124) and of *Bacillus subtilis* (Martinussen et al., 1995, J. Bacteriol. 177, 271-274) can be used in the context of the disclosure. However, use of a yeast UPRTase, and in particular that encoded by the FUR1 gene of *S. cerevisiae*, the sequence of which disclosed in Kern et al. (1990, Gene 88, 149-157) is incorporated herein of reference. By way of indication, the sequences of the genes and those of the corresponding UPRTases can be found in the literature and the specialized data banks (SWISSPROT, EMBL, Genbank Medline, etc.).

A "protein" or "polypeptide", which terms are used interchangeably herein, comprises one or more chains of chemical building blocks called amino acids that are linked together by chemical bonds called peptide bonds. An "enzyme" means any substance, preferably composed wholly or largely of protein, that catalyzes or promotes, more or less specifically, one or more chemical or biochemical reactions. The term "enzyme" can also refer to a catalytic polynucleotide (e.g., RNA or DNA). A "native" or "wild-type" protein, enzyme, polynucleotide, gene, or cell, means a protein, enzyme, polynucleotide, gene, or cell that occurs in nature.

Accordingly, in various embodiments, isolated or recombinant polypeptides comprising SEQ ID NO:2 with a mutation selected from the group consisting of A23L, V108I, I140L and any combination thereof are provided. In yet another embodiment, the polypeptide comprises the sequence as set forth in SEQ ID NO:4 and includes up to 50, 25, 10, or 5 conservative amino acid substitutions excluding residues: (a) 23, 108 and 140. In general, polypeptides provided herein display cytosine deaminase activity useful for converting 5-FC to 5-FU.

The disclosure also provides polypeptides that comprise a sequence that is at least 80%, 90%, 95%, 98% or 99% identical to SEQ ID NO:4, wherein the polypeptide has a leucine at position 23, an isoleucine at position 108 and a leucine at position 140, and wherein the polypeptide has cytosine deaminase activity. In yet another embodiment, the polypeptide comprises the sequence as set forth in SEQ ID NO:4.

The disclosure further provides fusion constructs comprising any one of the foregoing polypeptides operably linked to a uracil phosphoribosyltransferase (UPRT) or an orotate phosphoribosyltransferase (OPRT). In one embodiment, the fusion construct comprises a first polypeptide comprising SEQ ID NO:2 with a mutation selected from the group consisting of A23L, V108I, I140L and any combination thereof linked to a second polypeptide having UPRT or OPRT activity. In yet another embodiment, the fusion construct comprises a first polypeptide having the sequence as set forth in SEQ ID NO:4 and includes up to 50, 25, 10, or 5 conservative amino acid substitutions excluding residues: 23, 108 and 140 wherein the first polypeptide is linked to a second polypeptide having UPRT or OPRT activity. The disclosure also provides a fusion construct comprising a first polypeptide having cytosine deaminase activity and that comprise a sequence that is at least 80%, 90%, 95%, 98% or 99% identical to SEQ ID NO:4, wherein the polypeptide has a leucine at position 23, an isoleucine at position 108 and a leucine at position 140, and wherein the first polypeptide is linked to a second polypeptide comprising UPRT or OPRT activity. In one embodiment, the polypeptides having UPRT or OPRT activity comprises a sequence as set forth in SEQ ID NO:8 and 10, respectively, or variants thereof. In yet another embodiment, a first polypeptide comprising cytosine deaminase activity is linked to a polypeptide having UPRT or OPRT activity, wherein the polypeptides are separated by a peptide linker. In another embodiment, the fusion construct comprises a sequence selected from the group consisting of SEQ ID NO:11, 12 or 13.

The term "operably linked" or "operably associated" refers to a functional linkage or association between a regulatory sequence and the polynucleotide regulated by the regulatory sequence or between two distinct polypeptides or polynucleotides encoding such polypeptides.

A fusion construct comprising a polypeptide having CD activity and a polypeptide comprising UPRT or OPRT activity can be engineered to contain a cleavage site to aid in protein recovery or other linker moiety. Typically a linker will be a peptide linker moiety. The length of the linker moiety is chosen to optimize the biological activity of the CD polypeptide and the UPRT or OPRT polypeptide and can be determined empirically without undue experimentation. The linker moiety should be long enough and flexible enough to allow a substrate to interact with the CD polypeptide and a substrate with the UPRT or OPRT polypeptide. A linker moiety is a peptide between about one and 30 amino acid residues in length, typically between about two and 15 amino acid residues. Examples of linker moieties are -Gly-Gly-, GGGGS (SEQ ID NO:23), (GGGGS)$_N$ (SEQ ID NO:23), (SGGGG)$_N$ (SEQ ID NO: 24), GKSSGSGSESKS (SEQ ID NO:25), GSTSGSGKSSEGKG (SEQ ID NO:26), GSTSGSGKSSEGSGSTKG (SEQ ID NO:27), GSTSGSGKPGSGEGSTKG (SEQ ID NO:28), or EGKSSGSGSESKEF (SEQ ID NO:29). Linking moieties are described, for example, in Huston et al., Proc. Nat'l Acad. Sci 85:5879, 1988; Whitlow et al., Protein Engineering 6:989, 1993; and Newton et al., Biochemistry 35:545, 1996. Other suitable peptide linkers are those described in U.S. Pat. Nos. 4,751,180 and 4,935,233, which are hereby incorporated by reference. A DNA sequence encoding a desired peptide linker can be inserted between, and in the same reading frame as, a polynucleotide encoding a CD polypeptide followed by a UPRT or OPRT polypeptide, using any suitable conventional technique. For example, a chemically synthesized oligonucleotide encoding the linker can be ligated between two coding polynucleotides. In particular embodiments, a fusion polypeptide comprises from two to four separate domains (e.g., a CD domain and a UPRT or OPRT) are separated by peptide linkers.

"Conservative amino acid substitution" or, simply, "conservative variations" of a particular sequence refers to the replacement of one amino acid, or series of amino acids, with essentially identical amino acid sequences. One of skill will recognize that individual substitutions, deletions or additions which alter, add or delete a single amino acid or a percentage of amino acids in an encoded sequence result in "conservative variations" where the alterations result in the deletion of an amino acid, addition of an amino acid, or substitution of an amino acid with a chemically similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence (e.g., SEQ ID NOs: 2, 4, 6, 8, 10, 11, 12, 13 etc.) include substitutions of a percentage, typically less than 10%, of the amino acids of the polypeptide sequence, with a conservatively selected amino acid of the same conservative substitution group. Accordingly, a conservatively substituted variation of a polypeptide of the disclosure can contain 100, 75, 50, 25, or 10 substitutions with a conservatively substituted variation of the same conservative substitution group.

The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "cytosine deaminase activity", "biological activity of cytosine deaminse" or "functional activity of a cytosine deaminse", refers to an activity exerted by a cytosine deaminase protein, or polypeptide of the disclosure, on a cytosine deaminase substrate, as determined in vivo, or in vitro, according to standard techniques. Assays for measuring cytosine deaminase activity are known in the art. For example, an cytosine deaminase activity can measure by determining the rate of conversion of 5-FC to 5-FU or cytosine to uracil. The detection of 5-FC, 5-FU, cytosine and uracil can be performed by chromatography and other methods known in the art.

One of skill in the art will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. It will be appreciated by those skilled in the art that due to the degeneracy of the genetic code, a multitude of nucleotide sequences encoding modified cytosine deaminase polypeptides of the disclosure may be produced, some of which bear substantial identity to the nucleic acid sequences explicitly disclosed herein. For instance, codons AGA, AGG, CGA, CGC, CGG, and CGU all encode the amino acid arginine. Thus, at every position in the nucleic acids of the disclosure where an arginine is specified by a codon, the codon can be altered to any of the corresponding codons described above without altering the encoded polypeptide. It is understood that U in an RNA sequence corresponds to T in a DNA sequence.

Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the polypeptides provided herein.

"Conservative variants" are proteins or enzymes in which a given amino acid residue has been changed without altering overall conformation and function of the protein or enzyme including, but not limited to, replacement of an amino acid with one having similar properties, including polar or non-polar character, size, shape and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, or at least 90%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity. For example, the "identity" or "percent identity" with respect to a particular pair of aligned amino acid sequences can refer to the percent amino acid sequence identity that is obtained by ClustalW analysis (version W 1.8 available from European Bioinformatics Institute, Cambridge, UK), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins" in "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Nat'l. Acad. Sci. USA 89: 10915-10919. The BLOSUM62 matrix (FIG. 10) is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) Nucl. Acids Res. 25: 3389-3402, and made available to the public at the National Center for Biotechnology Information (NCBI) Website (www.ncbi.nlm.nih.gov). Optimal alignments, including multiple alignments, can be prepared using, e.g., PSI-BLAST, available through the NCB1 website and described by Altschul et al. (1997) Nucl. Acids Res. 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Non-conservative modifications of a particular polypeptide are those which substitute any amino acid not characterized as a conservative substitution. For example, any substitution which crosses the bounds of the six groups set forth above. These include substitutions of basic or acidic amino acids for neutral amino acids (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), histidine (H).

Accordingly, some amino acid residues at specific positions in a polypeptide are "excluded" from conservative amino acid substitutions. For example, the disclosure provides a polypeptide comprising a sequence as set forth in SEQ ID NO:4. In some embodiments, the polypeptide may be altered with conservative amino acid substitutions as described above, however, certain residues are desirably left unsubstituted such as residues at positions 23, 108, and 140.

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A polynucleotide, polypeptide, or other component is "isolated" when it is partially or completely separated from components with which it is normally associated (other proteins, nucleic acids, cells, synthetic reagents, etc.). A nucleic acid or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

In other embodiments, isolated polynucleotides are provided that encode a cytosine deaminase polypeptide or fusion construct of the disclosure. In one aspect, the disclosure provides an isolated or recombinant polynucleotides referred to herein as "CD optimized polynucleotides", "CD polynucleotides" or "CD-fusion polynucleotides." The terms "polynucleotide," "nucleotide sequence," and "nucleic acid molecule" are used to refer to a polymer of nucleotides (A, C, T, U, G, etc. or naturally occurring or artificial nucleotide analogues), e.g., DNA or RNA, or a representation thereof, e.g., a character string, etc., depending on the relevant context. A given polynucleotide or complementary polynucleotide can be determined from any specified nucleotide sequence.

One embodiment of the disclosure pertains to isolated polynucleotides that encode a cytosine deaminase or a mutant cytosine deaminase polypeptide or biologically active portions thereof. As used herein, the term "nucleic acid molecule" or "polynucleotide" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded.

In one embodiment, a CD optimized polynucleotide or CD polynucleotide comprises recombinant, engineered or isolated forms of naturally occurring nucleic acids isolated from an organism, e.g., a bacterial or yeast strain. Exemplary CD polynucleotides include those that encode the wild-type polypeptides set forth in SEQ ID NO: 2. In another embodiment of the disclosure, CD polynucleotides are produced by diversifying, e.g., recombining and/or mutating one or more naturally occurring, isolated, or recombinant CD polynucleotides. As described in more detail elsewhere herein, it is possible to generate diversified CD polynucleotides encoding CD polypeptides with superior functional attributes, e.g., increased catalytic function, increased stability, or higher expression level, than a CD polynucleotide used as a substrate or parent in the diversification process. Exemplary polynucleotides include SEQ ID NO:3 and 5 and those that encode the CD variant polypeptides of the disclosure.

The polynucleotides of the disclosure have a variety of uses in, for example, recombinant production (i.e., expression) of the CD polypeptides of the disclosure and as substrates for further diversity generation, e.g., recombination reactions or mutation reactions to produce new and/or improved CD homologues, and the like.

It is important to note that certain specific, substantial and credible utilities of CD polynucleotides do not require that the polynucleotide encode a polypeptide with substantial CD activity or even variant CD activity. For example, CD polynucleotides that do not encode active enzymes can be valuable sources of parental polynucleotides for use in diversification procedures to arrive at CD polynucleotide variants, or non-CD polynucleotides, with desirable functional properties (e.g., high $k_{cat}$ or $k_{cat}/K_m$, low $K_m$, high stability towards heat or other environmental factors, high transcription or translation rates, resistance to proteolytic cleavage, etc.).

CD polynucleotides, including nucleotide sequences that encode CD polypeptides and variants thereof, fragments of CD polypeptides, related fusion proteins, or functional equivalents thereof, are used in recombinant DNA molecules that direct the expression of the CD polypeptides in appropriate host cells, such as bacterial cells. Due to the inherent degeneracy of the genetic code, other nucleic acid sequences which encode substantially the same or a functionally equivalent amino acid sequence can also be used to clone and express the CD polynucleotides. The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) Gene 105:61-72). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA, respectively. The preferred stop codon for monocotyledonous plants is UGA, whereas insects and *E. coli* prefer to use UAA as the stop codon (Dalphin et al. (1996) Nucl. Acids Res. 24: 216-218).

Codon usage bias refers to differences among organisms in the frequency of occurrence of codons in protein-coding DNA sequences (genes). A codon is a series of three nucleotides (triplets) that encodes a specific amino acid residue in a polypeptide chain. Because there are four nucleotides in DNA, adenine (A), guanine (G), cytosine (C) and thymine (T), there are 64 possible triplets encoding 20 amino acids, and three translation termination (nonsense) codons. Because of this redundancy, all but two amino acids are encoded by more than one triplet. Different organisms often show particular preferences for one of the several codons that encode the same amino acid. How these preferences arise is a much debated area of molecular evolution.

It is generally acknowledged that codon preferences reflect a balance between mutational biases and natural selection for translational optimization. Optimal codons in fast-growing microorganisms, like *Escherichia coli* or *Saccharomyces cerevisiae* (baker's yeast), reflect the composition of their respective genomic tRNA pool. It is thought that optimal codons help to achieve faster translation rates and high accuracy. As a result of these factors, translational selection is expected to be stronger in highly expressed genes, as is indeed the case for the above-mentioned organisms. In other organisms that do not show high growing rates or that present small genomes, codon usage optimization is normally absent, and codon preferences are determined by the characteristic mutational biases seen in that particular genome. Examples of this are *Homo sapiens* (human) and *Helicobacter pylori*. Organisms that show an intermediate level of codon usage optimization include *Drosophila melanogaster* (fruit fly), *Caenorhabditis elegans* (nematode worm) or *Arabidopsis thaliana* (wall cress).

The term "codon optimized sequences" generally refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

TABLE 1

The human codon usage and codon preference. For each codon, the table displays the frequency of usage of each codon (per thousand) in human coding regions (first column) and the relative frequency of each codon among synonymous codons (second column).

The Human Codon Usage Table

| AA | Codon | Freq | Rel | AA | Codon | Freq | Rel | AA | Codon | Freq | Rel | AA | Codon | Freq | Rel |
|---|---|---|---|---|---|---|---|---|---|---|---|---|---|---|---|
| Gly | GGG | 17.08 | 0.23 | Arg | AGG | 12.09 | 0.22 | Trp | TGG | 14.74 | 1.00 | Arg | CGG | 10.40 | 0.19 |
| Gly | GGA | 19.31 | 0.26 | Arg | AGA | 11.73 | 0.21 | End | TGA | 2.64 | 0.61 | Arg | CGA | 5.63 | 0.10 |
| Gly | GGT | 13.66 | 0.18 | Ser | AGT | 10.18 | 0.14 | Cys | TGT | 9.99 | 0.42 | Arg | CGT | 5.16 | 0.09 |
| Gly | GGC | 24.94 | 0.33 | Ser | AGC | 18.54 | 0.25 | Cys | TGC | 13.86 | 0.58 | Arg | CGC | 10.82 | 0.19 |
| Glu | GAG | 38.82 | 0.59 | Lys | AAG | 33.79 | 0.60 | End | TAG | 0.73 | 0.17 | Gln | CAG | 32.95 | 0.73 |
| Glu | GAA | 27.51 | 0.41 | Lys | AAA | 22.32 | 0.40 | End | TAA | 0.95 | 0.22 | Gln | CAA | 11.94 | 0.27 |
| Asp | GAT | 21.45 | 0.44 | Asn | AAT | 16.43 | 0.44 | Tyr | TAT | 11.80 | 0.42 | His | CAT | 9.56 | 0.41 |
| Asp | GAC | 27.06 | 0.56 | Asn | AAC | 21.30 | 0.56 | Tyr | TAC | 16.48 | 0.58 | His | CAC | 14.00 | 0.59 |
| Val | GTG | 28.60 | 0.48 | Met | ATG | 21.86 | 1.00 | Leu | TTG | 11.43 | 0.12 | Leu | CTG | 39.93 | 0.43 |
| Val | GTA | 6.09 | 0.10 | Ile | ATA | 6.05 | 0.14 | Leu | TTA | 5.55 | 0.06 | Leu | CTA | 6.42 | 0.07 |
| Val | GTT | 10.30 | 0.17 | Ile | ATT | 15.03 | 0.35 | Phe | TTT | 15.36 | 0.43 | Leu | CTT | 11.24 | 0.12 |
| Val | GTC | 15.01 | 0.25 | Ile | ATC | 22.47 | 0.52 | Phe | TTC | 20.72 | 0.57 | Leu | CTC | 0.14 | 0.20 |

TABLE 1-continued

The human codon usage and codon preference. For
each codon, the table displays the frequency of usage of each codon
(per thousand) in human coding regions (first column) and the
relative frequency of each codon among synonymous codons (second column).

The Human Codon Usage Table

| Ala | GCG | 7.27 | 0.10 | Thr | ACG | 6.80 | 0.12 | Ser | TCG | 4.38 | 0.06 | Pro | CCG | 7.02 | 0.11 |
| --- | --- | --- | --- | --- | --- | --- | --- | --- | --- | --- | --- | --- | --- | --- | --- |
| Ala | GCA | 15.50 | 0.22 | Thr | ACA | 15.04 | 0.27 | Ser | TCA | 10.96 | 0.15 | Pro | CCA | 17.11 | 0.27 |
| Ala | GCT | 20.23 | 0.28 | Thr | ACT | 13.24 | 0.23 | Ser | TCT | 13.51 | 0.18 | Pro | CCT | 18.03 | 0.29 |
| Ala | GCC | 28.43 | 0.40 | Thr | ACC | 21.52 | 0.38 | Ser | TCC | 17.37 | 0.23 | Pro | CCC | 20.51 | 0.33 |

Accordingly, in some embodiments of the disclosure a polynucleotide comprises a molecule codon optimized for translation in a human cell. For example, SEQ ID NO:3 and 5 comprise sequences that have been optimized for producing cytosine deaminase in a human host cell.

The disclosure thus provides a human codon optimized polynucleotide encoding a polypeptide having cytosine deaminase activity. A human codon optimized polynucleotide of the disclosure (e.g., SEQ ID NO:5) may further include additional mutations resulting in conservative amino acid substitution and or improved activity or stability of the encoded polypeptide. For example, mutations at positions 23, 108 and 140 of the polypeptide comprising SEQ ID NO:6 provide increased thermostability. Accordingly, the disclosure provides a human codon optimized polynucleotide encoding a polypeptide having cytosine deaminase activity and increased thermostability. In one embodiment, the human codon optimized polynucleotide comprises a sequence encoding a polypeptide of SEQ ID NO:4, wherein the codons encoding the amino acids of the polypeptide have been optimized for expression in a human cell. In another embodiment, a polynucleotide of the disclosure comprises SEQ ID NO:3 or 5.

In one embodiment, the disclosure provides a polynucleotide comprising a cytosine deaminase polynucleotide or a codon optimized polynucleotide or mutant linked to a heterologous polynucleotide encoding a polypeptide having UPRT or OPRT activity.

A polynucleotide of the disclosure comprising, e.g., a sequence encoding the polypeptide of SEQ ID NO:4, 8, 10, 12, 14, 16, or 18; or having the nucleotide sequence of set forth in any of SEQ ID NOs:3, 5, 7, 9, 11, 13, 15, or 17, or a portion thereof, can be isolated and generated using standard molecular biology techniques and the sequence information provided herein.

A polynucleotide of the disclosure can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer. In some embodiments, an isolated nucleic acid molecule of the disclosure comprises a nucleic acid molecule which is a complement of a nucleotide sequence encoding a polypeptide set forth in any of SEQ NOs:2, 4, 6, 8, 10, 12, 14, 16, or 18, or having the nucleotide sequence of set forth in any of SEQ ID NOs:1, 3, 5, 7, 9, 11, 13, 15, or 17.

In another embodiment, an isolated polynucleotide of the disclosure comprises a nucleic acid molecule that hybridizes under stringent conditions to a nucleic acid molecule consisting of the nucleotide sequence encoding a polypeptide set forth in any of SEQ NOs:4, 12, 14, 16 or 18, or consisting of the nucleotide sequence set forth in any of SEQ ID NOs:3, 5, 11, 13, 15, or 17. In other embodiments, the nucleic acid is at least 30, 50, 100, 150, 200, 250, 300, 350, 400, 450, 500, 550, or 600 nucleotides in length. Nucleic acid molecules are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences (1×SSC is 0.15 M NaCl, 0.015 M Na citrate). Nucleic acid molecules that hybridize include those which anneal under suitable stringency conditions and which encode polypeptides or enzymes having the same function, such as the ability to catalyze the conversion of 5-Fluorocytosine (5-FC) to 5-fluorouracil (5-FU), of the disclosure. Further, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. In some cases, an isolated nucleic acid molecule of the disclosure hybridizes under stringent conditions to a nucleic acid sequence encoding a polypeptide set forth in any of SEQ ID NOs: 4, 12, 14, 16, or 18, or having the nucleotide sequence set forth in any of SEQ ID NOs: 3, 5, 11, 13, 15, or 17. As used herein, a "naturally-occurring" nucleic acid molecule refers to an RNA or DNA molecule having a nucleotide sequence that occurs in nature (e.g., encodes a natural protein).

The skilled artisan will appreciate that changes can be introduced by mutation into the nucleotide sequences of any polynucleotides encoding a polypeptide set forth in any of SEQ ID NOs: 2, 4, 6, 8, 10, 12, 14, 16, or 18, or having the nucleotide sequence set forth in any of SEQ ID NOs: 1, 3, 5, 7, 9, 11, 13, 15, or 17, thereby leading to changes in the amino acid sequence of the encoded proteins. In some cases the alteration will lead to altered function of the polypeptide. In other cases the change will not alter the functional ability of the encoded polypeptide. In general, substitutions that do not alter the function of a polypeptide include nucleotide substitutions leading to amino acid substitutions at "non-essential" amino acid residues. A "non-essential" amino acid residue is a residue that can be altered from the parent sequence without altering the biological activity of the resulting polypeptide, e.g., catalyzing the conversion of 5-FC to 5-FU.

Also contemplated are those situations where it is desirable to alter the activity of a parent polypeptide such that the polypeptide has new or increased activity on a particular substrate or increased stability or reduced degradation. It is understood that these amino acid substitutions will generally not constitute "conservative" substitutions. Instead, these substitutions constitute non-conservative substitutions introduced in to a sequence in order to obtain a new or improved activity. For example, SEQ ID NO:1 provides the parent nucleic acid sequence for *S. cervisae* cytosine deaminase (SEQ ID NO:2 provides the corresponding polypeptide). SEQ ID NO:3 provides the nucleic acid sequence of a mutant sequence that includes amino acid substitutions that impart increased stability to the polypeptide. Accordingly, the nucleic acid molecule encoding the amino acid sequence of SEQ ID NO:2 provides a "parent" nucleic acid molecule from which mutations can be made to obtain a nucleic acid molecule that encodes a modified polypeptide that includes amino acid substitutions.

It is also understood that a modified polypeptide can constitute a "parent" polypeptide from which additional substitutions can be made. Accordingly, a parent polypeptide, and a nucleic acid molecule that encodes a parent polypeptide, includes modified polypeptides and not just "wild-type" sequences. For example, the polynucleotide of SEQ ID NO:5 is a modified polynucleotide with respect to SEQ ID NO:1 (i.e., the "parent" polynucleotide). Similarly, the polynucleotide of SEQ ID NO:3 is a modified polynucleotide with respect to SEQ ID NO:5. Accordingly, SEQ ID NO:5 is the parent sequence of SEQ ID NO:3.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100: 468-500; and Zoller & Smith (1987) "Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787; Nakamaye & Eckstein (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional suitable methods include point mismatch repair (Kramer et al. (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh & Henikoff (1986) "Use of oligonucleotides to generate large deletions" Nucl. Acids Res. 14: 5115), restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shotgun' gene synthesis" Nucl. Acids Res. 13: 3305-3316); double-strand break repair (Mandecki (1986); Arnold (1993) "Protein engineering for unusual environments" Current Opinion in Biotechnology 4:450-455; and "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter.

Also provided are recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), a viral vector or the like, into which a polynucleotide of the disclosure has been inserted, in a forward or reverse orientation. Large numbers of suitable vectors and promoters are known to those of skill in the art, and are commercially available. In one embodiment, the viral vector is a retroviral vector.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used. These nucleic acid vectors can be delivered using a non-viral delivery system such as described in P. Midoux et al. Brit J Pharm 157: 166-178 2009 or Kamimura & Liu J AAPS 10:589-595 (2008) or a viral system as described below.

In another aspect, the polynucleotide encoding a cytosine deaminase or mutant thereof is delivered with a gene delivery system that is a viral or viral derived vector. The viral vector can be replicating or non-replicating, and can be an adenoviral vector, a measles vector, a herpes vector, a retroviral vector (including a lentiviral vector), a rhabdoviral vector such as a Vesicular Stomatitis viral vector, a reovirus vector, a Seneca Valley Virus vector, a poxvirus vector (including animal pox or vaccinia derived vectors), a parvovirus vector (including an AAV vector), an alphavirus vector or other viral vector known to one skilled in the art (see also, e.g., *Concepts in Genetic Medicine*, ed. Boro Dropulic and Barrie Carter, Wiley, 2008, Hoboken, N.J.; *The Development of Human Gene Therapy*, ed. Theodore Friedmann, Cold Springs Harbor Laboratory Press, Cold springs Harbor, N.Y., 1999; *Gene and Cell Therapy*, ed. Nancy Smyth Templeton, Marcel Dekker Inc., New York, N.Y., 2000 and *Gene Therapy: Therapeutic Mechanism and Strategies*, ed. Nancy Smyth Templetone and Danilo D Lasic, Marcel Dekker, Inc., New York, N.Y., 2000; the disclosures of which are incorporated herein by reference).

In one embodiment, the viral vector can be a replication competent retroviral vector capable of infecting only replicating mammalian cells. Retroviruses have been classified in various ways but the nomenclature has been standardized in the last decade (see ICTVdB—The Universal Virus Database, v 4 on the World Wide Web (www) at ncbi.nlm.nih.gov/ICTVdb/ICTVdB/ and the text book "Retroviruses" Eds Coffin, Hughs and Varmus, Cold Spring Harbor Press 1997; the disclosure of which are incorporated herein by reference). The replication competent retroviral vector can comprise an Orthoretrovirus or more typically a gamma retrovirus vector. In one aspect, a replication competent retroviral vector comprises an internal ribosomal entry site (IRES) 5' to the polynucleotide encoding a cytosine deaminase. In one embodiment, the polynucleotide encoding a cytosine deaminase is 3' to an ENV polynucleotide of a retroviral vector. In one embodiment the viral vector is a retroviral vector capable of infecting target cells multiple times (5 or more per diploid cell).

Accordingly, in other embodiments, vectors that include a polynucleotide of the disclosure are provided. In other embodiments, host cells transfected with a nucleic acid molecule of the disclosure, or a vector that includes a polynucleotide of the disclosure, are provided. Host cells include eucaryotic cells such as yeast cells, insect cells, or animal cells. Host cells also include prokaryotic cells such as bacterial cells.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Also provided are engineered host cells that are transduced (transformed or transfected) with a vector provided herein (e.g., a cloning vector or an expression vector), as well as the production of polypeptides of the disclosure by recombinant techniques. The vector may be, for example, a plasmid, a viral particle, a phage, etc. The engineered host cells can be cultured in conventional nutrient media modified as appropriate for activating promoters, selecting transformants, or amplifying a coding polynucleotide. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

Vectors can be employed to transform an appropriate host to permit the host to express a protein or polypeptide. Examples of appropriate expression hosts include: bacterial cells, such as *E. coli, B. subtilis, Streptomyces,* and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 or Bowes melanoma; or plant cells or explants, etc.

In bacterial systems, a number of expression vectors may be selected depending upon the use intended cytosine deaminase polypeptide. For example, when large quantities of CD polypeptide or fragments thereof are needed for commercial production or for induction of antibodies, vectors which direct high level expression of fusion proteins that are readily purified can be desirable. Such vectors include, but are not limited to, multifunctional *E. coli* cloning and expression vectors such as BLUESCRIPT (Stratagene), in which the CD polypeptide coding sequence may be ligated into the vector in-frame with sequences for the amino-terminal Met and the subsequent 7 residues of beta-galactosidase so that a hybrid protein is produced; pIN vectors (Van Heeke & Schuster (1989) J. Biol. Chem. 264: 5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the CD polypeptides of the disclosure. For reviews, see Ausubel (supra) and Grant et al. (1987) Methods in Enzymology 153:516-544.

The disclosure also provides replication competent retroviral vectors having increased stability relative to prior retroviral vectors. Such increased stability during infection and replication is important for the treatment of cell proliferative disorders. The combination of transduction efficiency, transgene stability and target selectivity is provided by the replication competent retrovirus. The compositions and methods provide insert stability and maintain transcription activity of the transgene and the translational viability of the encoded polypeptide.

Retroviruses can be transmitted horizontally and vertically. Efficient infectious transmission of retroviruses requires the expression on the target cell of receptors which specifically recognize the viral envelope proteins, although viruses may use receptor-independent, nonspecific routes of entry at low efficiency. Normally a viral infection leads to a single or few copies of viral genome per cell because of receptor masking or down-regulation, that in turn leads to resistance to super-infection (Ch3 p104 in "Retroviruses" J M Coffin, S H Hughes, & H E Varmus 1997 Cold Spring Harbor Laboratory Press, Cold Spring Harbor N.Y.; Fan et al. J. Virol 28:802, 1978). By manipulating the situation in tissue culture it is possible to get some level of multiple infection but this is less than 5 copies/diploid genome. In addition, the target cell type must be able to support all stages of the replication cycle after virus has bound and penetrated. Vertical transmission occurs when the viral genome becomes integrated in the germ line of the host. The provirus will then be passed from generation to generation as though it were a cellular gene. Hence endogenous proviruses become established which frequently lie latent, but which can become activated when the host is exposed to appropriate agents.

In many situations for using a recombinant replication competent retrovirus therapeutically, it is advantageous to have high levels of expression of the transgene that is encoded by the recombinant replication competent retrovirus. For example, with a prodrug activating gene such as the cytosine deaminase gene it is advantageous to have higher levels of expression of the CD protein in a cell so that the conversion of the prodrug 5-FC to 5-FU is more efficient. Similarly high levels of expression of siRNA or shRNA lead to more efficient suppression of target gene expression. Also for cytokines or single chain antibodies (scAbs) it is usually advantageous to express high levels of the cytokine or scAb. In addition, in the case that there are mutations in some copies of the vector that inactivate or impair the activity of the vector or transgene, it is advantageous to have multiple copies of the vector in the target cell as this provides a high probability of efficient expression of the intact transgene. The disclosure provides recombinant replication competent retroviruses capable of infecting a target cell or target cell population multiple times resulting in an average number of copies/diploid genome of 5 or greater. The disclosure also provides methods of testing for this property. Also provided are methods of treating a cell proliferative disorder, using a recombinant replication competent retrovirus capable of infecting a target cell or target cell population multiple times resulting in an average number of copies/diploid genome of 5 or greater.

As mentioned above, the integrated DNA intermediate is referred to as a provirus. Prior gene therapy or gene delivery systems use methods and retroviruses that require transcription of the provirus and assembly into infectious virus while in the presence of an appropriate helper virus or in a cell line containing appropriate sequences enabling encapsidation without coincident production of a contaminating helper virus. As described below, a helper virus is not required for the production of the recombinant retrovirus of the disclosure, since the sequences for encapsidation are provided in the genome thus providing a replication competent retroviral vector for gene delivery or therapy.

A retroviral genome useful in the methods and compositions of the disclosure comprises a proviral DNA having at least three genes: the gag, the pol, and the env, these genes may be flanked by one or two long terminal (LTR) repeat, or in the provirus are flanked by two long terminal repeat (LTR) and sequences containing cis-acting sequences such as psi. The gag gene encodes the internal structural (matrix, capsid, and nucleocapsid) proteins; the pol gene encodes the RNA-directed DNA polymerase (reverse transcriptase), protease and integrase; and the env gene encodes viral envelope glycoproteins. The 5' and/or 3' LTRs serve to promote transcription and polyadenylation of the virion RNAs. The LTR contains all other cis-acting sequences necessary for viral replication. Lentiviruses have additional genes including vif, vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virion) are missing from the viral genome, the result is a cis defect which prevents encapsidation of genomic viral RNA. This type of modified vector is what has typically been used in prior gene delivery systems (i.e., systems lacking elements which are required for encapsidation of the virion).

In one embodiment, the disclosure provides a recombinant retrovirus capable of infecting a non-dividing cell, a dividing cell, or a cell having a cell proliferative disorder. The recombinant replication competent retrovirus of the disclosure comprises a polynucleotide sequence encoding a viral GAG, a viral POL, a viral ENV, a heterologous polynucleotide preceded by an internal ribosome entry site (IRES) encapsulated within a virion.

The heterologous nucleic acid sequence is operably linked to an IRES. As used herein, the term "heterologous" nucleic acid sequence or transgene refers to (i) a sequence that does not normally exist in a wild-type retrovirus, (ii) a sequence that originates from a foreign species, or (iii) if from the same species, it may be substantially modified from its original form. Alternatively, an unchanged nucleic acid sequence that is not normally expressed in a cell is a heterologous nucleic acid sequence. In a specific embodiment, the heterologous polynucleotide is a polypeptide of the disclosure having cytosine deaminase activity.

The phrase "non-dividing" cell refers to a cell that does not go through mitosis. Non-dividing cells may be blocked at any point in the cell cycle, (e.g., $G_0/G_1$, $G_{1/S}$, $G_{2/M}$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). For example, a recombinant lentivirus vector is capable of infecting non-dividing cell. Examples of pre-existing non-dividing cells in the body include neuronal, muscle, liver, skin, heart, lung, and bone marrow cells, and their derivatives. For dividing cells oncoretroviral vectors can be used.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells. The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous cell cancer, malignant melanoma, sinonasal undifferentiated carcinoma (SNUC), brain (including glioblastomas) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp 1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer, skin cancer and ovarian cancer.

In one embodiment, the heterologous polynucleotide within the vector comprises a cytosine deaminase that has been optimized for expression in a human cell. In a further embodiment, the cytosine deaminase comprises a sequence that has been human codon optimized and comprises mutations that increase the cytosine deaminase's stability (e.g., reduced degradation or increased thermo-stability) compared to a wild-type cytosine deaminase. In yet another embodiment, the heterologous polynucleotide encodes a fusion construct comprising a cytosine deaminase (either human codon optimized or non-optimized, either mutated or non-mutated) operably linked to a polynucleotide encoding a polypeptide having UPRT or OPRT activity. In another embodiment, the heterologous polynucleotide comprises a CD polynucleotide or fusion construct of the disclosure (e.g., SEQ ID NO:3, 5, 11, 13, 15, or 17).

In another embodiment, replication competent retroviral vector can comprise a heterologous polynucleotide encoding a polypeptide comprising a cytosine deaminase (as described herein) and may further comprise a polynucleotide comprising a miRNA or siRNA molecule linked to a cell-type or tissue specific promoter.

The term "regulatory nucleic acid sequence" refers collectively to promoter sequences, polyadenylation signals, transcription termination sequences, upstream regulatory domains, origins of replication, enhancers and the like, which collectively provide for the replication, transcription and translation of a coding sequence in a recipient cell. Not all of these control sequences need always be present so long as the selected coding sequence is capable of being replicated, transcribed and translated in an appropriate host cell. One skilled in the art can readily identify regulatory nucleic acid sequence from public databases and materials. Furthermore, one skilled in the art can identify a regulatory sequence that is applicable for the intended use, for example, in vivo, ex vivo, or in vitro.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter as described above.

An internal ribosome entry sites ("IRES") refers to a segment of nucleic acid that promotes the entry or retention of a ribosome during translation of a coding sequence usually 3' to the IRES. In some embodiments the IRES may comprise a splice acceptor/donor site, however, preferred IRESs lack a splice acceptor/donor site. Normally, the entry of ribosomes into messenger RNA takes place via the cap located at the 5' end of all eukaryotic mRNAs. However, there are exceptions to this universal rule. The absence of a cap in some viral mRNAs suggests the existence of alternative structures permitting the entry of ribosomes at an internal site of these RNAs. To date, a number of these structures, designated IRES on account of their function, have been identified in the 5' noncoding region of uncapped viral mRNAs, such as that, in particular, of picornaviruses such as the poliomyelitis virus (Pelletier et al., 1988, Mol. Cell. Biol., 8, 1103-1112) and the EMCV virus (encephalo-myocarditis virus (Jang et al., J. Virol., 1988, 62, 2636-2643). The disclosure provides the use of an IRES in the context of a replication-competent retroviral vector.

The heterologous nucleic acid sequence is typically under control of either the viral LTR promoter-enhancer signals or an internal promoter, and retained signals within the retroviral LTR can still bring about efficient integration of the vector into the host cell genome. Accordingly, the recombinant retroviral vectors of the disclosure, the desired sequences, genes and/or gene fragments can be inserted at several sites and under different regulatory sequences. For example, a site for insertion can be the viral enhancer/promoter proximal site (i.e., 5' LTR-driven gene locus). Alternatively, the desired sequences can be inserted into a distal site (e.g., the IRES sequence 3' to the env gene) or where two or more heterologous sequences are present one heterologous sequence may be under the control of a first regulatory region and a second heterologous sequence under the control of a second regulatory region. Other distal sites include viral promoter sequences, where the expression of the desired sequence or sequences is through splicing of the promoter proximal cistron, an internal heterologous promoter as SV40 or CMV, or an internal ribosome entry site (IRES) can be used.

In one embodiment, the retroviral genome of the disclosure contains an IRES comprising a cloning site for insertion of a desired polynucleotide sequence. In one embodiment, the IRES is located 3' to the env gene in the retroviral vector, but 5' to the desired heterologous nucleic acid. Accordingly, a heterologous polynucleotide sequence encoding a desired polypeptide may be operably linked to the IRES.

In another embodiment a targeting polynucleotide sequence is included as part of the recombinant retroviral vector of the disclosure. The targeting polynucleotide sequence is a targeting ligand (e.g., peptide hormones such as heregulin, a single-chain antibodies, a receptor or a ligand for a receptor), a tissue-specific or cell-type specific regulatory element (e.g., a tissue-specific or cell-type specific promoter or enhancer), or a combination of a targeting ligand and a tissue-specific/cell-type specific regulatory element. Preferably, the targeting ligand is operably linked to the env protein of the retrovirus, creating a chimeric retroviral env protein. The viral GAG, viral POL and viral ENV proteins can be derived from any suitable retrovirus (e.g., MLV or lentivirus-derived). In another embodiment, the viral ENV protein is non-retrovirus-derived (e.g., CMV or VSV).

The recombinant retrovirus of the disclosure is therefore genetically modified in such a way that the virus is targeted to a particular cell type (e.g., smooth muscle cells, hepatic cells, renal cells, fibroblasts, keratinocytes, mesenchymal stem cells, bone marrow cells, chondrocyte, epithelial cells, intestinal cells, neoplastic cells, glioma cells, neuronal cells and others known in the art) such that the nucleic acid genome is delivered to a target non-dividing, a target dividing cell, or a target cell having a cell proliferative disorder. Targeting can be achieved in two ways. The first way directs the retrovirus to a target cell by binding to cells having a molecule on the external surface of the cell. This method of targeting the retrovirus utilizes expression of a targeting ligand on the coat of the retrovirus to assist in targeting the virus to cells or tissues that have a receptor or binding molecule which interacts with the targeting ligand on the surface of the retrovirus. After infection of a cell by the virus, the virus injects its nucleic acid into the cell and the retrovirus genetic material can integrate into the host cell genome. The second method for targeting uses cell- or tissue-specific regulatory elements to promote expression and transcription of the viral genome in a targeted cell which actively utilizes the regulatory elements, as described more fully below. The transferred retrovirus genetic material is then transcribed and translated into proteins within the host cell. The targeting regulatory element is typically linked to the 5' and/or 3' LTR, creating a chimeric LTR.

By inserting a heterologous nucleic acid sequence of interest into the viral vector of the disclosure, along with another gene which encodes, for example, the ligand for a receptor on a specific target cell, the vector is now target specific. Viral vectors can be made target specific by attaching, for example, a sugar, a glycolipid, or a protein. Targeting can be accomplished by using an antibody to target the viral vector. Those of skill in the art will know of, or can readily ascertain, specific polynucleotide sequences which can be inserted into the viral genome or proteins which can be attached to a viral envelope to allow target specific delivery of the viral vector containing the nucleic acid sequence of interest.

Thus, the disclosure includes in one embodiment, a chimeric env protein comprising a retroviral env protein operably linked to a targeting polypeptide. The targeting polypeptide can be a cell specific receptor molecule, a ligand for a cell specific receptor, an antibody or antibody fragment to a cell specific antigenic epitope or any other ligand easily identified in the art which is capable of binding or interacting with a target cell. Examples of targeting polypeptides or molecules include bivalent antibodies using biotin-streptavidin as linkers (Etienne-Julan et al., J. Of General Virol., 73, 3251-3255 (1992); Roux et al., Proc. Natl. Acad. Sci USA 86, 9079-9083 (1989)), recombinant virus containing in its envelope a sequence encoding a single-chain antibody variable region against a hapten (Russell et al., Nucleic Acids Research, 21, 1081-1085 (1993)), cloning of peptide hormone ligands into the retrovirus envelope (Kasahara et al., Science, 266, 1373-1376 (1994)), chimeric EPO/env constructs (Kasahara et al., 1994), single-chain antibody against the low density lipoprotein (LDL) receptor in the ecotropic MLV envelope, resulting in specific infection of HeLa cells expressing LDL receptor (Somia et al., Proc. Natl. Acad. Sci USA, 92, 7570-7574 (1995)), similarly the host range of ALV can be altered by incorporation of an integrin ligand, enabling the virus to now cross species to specifically infect rat glioblastoma cells (Valsesia-Wittmann et al., J. Virol. 68, 4609-4619 (1994)), and Dornberg and co-workers (Chu and Dornburg, J. Virol 69, 2659-2663 (1995)) have reported tissue-specific targeting of spleen necrosis virus (SNV), an avian retrovirus, using envelopes containing single-chain antibodies directed against tumor markers.

The disclosure provides a method of producing a recombinant retrovirus capable of infecting a target cell comprising transfecting a suitable host cell with the following: a vector comprising a polynucleotide sequence encoding a viral gag, a viral pol and a viral env, wherein the vector contains a cloning site for introduction of a heterologous gene, operably linked to a regulatory nucleic acid sequence, and recovering the recombinant virus.

The retrovirus and methods of the disclosure provide a replication competent retrovirus that does not require helper virus or additional nucleic acid sequence or proteins in order to propagate and produce virion. For example, the nucleic acid sequences of the retrovirus of the disclosure encode, for example, a group specific antigen and reverse transcriptase, (and integrase and protease-enzymes necessary for maturation and reverse transcription), respectively, as discussed above. The viral gag and pol can be derived from a lentivirus, such as HIV or an oncovirus such as MoMLV. In addition, the nucleic acid genome of the retrovirus of the disclosure includes a sequence encoding a viral envelope (ENV) protein. The env gene can be derived from any retroviruses. The env may be an amphotropic envelope protein which allows transduction of cells of human and other species, or may be an ecotropic envelope protein, which is able to transduce only mouse and rat cells. Further, it may be desirable to target the recombinant virus by linkage of the envelope protein with an antibody or a particular ligand for targeting to a receptor of a particular cell-type. As mentioned above, retroviral vectors can be made target specific by inserting, for example, a glycolipid, or a protein. Targeting is often accomplished by using an antibody to target the retroviral vector to an antigen on a particular cell-type (e.g., a cell type found in a certain tissue, or a cancer cell type). Those of skill in the art will know of, or can readily ascertain without undue experimentation, specific methods to achieve delivery of a retroviral vector to a specific target. In one embodiment, the env gene is derived from a non-retrovirus (e.g., CMV or VSV). Examples of retroviral-derived env genes include, but are not limited to: Moloney murine leukemia virus (MoMuLV), Harvey murine sarcoma virus (HaMuSV), murine mammary tumor virus (MuMTV), gibbon ape leukemia virus (GaLV), human immunodeficiency virus (HIV) and Rous Sarcoma Virus (RSV). Other env genes such as Vesicular stomatitis virus (VSV) (Protein G), cytomegalovirus envelope (CMV), or influenza virus hemagglutinin (HA) can also be used.

In one embodiment, the retroviral genome is derived from an onco-retrovirus or gammaretrovirus, and more particularly a mammalian onco-retrovirus or gamma retrovirus. By "derived" is meant that the parent polynucleotide sequence is an wild-type oncovirus which has been modified by insertion or removal of naturally occurring sequences (e.g., insertion of an IRES, insertion of a heterologous polynucleotide encoding, for example, a polypeptide having cytosine deaminase activity of the disclosure and the like).

In another embodiment, the disclosure provides retroviral vectors that are targeted using regulatory sequences. Cell- or tissue-specific regulatory sequences (e.g., promoters) can be utilized to target expression of gene sequences in specific cell populations. Suitable mammalian and viral promoters for the disclosure are described elsewhere herein. Accordingly, in one embodiment, the disclosure provides a retrovirus having tissue-specific promoter elements at the 5' end of the retroviral genome. Preferably, the tissue-specific regulatory elements/sequences are in the U3 region of the LTR of the retroviral genome, including for example cell- or tissue-specific promoters and enhancers to neoplastic cells (e.g., tumor cell-specific enhancers and promoters), and inducible promoters (e.g., tetracycline).

In some circumstances, it may be desirable to regulate expression. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV can be used. Other viral promoters that can be used include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific or selective promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Other promoters/regulatory domains that can be used are set forth in Table 1.

In certain indications, it may be desirable to activate transcription at specific times after administration of the gene therapy vector. This may be done with such promoters as those that are hormone or cytokine regulatable. For example in therapeutic applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones may be used. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitrypsin, lipoprotein lipase (Zechner et al., 1988), angiotensinogen (Ron et al., 1990), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin. Tumor specific promoters such as osteocalcin, hypoxia-responsive element (HRE), MAGE-4, CEA, alpha-fetoprotein, GRP78/BiP and tyrosinase may also be used to regulate gene expression in tumor cells.

In addition, this list of promoters should not be construed to be exhaustive or limiting, those of skill in the art will know of other promoters that may be used in conjunction with the promoters and methods disclosed herein.

TABLE 1

TISSUE SPECIFIC PROMOTERS

| Tissue | Promoter |
|---|---|
| Pancreas | Insulin Elastin Amylase pdr-1 pdx-1 glucokinase |
| Liver | Albumin PEPCK HBV enhancer α fetoprotein apolipoprotein C α-1 antitrypsin vitellogenin, NF-AB Transthyretin |
| Skeletal muscle | Myosin H chain Muscle creatine kinase Dystrophin Calpain p94 Skeletal alpha-actin fast troponin 1 |

TABLE 1-continued

TISSUE SPECIFIC PROMOTERS

| Tissue | Promoter |
|---|---|
| Skin | Keratin K6 Keratin K1 |
| Lung | CFTR Human cytokeratin 18 (K18) Pulmonary surfactant proteins A, B and C CC-10 P1 |
| Smooth muscle | sm22 α SM-alpha-actin |
| Endothelium | Endothelin-1 E-selectin von Willebrand factor TIE, KDR/flk-1 Melanocytes Tyrosinase |
| Adipose tissue | Lipoprotein lipase (Zechner et al., 1988) Adipsin (Spiegelman et al., 1989) acetyl-CoA carboxylase (Pape and Kim, 1989) glycerophosphate dehydrogenase (Dani et al., 1989) adipocyte P2 (Hunt et al., 1986) |
| Breast | Whey Acidic Protein (WAP) (Andres et al. PNAS 84: 1299-1303 1987 |
| Blood | β-globin |

"Tissue-specific regulatory elements" are regulatory elements (e.g., promoters) that are capable of driving transcription of a gene in one tissue while remaining largely "silent" in other tissue types. It will be understood, however, that tissue-specific promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the disclosure typically has a selectivity ratio of greater than about 5. Preferably, the selectivity ratio is greater than about 15.

It will be further understood that certain promoters, while not restricted in activity to a single tissue type, may nevertheless show selectivity in that they may be active in one group of tissues, and less active or silent in another group. Such promoters are also termed "tissue specific", and are contemplated for use with the disclosure. Accordingly, the tissue-specific regulatory elements used in the disclosure, have applicability to regulation of the heterologous proteins such as the polypeptides having cytosine deaminase activity of the disclosure as well as a applicability as a targeting polynucleotide sequence in retroviral vectors.

The retroviral vectors and CD polynucleotides and polypeptides of the disclosure can be used to treat a wide range of disease and disorders including a number of cell proliferative diseases and disorders (see, e.g., U.S. Pat. Nos. 4,405,712 and 4,650,764; Friedmann, 1989, Science, 244: 1275-1281; Mulligan, 1993, Science, 260:926-932, R. Crystal, 1995, Science 270:404-410, each of which are incorporated herein by reference in their entirety, see also, The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

The disclosure also provides gene therapy for the treatment of cell proliferative disorders. Such therapy would achieve its therapeutic effect by introduction of an appropriate therapeutic polynucleotide sequence (e.g., a polypeptide of the disclosure having cytosine deaminase activity), into cells of subject having the proliferative disorder. Delivery of polynucleotide constructs can be achieved using the recombinant retroviral vector of the disclosure.

In addition, the therapeutic methods (e.g., the gene therapy or gene delivery methods) as described herein can be performed in vivo or ex vivo. For example, in the methods for treatment of cell proliferative diseases or disorders it may be useful to remove the majority of a tumor prior to gene therapy, for example surgically or by radiation. In some embodiments, the retroviral therapy may be preceded or followed by chemotherapy.

Thus, the disclosure provides a recombinant retrovirus capable of infecting a non-dividing cell, a dividing cell or a neoplastic cell, wherein the recombinant retrovirus comprises a viral GAG; a viral POL; a viral ENV; a heterologous nucleic acid (e.g., comprising a polypeptide of the disclosure having cytosine deaminase activity) operably linked to an IRES; and cis-acting nucleic acid sequences necessary for packaging, reverse transcription and integration. The recombinant retrovirus can be a lentivirus, such as HIV, or can be an oncovirus. As described above for the method of producing a recombinant retrovirus, the recombinant retrovirus of the disclosure may further include at least one of VPR, VIF, NEF, VPX, TAT, REV, and VPU protein. While not wanting to be bound by a particular theory, it is believed that one or more of these genes/protein products are important for increasing the viral titer of the recombinant retrovirus produced (e.g., NEF) or may be necessary for infection and packaging of virion.

The disclosure also provides a method of nucleic acid transfer to a target cell to provide expression of a particular nucleic acid (e.g., a heterologous sequence such as a polynucleotide encoding a polypeptide having cytosine deaminase activity). Therefore, in another embodiment, the disclosure provides a method for introduction and expression of a heterologous nucleic acid in a target cell comprising infecting the target cell with the recombinant virus of the disclosure and expressing the heterologous nucleic acid in the target cell. As mentioned above, the target cell can be any cell type including dividing, non-dividing, neoplastic, immortalized, modified and other cell types recognized by those of skill in the art, so long as they are capable of infection by a retrovirus.

The disclosure also provides gene therapy for the treatment of cell proliferative or immunologic disorders. In one embodiment, a cell proliferative disorder is treated by introducing a CD polynucleotide of the disclosure, expressing the polynucleotide to produce a polypeptide comprising cytosine deaminase activity and contacting the cell with 5-fluorocytosine in an amount and for a period of time to produce a cytotoxic amount of 5-FU.

In addition, the disclosure provides polynucleotide sequence encoding a recombinant retroviral vector of the disclosure. The polynucleotide sequence can be incorporated into various viral particles. For example, various viral vectors which can be utilized for gene therapy include adenovirus, herpes virus, vaccinia, or, preferably, an RNA virus such as a retrovirus and more particularly a mammalian oncovirus. The retroviral vector can be a derivative of a murine, simian or human retrovirus. Examples of retroviral vectors in which a foreign gene (e.g., a heterologous polynucleotide sequence) can be inserted include, but are not limited to: derivatives of Moloney murine leukemia virus (MoMuLV), Harvey murine sarcoma virus (HaMuSV), murine mammary tumor virus (MuMTV), and Rous Sarcoma Virus (RSV). All of these vectors can transfer or incorporate a gene for a selectable marker so that transduced cells can be identified and generated. In yet another embodiment, the disclosure provides plasmids comprising a recombinant retroviral derived construct. The plasmid can be directly introduced into a target cell or a cell culture such as NIH 3T3, HT1080 (human), CF2 (dog) or other tissue culture cells. The resulting cells release the retroviral vector into the culture medium.

The disclosure provides a polynucleotide construct comprising from 5' to 3': a promoter or regulatory region useful for initiating transcription; a psi packaging signal; a gag encoding nucleic acid sequence, a pol encoding nucleic acid sequence; an env encoding nucleic acid sequence; an internal ribosome entry site nucleic acid sequence; a heterologous polynucleotide encoding a marker, therapeutic (e.g., a polypeptide having cytosine deaminase activity) or diagnostic polypeptide; and a LTR nucleic acid sequence. In specific embodiments, a heterologous polynucleotide encoding a polypeptide having cytosine deaminase activity may further comprise a domain encoding a polypeptide comprising UPRT or OPRT activity.

As described elsewhere herein and as follows the various segment of the polynucleotide construct of the disclosure (e.g., a recombinant replication competent retroviral polynucleotide) are engineered depending in part upon the desired host cell, expression timing or amount, and the heterologous polynucleotide. A replication competent retroviral construct of the disclosure can be divided up into a number of domains that may be individually modified by those of skill in the art.

For example, the promoter can comprise a CMV promoter having a sequence as set forth in SEQ ID NO:19, 20, or 22 from nucleotide 1 to about nucleotide 582 and may include modification to one or more (e.g., 2-5, 5-10, 10-20, 20-30, 30-50, 50-100 or more nucleic acid bases) so long as the modified promoter is capable of directing and initiating transcription. In one embodiment, the promoter or regulatory region comprises a CMV-R-U5 domain polynucleotide. The CMV-R-U5 domain comprise the immediately early promoter from human cytomegalovirus to the MLV R-U5 region. In one embodiment, the CMV-R-U5 domain polynucleotide comprises a sequence as set forth in SEQ ID NO:19, 20, or 22 from about nucleotide 1 to about nucleotide 1202 or sequences that are at least 95% identical to a sequence as set forth in SEQ ID NO:19, 20, or 22, wherein the polynucleotide promotes transcription of a nucleic acid molecule operably linked thereto. The gag domain of the polynucleotide may be derived from any number of retroviruses, but will typically be derived from an oncoretrovirus and more particularly from a mammalian oncoretrovirus. In one embodiment the gag domain comprises a sequence from about nucleotide number 1203 to about nucleotide 2819 or a sequence having at least 95%, 98%, 99% or 99.8% (rounded to the nearest $10^{th}$) identity thereto. The pol domain of the polynucleotide may be derived from any number of retroviruses, but will typically be derived from an oncoretrovirus and more particularly from a mammalian oncoretrovirus. In one embodiment the pol domain comprises a sequence from about nucleotide number 2820 to about nucleotide 6358 or a sequence having at least 95%, 98%, 99% or 99.9% (roundest to the nearest $10^{th}$) identity thereto. The env domain of the polynucleotide may be derived from any number of retroviruses, but will typically be derived from an oncoretrovirus and more particularly from a mammalian oncoretrovirus. In some embodiments the env coding domain comprises an amphotropic env domain. In one embodiment the env domain comprises a sequence from about nucleotide number 6359 to about nucleotide 8323 or a sequence having at least 95%, 98%, 99% or 99.8% (roundest to the nearest $10^{th}$) identity thereto. The IRES domain of the polynucleotide may be obtained from any number of internal ribosome entry sites. In one embodiment, IRES is derived from an encephalomyocarditis virus. In one embodiment the IRES domain comprises a sequence from about nucleotide number 8327 to about nucleotide 8876 or a sequence having at least 95%, 98%, or 99% (roundest to the nearest $10^{th}$) identity thereto so long as the domain allows for entry of a ribosome. The heterologous domain can comprise a cytosine deaminase of the disclosure. In one embodiment, the CD polynucleotide comprises a human codon optimized sequence. In yet another embodiment, the CD polynucleotide encodes a mutant polypeptide having cytosine deaminase, wherein the mutations confer increased thermal stabilization that increase the melting temperature (Tm) by 10° C. allowing sustained kinetic activity over a broader temperature range and increased accumulated levels of protein. In one embodiment, the cytosine deaminase comprises a sequence as set forth in SEQ ID NO:19 from about nucleotide number 8877 to about 9353. The heterologous domain may be followed by a polypurine rich domain. The 3' LTR can be derived from any number of retroviruses, typically an oncoretrovirus and preferably a mammalian oncoretrovirus. In one embodiment, the 3' LTR comprises a U3-R-U5 domain. In yet another embodiment the LTR comprises a sequence as set forth in SEQ ID NO:19 from about nucleotide 9405 to about 9998 or a sequence that is at least 95%, 98% or 99.5% (rounded to the nearest $10^{th}$) identical thereto.

The disclosure also provides a recombinant retroviral vector comprising from 5' to 3' a CMV-R-U5, fusion of the immediate early promoter from human cytomegalovirus to the MLV R-U5 region; a PBS, primer binding site for reverse transcriptase; a 5' splice site; a ψ packaging signal; a gag, ORF for MLV group specific antigen; a pol, ORF for MLV polymerase polyprotein; a 3' splice site; a 4070A env, ORF for envelope protein of MLV strain 4070A; an IRES, internal ribosome entry site of encephalomyocarditis virus; a modified cytosine deaminase (thermostabilized and codon optimized); a PPT, polypurine tract; and a U3-R-U5, MLV long terminal repeat. This structure is further depicted in FIG. 1.

The disclosure also provides a retroviral vector comprising a sequence as set forth in SEQ ID NO:19, 20, or 22.

In another embodiment, the disclosure provides a method of treating a subject having a cell proliferative disorder. The subject can be any mammal, and is preferably a human. The subject is contacted with a recombinant replication competent retroviral vector of the disclosure. The contacting can be in vivo or ex vivo. Methods of administering the retroviral vector of the disclosure are known in the art and include, for example, systemic administration, topical administration, intraperitoneal administration, intra-muscular administration, intracranial, cerebrospinal, as well as administration directly at the site of a tumor or cell-proliferative disorder. Other routes of administration known in the art.

Thus, the disclosure includes various pharmaceutical compositions useful for treating a cell proliferative disorder. The pharmaceutical compositions according to the disclosure are prepared by bringing a retroviral vector containing a heterologous polynucleotide sequence useful in treating or modulating a cell proliferative disorder according to the disclosure into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

For example, and not by way of limitation, a retroviral vector useful in treating a cell proliferative disorder will include an amphotropic ENV protein, GAG, and POL proteins, a promoter sequence in the U3 region retroviral genome, and all cis-acting sequence necessary for replication, packaging and integration of the retroviral genome into the target cell.

The following Examples are intended to illustrate, but not to limit the disclosure. While such Examples are typical of those that might be used, other procedures known to those skilled in the art may alternatively be utilized.

EXAMPLES

Example 1

Construction of Modified CD Genes and Insertion into Plasmid Vectors

Genetic enhancements to the wild type yeast cytosine deaminase gene have been made to include: (1) three positional mutations which change three amino acids (A23L, I140L and V108I) to increase thermal stability of the yeast cytosine deaminase protein and (2) additional gene sequence modifications to enhance human codon usage sequences to improve protein translation efficiency in human cells without further changes to the amino acid sequence.

Sequence design for CD included CD-optimized, CD-UPRT (+/−linker) and CD-OPRTase (+/−linker). The final cytosine deaminase coding sequence can comprise at the 5' end a PSI1 site (full length) and 3' end Not1 site plus poly A tail for PSI1/Not1 cassette based strategy.

The following sequence comprising a yeast cytosine deaminase was used for cloning, optimizing and mutation (the boxed nucleic acids comprise the restriction sites used in subsequent methods for cloning:

(SEQ ID NO: 30)
```
AACACGA TTATAA ATGGTGACAGGGGGAATGGCAAGCAAGTGGGATCAGAAGGGTATGGACATTGCCT

ATGAGGAGGCGGCCTTAGGTTACAAAGAGGGTGGTGTTCCTATTGGCGGATGTCTTATCAATAACAAA

GACGGAAGTGTTCTCGGTCGTGGTCACAACATGAGATTTCAAAAGGGATCCGCCACACTACATGGTGA

GATCTCCACTTTGGAAAACTGTGGGAGATTAGAGGGCAAAGTGTACAAAGATACCACTTTGTATACGA

CGCTGTCTCCATGCGACATGTGTACAGGTGCCATCATCATGTATGGTATTCCACGCTGTGTTGTCGGT

GAGAACGTTAATTTCAAAAGTAAGGGCGAGAAATATTTACAAACTAGAGGTCACGAGGTTGTTGTTGT

TGACGATGAGAGGTGTAAAAAGATCATGAAACAATTTATCGATGAAAGACCTCAGGATTGGTTTGAAG

ATATTGGTGAGTAG GCGGCCGC GCCATAGATAAAATAAAAGATTTTATTTAGTCTCCAGAAAAAGGGG

GG
```

The following Table summarizes the genes and resulting plasmid vectors that were made and their names.

TABLE

Vector constructs and names

| Identity Code | Reference name | Original Name | 5'LTR Prom | Envelope | Vector | IRES | Trans-gene | 3'LTR |
|---|---|---|---|---|---|---|---|---|
| T5.0000 | pACE-yCD | pACE-CD (Tai et al. 2005) | CMV | Ampho (4070A) | pACE | EMCV | Wt yeast CD | MLV U3 |
| T5.0001 | pAC3-yCD1 | CD-opt sequence | CMV | Ampho (4070A) | pAC3 | EMCV | modified CD | MLV U3 |
| T5.0002 | pAC3-yCD2 | CDopt + 3 pt | CMV | Ampho (4070A) | pAC3 | EMCV | Modified CD | MLV U3 |
| T5.0003 | pAC3-yCD2-U | Cdopt + 3 pt – UPRT | CMV | Ampho (4070A) | pAC3 | EMCV | CD2-UPRT | MLV U3 |
| T5.0004 | pAC3-yCD2-O | CDopt + 3 pt – OPRT | CMV | Ampho (4070A) | pAC3 | EMCV | CD2-OPRT | MLV U3 |
| T5.0005 | pAC3-yCD2-LO | CDopt + 3pt – LINK-OPRT | CMV | Ampho (4070A) | pAC3 | EMCV | CD2-L-OPRT | MLV U3 |
| T5.0006 | pAC3-eGFP | pAC3-emd, pAC3GFP | CMV | Ampho (4070A) | pAC3 | EMCV | Emera ld GFP | MLV U3 |
| T5.0007 | pAC3-yCD | pAC3-yCD | CMV | Ampho (4070A) | pAC3 | EMCV | Wt yeast CD | MLV U3 |

Figure 1B:
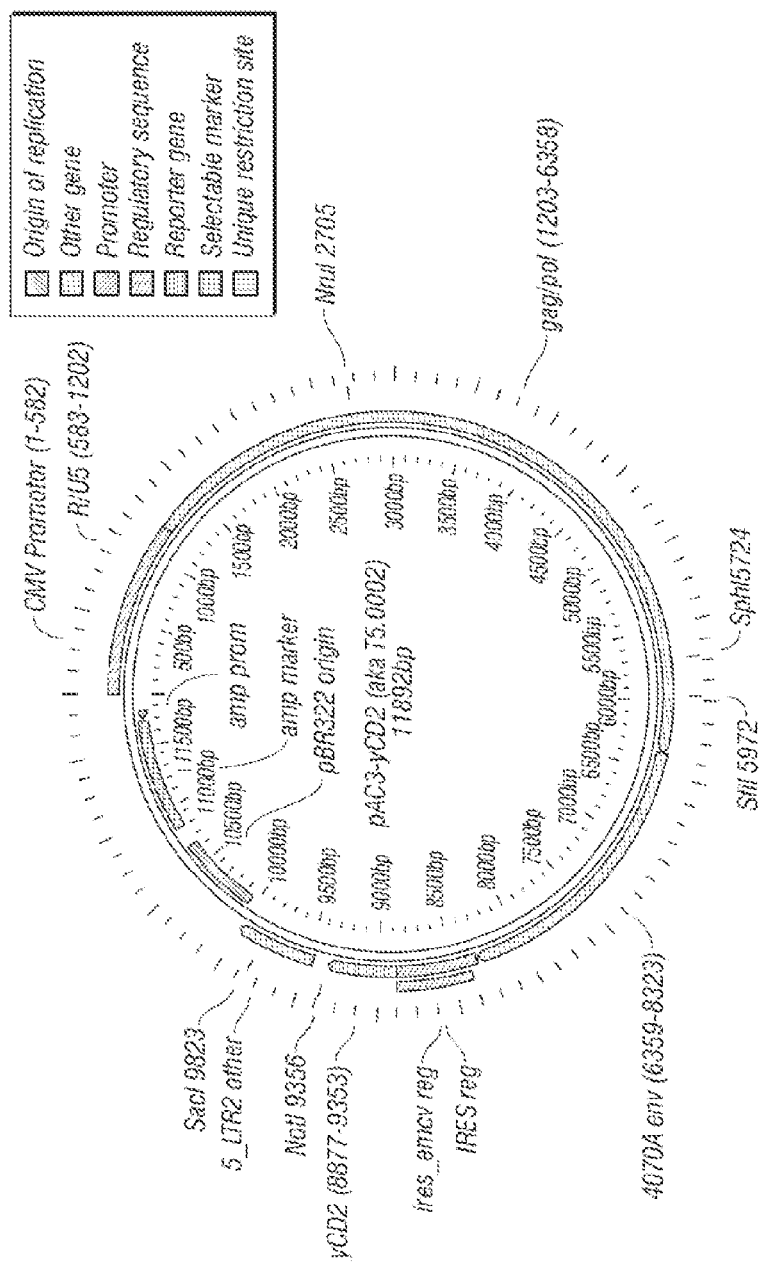
Figure 1C:
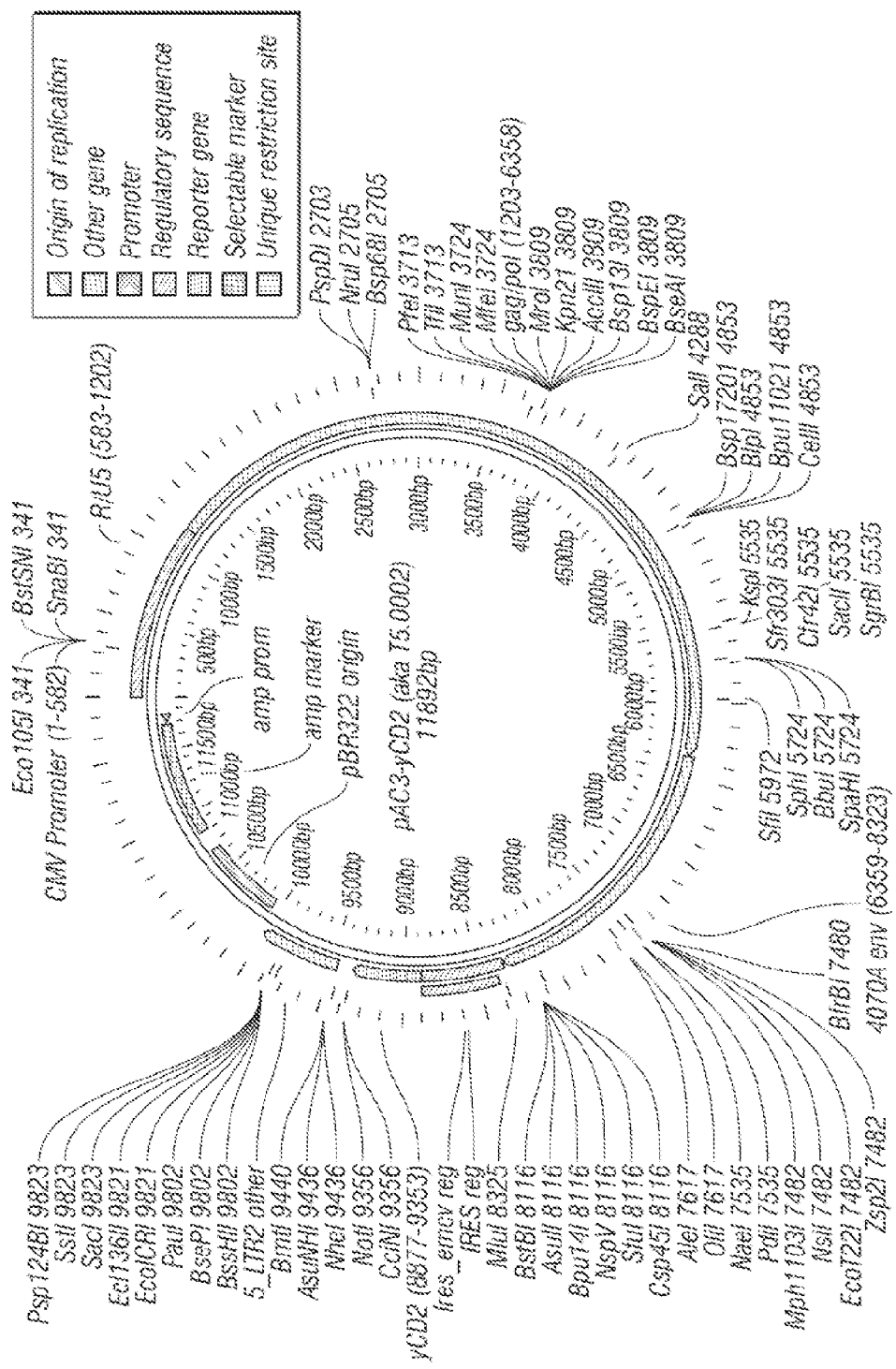
Figure 1D-4:
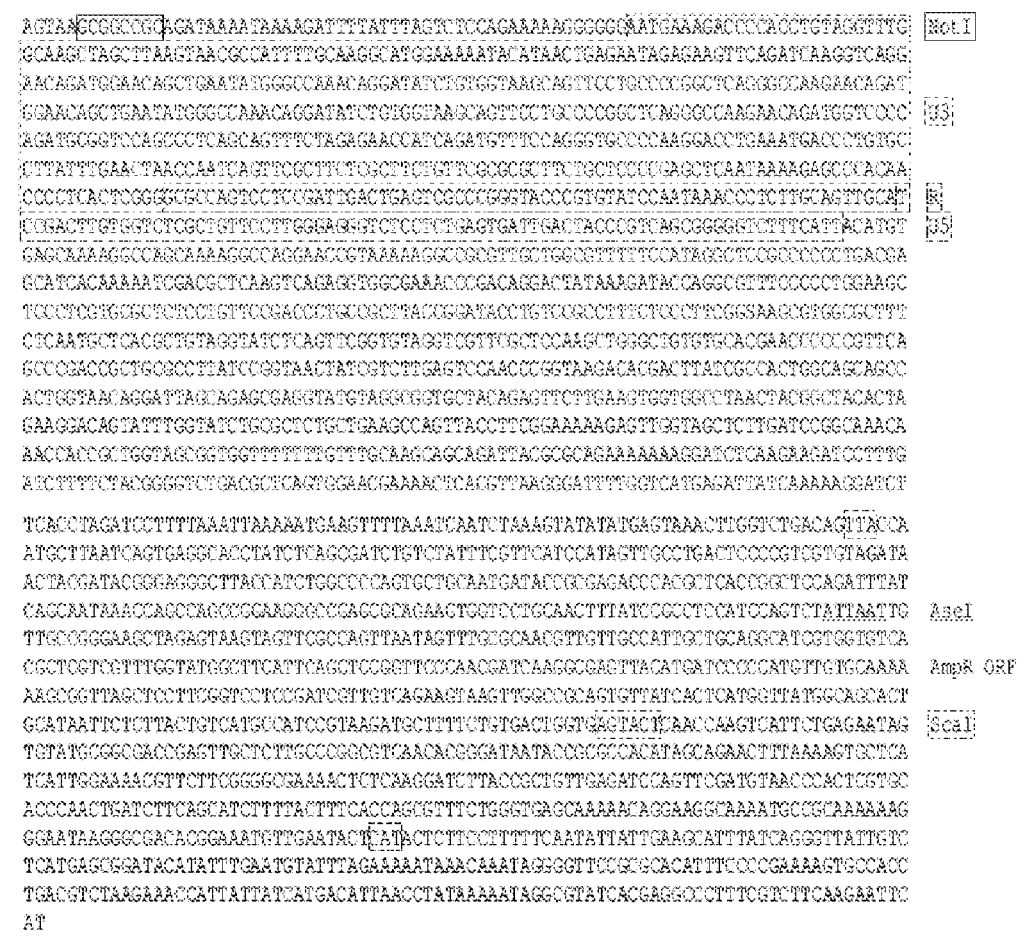

The replication competent retroviral vector described by Kasahara et al. pACE-CD (U.S. Pat. No. 6,899,871, the disclosure of which is incorporated herein) was used as a basis for additional modifications. A vector (pAC3-yCD) was modified to express a modified yeast cytosine deaminase gene as described herein and was used in the constructs. See 1A below for a diagram of the vector construct for the initial transfected replication-competent retrovirus. CMV is the human CMV immediate early promoter, U3, R and U5 are the corresponding regions of the viral long terminal repeat (LTR). Gag, pol and env are the viral protein coding regions. 1B and 1D shows the plasmid structure and a sequence of the disclosure. After the genes were synthesized at a contractor (Bio Basic Inc., Markham, Ontario, Canada) they were inserted into the Psi1-Not1 site of the pAC3 vector backbone (FIG. 1). The plasmid backbone was normally generated by cutting the plasmid pAC3-eGFP with Psi1 and NotI and purifying the large (about 11 kb) fragment encoding the plasmid and retroviral backbone)

A. Humanized Codon Optimized CD Gene (CD-opt, aka CD1, T5.0001).

A comparison of a human codon optimized cytosine deaminase of Conrad et al. and PCT WO 99/60008 indicates 91 total codons optimized in both, 36 codons identical, 47 codons had third base pair changes (all encode same amino acid) and 9 codons were different (however they encoded same amino acid). Of the 9 codons that differed:

AGC (Ser) to TCC (Ser)

CGT (Arg) to AGG (Arg)

CCA (Pro) to CCT (Pro)

All have equivalent GC content and encode the same amino acid. The native yeast gene sequence above was separately codon optimized to give the following CD gene (CD1) and was called T5.0001 when inserted into the plasmid vector pAC3 which encodes the replication competent retrovirus (RCR) with IRES.

(SEQ ID NO: 31)

```
TTATAAATGGTGACCGGCGGCATGGCCTCCAAGTGGGATCAAAAGGGCATGGATATCGCTTA
CGAGGAGGCCGCCCTGGGCTACAAGGAGGGCGGCGTGCCTATCGGCGGCTGTCTGATCAACA
ACAAGGACGGCAGTGTGCTGGGCAGGGGCCACAACATGAGGTTCCAGAAGGGCTCCGCCACC
CTGCACGGCGAGATCTCCACCCTGGAGAACTGTGGCAGGCTGGAGGGCAAGGTGTACAAGGA
CACCACCCTGTACACCACCCTGTCCCCTTGTGACATGTGTACCGGCGCTATCATCATGTACG
GCATCCCTAGGTGTGTGGTGGGCGAGAACGTGAACTTCAAGTCCAAGGGCGAGAAGTACCTG
CAAACCAGGGGCCACGAGGTGGTGGTTGTTGACGATGAGAGGTGTAAGAAGATCATGAAGCA
GTTCATCGACGAGAGGCCTCAGGACTGGTTCGAGGATATCGGCGAGTGATAAGCGGCCGCAG
ATAAAATAAAGATTTTATTTAGTCTCCAGAAAAAGGGGGG.
```

B. Heat Stabilized CD Gene.

Additional modifications were made to enhance the stability of the cytosine deaminase. Genetic enhancements to the wild type yeast cytosine deaminase gene were made to include three positional mutations which change three amino acids (A23L, I140L and V108I) to increase thermal stability of the yeast cytosine deaminase protein.

The following primer pairs were used in the generation of the gene for the cytosine deaminase polypeptide of the disclosure:

sense:
(SEQ ID NO: 32)
5'-tcgaggatatcggcgagtgaaacccgttattcttttggc-3' antisense:
(SEQ ID NO: 33)
5'-gccaaaaagaataacgggtttcactcgccgatatcctcga-3' sense:
(SEQ ID NO: 34)
5'tcggcgagtgatccggcggcggcgcctccggcggcggcgcctccggcg gcggcgcctccggcggcggcgccaacccgttatt-3' antisense:
(SEQ ID NO: 35)
5'-aataacggttggcgccgccgccggaggcgccgccgccggaggcgcc gccgccggaggcgccgccgccggatcactcgccga-3'

To increase the stability of the native yeast CD, three amino acid substitutions were engineered into the protein. These substitutions were alone or in combination with human codon optimization.

The three amino acid substitutions are: A23L, V108I, I140L. A sequence encoding these substitutions is shown below.

(SEQ ID NO: 36)
ATGGTGACAGGGGGAATGGCAAGCAAGTGGGATCAGAAGGGTATGGACATTGCCTATGAGGA

GGCGTTATAGGTTACAAAGAGGGTGGTGTTCCTATTGGCGGATGTCTTATCAATAACAAAG

ACGGAAGTGTTCTCGGTCGTGGTCACAACATGAGATTTCAAAAGGGATCCGCCACACTACAT

GGTGAGATCTCCACTTTGGAAAACTGTGGGAGATTAGAGGGCAAAGTGTACAAAGATACCAC

TTTGTATACGACGCTGTCTCCATGCGACATGTGTACAGGTGCCATCATCATGTATGGTATTC

CACGCTGTGTCATCGGTGAGAACGTTAATTTCAAAAGTAAGGGCGAGAAATATTTACAAACT

AGAGGTCACGAGGTTGTTGTTGTTGACGATGAGAGGTGTAAAAAGTTAATGAAACAATTTAT

CGATGAAAGACCTCAGGATTGGTTTGAAGATATTGGTGAGTAG[GCGGCCGC]GCCATAGATAA

AATAAAAGATTTTATTTAGTCTCCAGAAAAAGGGGGG

The encoded polypeptide comprises the following sequence (substituted amino acids bold-underlined):

(SEQ ID NO: 4)
1 MVTGGMASKWDQKGMDIAYEEALLGYKEGGVPIGGCLINNKDGSVLGRGHNMRFQKGSAT

61 LHGEISTLENCGRLEGKVYKDTTLYTTLSPCDMCTGAIIMYGIPRCVIGENVNFKSKGEK

121 YLQTRGHEVVVVDDERCKKLMKQFIDERPQDWFEDIGE-

Final construct design that integrates 3 amino acid substitutions A23L/V108I/I140L utilizing preferred codons and uses preferred human codon usage for entire sequence (this gene is called CDopt+3pt [aka CD2] and T5.0002 when inserted into the plasmid vector pAC3 which encodes the RCR with IRES) (SEQ ID NO:37):

```
  1 ATGGTGACCGGCGGCATGGCCTCCAAGTGGGATCAAAAGGGCATGGATATCGCTTACGAG

61 GAGGCCCTGCTGGGCTACAAGGAGGGCGGCGTGCCTATCGGCGGCTGTCTGATCAACAAC

121 AAGGACGGCAGTGTGCTGGGCAGGGGCCACAACATGAGGTTCCAGAAGGGCTCCGCCACC

181 CTGCACGGCGAGATCTCCACCCTGGAGAACTGTGGCAGGCTGGAGGGCAAGGTGTACAAG

241 GACACCACCCTGTACACCACCCTGTCCCCTTGTGACATGTGTACCGGCGCTATCATCATG

301 TACGGCATCCCTAGGTGTGTGATCGGCGAGAACGTGAACTTCAAGTCCAAGGGCGAGAAG

361 TACCTGCAAACCAGGGGCCACGAGGTGGTGGTTGTTGACGATGAGAGGTGTAAGAAGCTG

421 ATGAAGCAGTTCATCGACGAGAGGCCTCAGGACTGGTTCGAGGATATCGGCGAGTGATAA
```

CD-optimized sequence design (human codon preference+3 amino acid substitutions)

Underlined codons denotes preferred codons for amino acid substitutions.

(SEQ ID NO: 38)
```
AACACGATTATAAATGGTGACCGGCGGCATGGCCTCCAAGTGGGATCAAAAGGGCATGGATA

TCGCTTACGAGGAGGCCCTGCTGGGCTACAAGGAGGGCGGCGTGCCTATCGGCGGCTGTCTG

ATCAACAACAAGGACGGCAGTGTGCTGGGCAGGGGCCACAACATGAGGTTCCAGAAGGGCTC

CGCCACCCTGCACGGCGAGATCTCCACCCTGGAGAACTGTGGCAGGCTGGAGGGCAAGGTGT

ACAAGGACACCACCCTGTACACCACCCTGTCCCCTTGTGACATGTGTACCGGCGCTATCATC

ATGTACGGCATCCCTAGGTGTGTGATCGGCGAGAACGTGAACTTCAAGTCCAAGGGCGAGAA

GTACCTGCAAACCAGGGGCCACGAGGTGGTGGTTGTTGACGATGAGAGGTGTAAGAAGCTGA

TGAAGCAGTTCATCGACGAGAGGCCTCAGGACTGGTTCGAGGATATCGGCGAGTAAGCGGCC

GCGCCATAGATAAAATAAAAGATTTTATTTAGTCTCCAGAAAAAGGGGGG
```

Construction of CD-UPRT Fusion Gene (CDopt+3pt-UPRT, [aka CD-opt-UPRT and CD2-UPRT], T5.0003 in the pAC3 Plasmid RCR Vector).

Figure 2B:
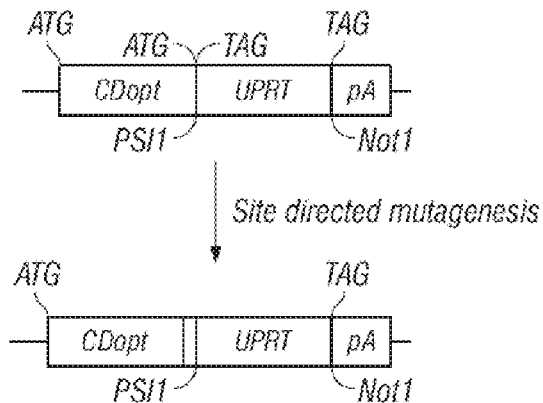

A fusion construct was also developed comprising a CD polypeptide as described above linked to a UPRT polypeptide to generate a CD-optimized-UPRT sequence using Scheme I as set forth in FIG. 2A. The following primers were used to delete the stop-start between the CD and UPRT.

Primer Sequences:

| Primer Name | Primer Sequence (5' to 3') (SEQ ID NO:) |
|---|---|
| del118-123 | 5'-tcgaggatatcggcgagtgaaacccgttattcttttggc-3' (39) |
| del118-123-antisense | 5'-gccaaaagaataacgggtttcactcgccgatatcctcga-3' (40) |

| Primer Name | Length (nt.) | Tm | Duplex Energy at 68° C. | Energy Cost of Mismatches |
|---|---|---|---|---|
| del118-123 | 40 | 79.06° C. | -44.37 kcal/mole | 21.1% |
| del118-123-antisense | 40 | 79.06° C. | -47.95 kcal/mole | 20.3% |

| Primer Name | Primer-Template Duplex |
|---|---|
| del118-123 (SEQ ID NO: 39 and 41, respectively) | 5'-tcgaggatatcggcgagtga------aacccgttattcttttggc-3'<br>   \|\|\|\|\|\|\|\|\|\|\|\|\|\|\|\|\|\|\|       \|\|\|\|\|\|\|\|\|\|\|\|\|\|\|\|\|\|\|<br>ccaagctcctatagccgctcactatctacttgggcaataagaaaaaccgaag |
| del118-123-antisense (SEQ ID NO: 40 and 42 respectively) | ggttcgaggatatcggcgagtgatagatgaacccgttattcttttggcttc<br>     \|\|\|\|\|\|\|\|\|\|\|\|\|\|\|\|\|\|\|       \|\|\|\|\|\|\|\|\|\|\|\|\|\|\|\|\|\|\|<br>3'-agctcctatagccgctcact------ttgggcaataagaaaaaccg |

The resulting fusion polynucleotide comprises 1296 bp and the sequence set forth immediately below:

(SEQ ID NO: 43)
```
AACACGATTATAAATGGTGACCGGCGGCATGGCCTCCAAGTGGGATCAAAAGGGCATGGATATCGCTT
ACGAGGAGGCCCTGCTGGGCTACAAGGAGGGCGGCGTGCCTATCGGCGGCTGTCTGATCAACAACAAG
GACGGCAGTGTGCTGGGCAGGGGCCACAACATGAGGTTCCAGAAGGGCTCCGCCACCCTGCACGGCGA
GATCTCCACCCTGGAGAACTGTGGCAGGCTGGAGGGCAAGGTGTACAAGGACACCACCCTGTACACCA
CCCTGTCCCCTTGTGACATGTGTACCGGCGCTATCATCATGTACGGCATCCCTAGGTGTGTGATCGGC
GAGAACGTGAACTTCAAGTCCAAGGGCGAGAAGTACCTGCAAACCAGGGGCCACGAGGTGGTGGTTGT
TGACGATGAGAGGTGTAAGAAGCTGATGAAGCAGTTCATCGACGAGAGGCCTCAGGACTGGTTCGAGG
ATATCGGCGAGAACCCGTTATTCTTTTTGGCTTCTCCATTCTTGTACCTTACATATCTTATATATTAT
CCAAACAAAGGGTCTTTCGTTAGCAAACCTAGAAATCTGCAAAAAATGTCTTCGGAACCATTTAAGAA
CGTCTACTTGCTACCTCAAACAAACCAATTGCTGGGTTTGTACACCATCATCAGAAATAAGAATACAA
CTAGACCTGATTTCATTTTCTACTCCGATAGAATCATCAGATTGTTGGTTGAAGAAGGTTTGAACCAT
CTACCTGTGCAAAAGCAAATTGTGGAAACTGACACCAACGAAAACTTCGAAGGTGTCTCATTCATGGG
TAAAATCTGTGGTGTTTCCATTGTCAGAGCTGGTGAATCGATGGAGCAAGGATTAAGAGACTGTTGTA
GGTCTGTGCGTATCGGTAAAATTTTAATTCAAAGGGACGAGGAGACTGCTTTACCAAAGTTATTCTAC
GAAAAATTACCAGAGGATATATCTGAAAGGTATGTCTTCCTATTAGACCCAATGCTGGCCACCGGTGG
TAGTGCTATCATGGCTACAGAAGTCTTGATTAAGAGAGGTGTTAAGCCAGAGAGAATTTACTTCTTAA
ACCTAATCTGTAGTAAGGAAGGGATTGAAAAATACCATGCCGCCTTCCCAGAGGTCAGAATTGTTACT
GGTGCCCTCGACAGAGGTCTAGATGAAAACAAGTATCTAGTTCCAGGGTTGGGTGACTTTGGTGACAG
ATACTACTGTGTTTAAGCGGCCGCGCCATAGATAAAATAAAAGATTTTATTTAGTCTCCAGAAAAAGG
GGGG
```

Construction of CD-Linker UPRT Fusion Gene (CDopt+3pt-LINK-UPRT [aka CD-opt-LINKER-UPRT and CD2-L-UPRT]).

A fusion construct was also developed by cloning a linker (Ser-Gly-Gly-Gly-Gly)$_4$ domain between and in frame with the CD polypeptide and the UPRT polypeptide to generate a CD-optimized-linker-UPRT sequence using Scheme II as depicted in 2B. The following primers were used to insert the linker.

| Primer Name | Primer Sequence (5' to 3') (SEQ ID NO:) |
|---|---|
| ins_60nt_after_477 | 5'-tcggcgagtgatccggcggcggcgcctccggcggcggcgcctccggcgcggcgcctccggcggcggcgccaacccgttatt-3' (44) |
| ins_60nt_after_477-antisense | 5'-aataacgggttggcgccgccgccggaggcgccgccgccggaggcgccgccgccggaggcgccgccgccggatcactcgccga-3' (45) |

| Primer Name | Length (nt.) | Tm | Duplex Energy at 68° C. | Energy Cost of Mismatches |
|---|---|---|---|---|
| ins_60nt_after_477 | 82 | 79.77° C. | -30.19 kcal/mole | 83.3% |
| ins_60nt_after_477-antisense | 82 | 79.77° C. | -32.31 kcal/mole | 82.2% |

The resulting construct has size: 1356 bp and the sequence immediately below:

(SEQ ID NO: 46)

AACACGA`TTATAA`ATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

GACGGCAGTGTGCTGGGCAGGGGCCACAACATGAGGTTCCAGAAGGGCTCCGCCACCCTGCACGGCGA

GATCTCCACCCTGGAGAACTGTGGCAGGCTGGAGGGCAAGGTGTACAAGGACACCACCCTGTACACCA

CCCTGTCCCCTTGTGACATGTGTACCGGCGCTATCATCATGTACGGCATCCCTAGGTGTGTGATCGGC

GAGAACGTGAACTTCAAGTCCAAGGGCGAGAAGTACCTGCAAACCAGGGGCCACGAGGTGGTGGTTGT

TGACGATGAGAGGTGTAAGAAGCTGATGAAGCAGTTCATCGACGAGAGGCCTCAGGACTGGTTCGAGG

ATATCGGCGAGTCCGGCGGCGGCGCCTCCGGCGGCGGCGCCTCCGGCGGCGGCGCCTCCGGCGGCGGC

GCCAACCCGTTATTCTTTTTGGCTTCTCCATTCTTGTACCTTACATATCTTATATATTATCCAAACAA

AGGGTCTTTCGTTAGCAAACCTAGAAATCTGCAAAAAATGTCTTCGGAACCATTTAAGAACGTCTACT

TGCTACCTCAAACAAACCAATTGCTGGGTTTGTACACCATCATCAGAAATAAGAATACAACTAGACCT

GATTTCATTTTCTACTCCGATAGAATCATCAGATTGTTGGTTGAAGAAGGTTTGAACCATCTACCTGT

GCAAAAGCAAATTGTGGAAACTGACACCAACGAAAACTTCGAAGGTGTCTCATTCATGGGTAAAATCT

GTGGTGTTTCCATTGTCAGAGCTGGTGAATCGATGGAGCAAGGATTAAGAGACTGTTGTAGGTCTGTG

CGTATCGGTAAAATTTTAATTCAAAGGGACGAGGAGACTGCTTTACCAAAGTTATTCTACGAAAAATT

ACCAGAGGATATATCTGAAAGGTATGTCTTCCTATTAGACCCAATGCTGGCCACCGGTGGTAGTGCTA

TCATGGCTACAGAAGTCTTGATTAAGAGAGGTGTTAAGCCAGAGAGAATTTACTTCTTAAACCTAATC

TGTAGTAAGGAAGGGATTGAAAAATACCATGCCGCCTTCCCAGAGGTCAGAATTGTTACTGGTGCCCT

CGACAGAGGTCTAGATGAAAACAAGTATCTAGTTCCAGGGTTGGGTGACTTTGGTGACAGATACTACT

GTGTTTAA`GCGGCCGC`GCCATAGATAAAATAAAAGATTTTATTTAGTCTCCAGAAAAAGGGGGG

Construction of CD-OPRT Fusion Gene (CDopt+3pt-OPRT [aka CD-opt-OPRT and CD2-OPRT], T5.0004 when Inserted into the pAC3 Plasmid RCR Vector).

Figure 2C:
Figure 2C:
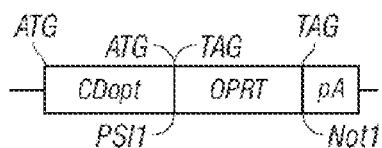
Figure 2C:
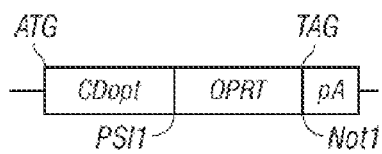

A fusion construct was also developed comprising a CD polypeptide as described above linked to an OPRT polypeptide to generated a CD-optimized-OPRTase (CD humanized+3ptmutation+OPRTase functional domain human) using Scheme III as shown in FIG. 2C.

The resulting construct comprises a size of 1269 bp and the sequence immediately below:

(SEQ ID NO: 47)

AACACGA`TTATAA`ATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

GACGGCAGTGTGCTGGGCAGGGGCCACAACATGAGGTTCCAGAAGGGCTCCGCCACCCTGCACGGCGA

GATCTCCACCCTGGAGAACTGTGGCAGGCTGGAGGGCAAGGTGTACAAGGACACCACCCTGTACACCA

CCCTGTCCCCTTGTGACATGTGTACCGGCGCTATCATCATGTACGGCATCCCTAGGTGTGTGATCGGC

GAGAACGTGAACTTCAAGTCCAAGGGCGAGAAGTACCTGCAAACCAGGGGCCACGAGGTGGTGGTTGT

TGACGATGAGAGGTGTAAGAAGCTGATGAAGCAGTTCATCGACGAGAGGCCTCAGGACTGGTTCGAGG

ATATCGGCGAGGCGGTCGCTCGTGcagctttggggccattggtgacgggtctgtacgacgtgcaggct ttcaagtttggggacttcgtgctgaagagcgggctttcctcccccatctacatcgatctgcggggcat cgtgtctcgaccgcgtcttctgagtcaggttgcagatattttattccaaactgcccaaaatgcaggca tcagttttgacaccgtgtgtggagtgccttatacagctttgccattggctacagttatctgttcaacc aatcaaattccaatgcttattagaaggaaagaaacaaaggattatggaactaagcgtcttgtagaagg

```
aactattaatccaggagaaacctgtttaatcattgaagatgttgtcaccagtggatctagtgttttgg aaactgttgaggttcttcagaaggagggcttgaaggtcactgatgccatagtgctgttggacagagag cagggaggcaaggacaagttgcaggcgcacgggatccgcctccactcagtgtgtacattgtccaaaat gctggagattctcgagcagcagaaaaaagttgatgctgagacagttgggagagtgaagaggtttattc aggagaatgtctttgtggcagcgaatcataatggttctcccctttctataaaggaagcacccaaagaa ctcaGCTTCGGTGCACGTGCAGAGCTGCCCAGGATCCACCCAGTTGCATCGAAGTAAGCGGCCGCGCC

ATAGATAAAATAAAAGATTTTATTTAGTCTCCAGAAAAAGGGGGG
```

Construction of CD-Linker-OPRT Fusion Gene (CDopt+ 3pt-LINK-OPRT, [aka CD-opt-LINKER-OPRT and CD2-L-OPRT], T5.0005 in the pAC3 Plasmid RCR Vector).

Figure 2D:
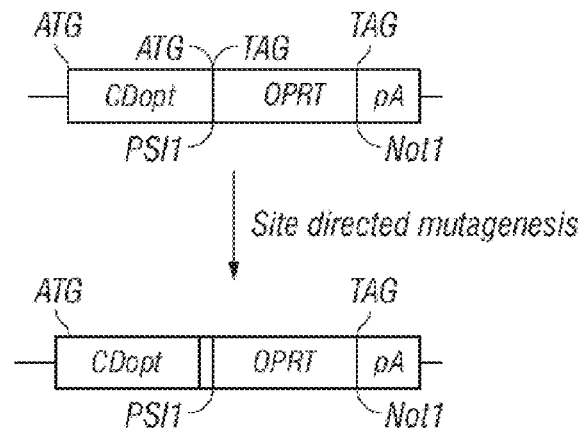

A fusion construct was also developed by cloning a linker (Ser-Gly-Gly-Gly-Gly)$_4$ (SEQ ID NO:24) domain between and in frame with the CD polypeptide and the OPRT polypeptide to generated a CD-optimized-linker-OPRT sequence using Scheme IV as shown in FIG. 2D.

The resulting construct comprises a size of 1329 bp and the sequence immediately below:

generated other methods of production can be implemented by those skilled in the art. Vector particles were generated by transient transfection of 293T cells (Pear et al. Proc Natl Acad Sci USA. 90:8392-8396 1993). The 293T cells were thawed and put into culture, then passaged twice in T-75 flasks containing 15 mL of the DMEM medium that was prepared by mixing DMEM High Glucose medium (Hyclone#30081, 500 mL) with FBS (Hyclone#SH30070, 50 mL), L-Glutamine (Cellgro#25-005-CI, 5 mL), NEAA (Hyclone #SH30238, 5 mL), and Penicillin-strep (Cellgro#30-002-CI, 5 mL). The

```
                                                                     (SEQ ID NO: 48)
AACACGATTTATAAATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

GACGGCAGTGTGCTGGGCAGGGGCCACAACATGAGGTTCCAGAAGGGCTCCGCCACCCTGCACGGCGA

GATCTCCACCCTGGAGAACTGTGGCAGGCTGGAGGGCAAGGTGTACAAGGACACCACCCTGTACACCA

CCCTGTCCCCTTGTGACATGTGTACCGGCGCTATCATCATGTACGGCATCCCTAGGTGTGTGATCGGC

GAGAACGTGAACTTCAAGTCCAAGGGCGAGAAGTACCTGCAAACCAGGGGCCACGAGGTGGTGGTTGT

TGACGATGAGAGGTGTAAGAAGCTGATGAAGCAGTTCATCGACGAGAGGCCTCAGGACTGGTTCGAGG

ATATCGGCGAGTCCGGCGGCGGCGCCTCCGGCGGCGGCGCCTCCGGCGGCGGCGCCTCCGGCGGCGGC

GCCGCGGTCGCTCGTGcagctttggggccattggtgacgggtctgtacgacgtgcaggctttcaagtt tggggacttcgtgctgaagagcgggctttcctcccccatctacatcgatctgcggggcatcgtgtctc gaccgcgtcttctgagtcaggttgcagatattttattccaaactgcccaaaatgcaggcatcagtttt gacaccgtgtgtggagtgccttatacagctttgccattggctacagttatctgttcaaccaatcaaat tccaatgcttattagaaggaaagaaacaaaggattatggaactaagcgtcttgtagaaggaactatta atccaggagaaacctgtttaatcattgaagatgttgtcaccagtggatctagtgttttggaaactgtt gaggttcttcagaaggagggcttgaaggtcactgatgccatagtgctgttggacagagagcagggagg caaggacaagttgcaggcgcacgggatccgcctccactcagtgtgtacattgtccaaaatgctggaga ttctcgagcagcagaaaaaagttgatgctgagacagttgggagagtgaagaggtttattcaggagaat gtctttgtggcagcgaatcataatggttctcccctttctataaaggaagcacccaaagaactcaGCTT

CGGTGCACGTGCAGACTGCCCAGGATCCACCCAGTTGCATCGAAGTAAGCGGCCGCGCCATAGATAA

AATAAAAGATTTTATTTAGTCTCCAGAAAAAGGGGGG.
```

Example 2

Infectious Vector Production

Vector can be produced in a number of ways, but the first step is to introduce the plasmid DNA vector into cells to allow production of infectious particles, that can then be harvested from the cell supernatant. Once infectious particles have been flasks were incubated at 37° C. and 5% CO2. After the 3$^{rd}$ passage cells were seeded in 6 T-25's, each containing 5 mL of the medium, at a cell density of 1.8×10$^6$ cells/T-25 (or 7.2×10$^4$ cells/cm$^2$). One day after seeding the T-25's, the cells were transfected with the T5.0002 plasmid that expressed the viral vector using the Calcium Phosphate Transfection Kit from Promega (Cat#E1200). Eighteen hours following transfection, the media in one set of the flasks (3 flasks each set)

were replaced with fresh medium containing 10 mM NaB. The media in the $2^{nd}$ set of the flasks were not replaced, which served as a control (zero NaB). Eight hours post NaB treatment, the media in all flasks were replaced with the fresh medium containing no NaB. The expression was allowed to continue for both sets of flasks until the next day (22 hours duration). The supernatants from both sets of flasks were harvested and assayed for their titers by qPCR expressed in Transducing Units (TU)/ml (see example 3).

The titer results are shown in the following table.

| Condition | First titer | Second titer (after storing at −80° C. for 68 days) |
|---|---|---|
| Without NaB | 1.5 (±0.05) × $10^6$ TU/mL | 1.2 (±0.2) × $10^6$ TU/mL |
| 10 mM NaB | 1.4 (±0.3) × $10^6$ TU/mL | 7.0 (±0.14) × $10^5$ TU/mL |

Subsequent vector preparations were produced in this manner, without sodium butyrate. The other vector plasmids have been used in the same way to generate vector preparations with titers between 10e5 TU/ml and 10e7 TU/ml. Such material can be further purified and concentrated, if desired, as described below and see also: U.S. Pat. No. 5,792,643; T. Rodriguez et al. J Gene Med 9:233 2007; see, e.g., International Application No. PCT/US10/38996, the disclosure of which is incorporated herein by reference. In certain embodiments of the disclosure the dosing was calculated by grams of brain weight. In such embodiments, the dosing of a replication competent retroviral vector of the disclosure useful in the methods for treatment can range from $10^3$ to $10^7$ TU per gram brain weight.

Example 3

Quantitative PCR Titering Assay

The functional vector concentration, or titer, is determined using a quantitative PCR-based (qPCR) method. In this method, vector is titered by infecting a transducible host cell line (e.g. PC-3 human prostatic carcinoma cells, ATCC Cat#CRL-1435) with a standard volume of vector and measuring the resulting amount of provirus present within the host cells after transduction. The cells and vector are incubated under standard culturing condition (37° C., 5% CO2) for 24 hr to allow for complete infection prior to the addition of the anti-retroviral AZT to stop vector replication. Next, the cells are harvested from the culture dish and the genomic DNA (gDNA) is purified using an Invitrogen Purelink gDNA purification kit and eluted from the purification column with sterile RNase-/DNase-free water. The A260/A280 absorbance ratio is measured on a spectrophotometer to determine the concentration and relative purity of the sample. The gDNA concentrations are normalized with additional RNase-/DNase-free water to the lowest concentration of any given set of gDNA preparations such that the input DNA for the qPCR is constant for all samples analyzed. Genomic DNA purity is further assessed by electrophoresis of an aliquot of each sample on an ethidium bromide stained 0.8% agarose gel. If the sample passes an A260/A280 absorbance range of 1.8-2.0 and shows a single band of gDNA, then the sample is ready for qPCR analysis of provirus copy number of the vector. Using primers that interrogate the LTR region of the provirus (reverse-transcribed vector DNA and vector DNA that is integrated into the host gDNA), qPCR is performed to estimate the total number of transduction events that occurred when the known volume of vector was used to transduce the known number of cells. The number of transduction events per reaction is calculated from a standard curve that utilizes a target-carrying plasmid of known copy-number that is serial diluted from 1E7 to 1E1 copies and measured under identical qPCR conditions as the samples. Knowing how many genomic equivalents were used for each qPCR reaction (from the concentration previously determined) and how many transduction events that occurred per reaction, we determine the total number of transduction events that occurred based on the total number of cells that were present at the time of transduction. This value is the titer of the vector after dilution into the medium containing the cells during the initial transduction. To calculate the corrected titer value, the dilution is corrected for by multiplying through by the volume of culture and the volume of titer divided by the volume of titer. These experiments are performed in replicate cultures and analyzed by qPCR using triplicate measurements for each condition to determine an average titer and with its associated standard deviation and coefficient of variance.

Example 4

Expression Levels Measured by Western Blot

Figure 3:
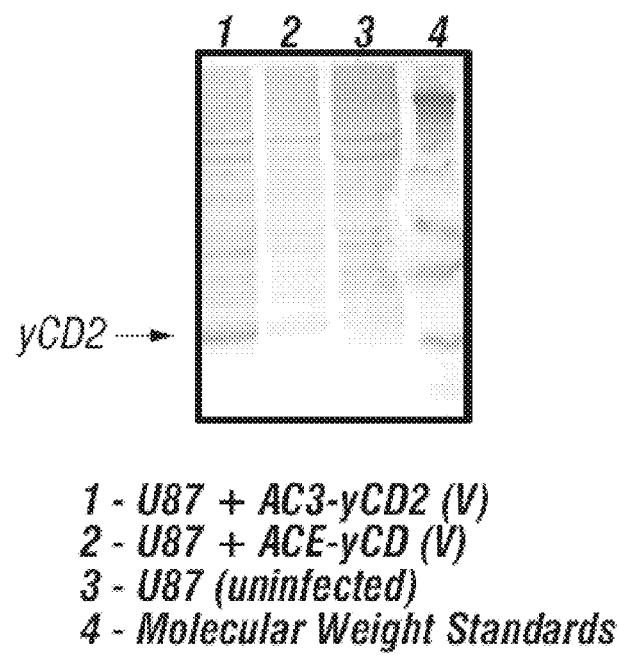
FIG. 3 shows that higher levels of yCD2 protein are observed compared to wild type yCD protein in infected U-87 cells.

FIG. 3 demonstrates that higher levels of the human codon optimized with the three mutations for higher stability are observed compared to wild type yCD protein in a Western blot analysis of U-87 cells infected with virus encoding either the wild type (ACE-yCD) or fully optimized (AC3-yCD2) cytosine deaminase genes.

Example 5

Genetic Stability of Viral Vectors

Figure 4:
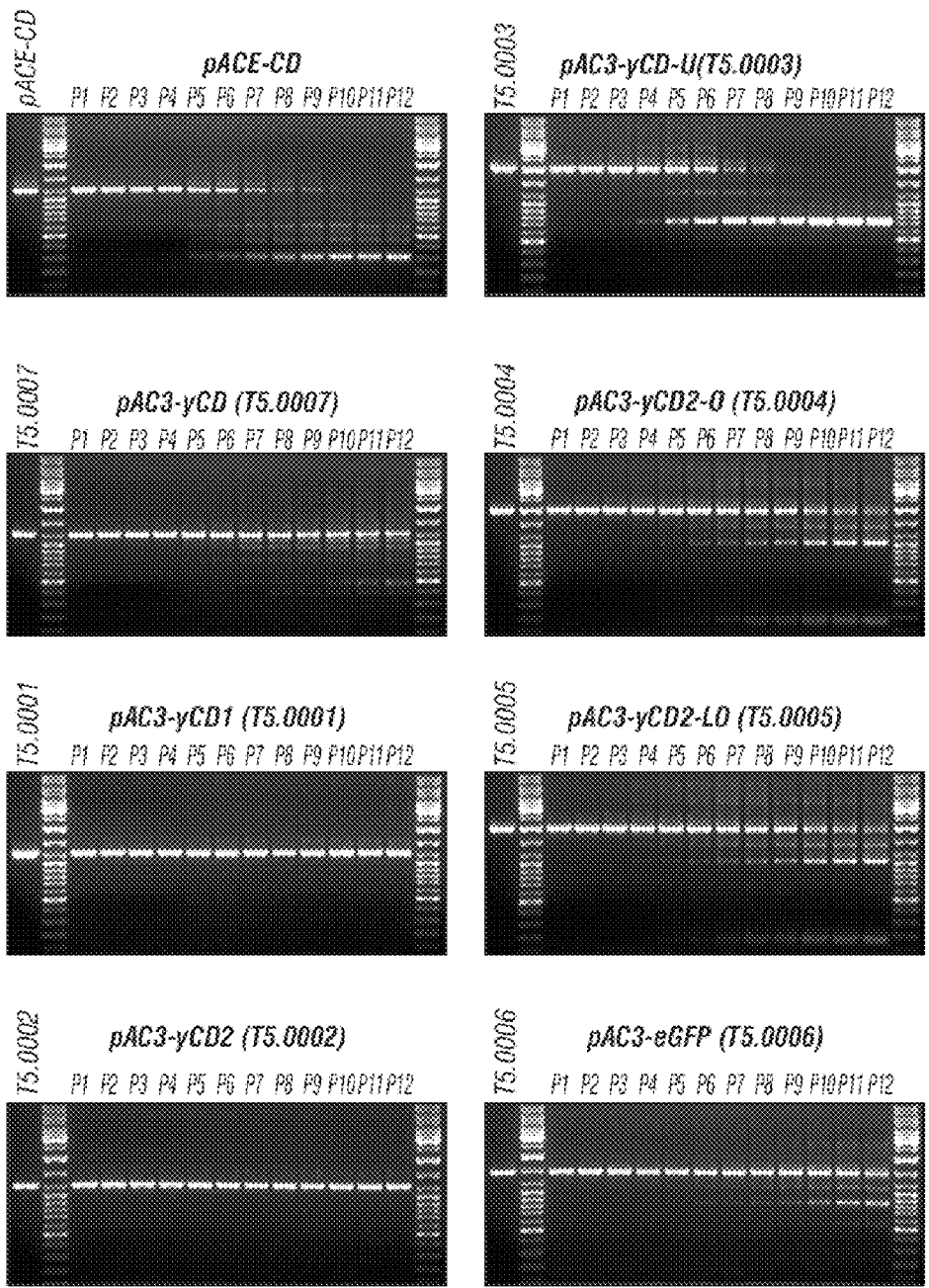
FIG. 4 shows the stability of a vector comprising a CD polypeptide of the disclosure and the comparison to other vectors of the disclosure.

It is recognized that after reverse transcription and the first integration event into treated cells, the DNA provirus and any subsequent progeny retrovirus has a conventional LTR structure from MLV on either end. This configuration has been shown to be stable after multiple cycles of infection (See FIG. 4 below).

Approximately $10^6$ naïve U-87 cells were initially infected with the viral vector at an MI of 0.01, and grown until fully infected to complete a single cycle of infection. Supernatant is then repassed onto uninfected cells and the cycle repeated. Genomic stability of the yCD2 sequence was assessed by PCR amplification of the integrated provirus from the infected cells using MLV specific primers flanking the transgene insertion site. For each set of infections, amplification of the vector plasmid (pAC3-yCD2 and the Kasahara et al. vector pACE-CD) was also performed to track full-length amplicon sizing on the gel. The appearance of any bands smaller than full-length amplicon would be an indicator of vector instability. Such experiments demonstrated that a vector of the disclosure (T5.0002—comprising the modified vector and CDopt+3pt (CD2) heterologous polynucleotide maintained stability for more passages than pACE-CD or T5.007 both of which carry the wild type yeast.

Example 6

Cell Killing Experiments

Figure 5A:
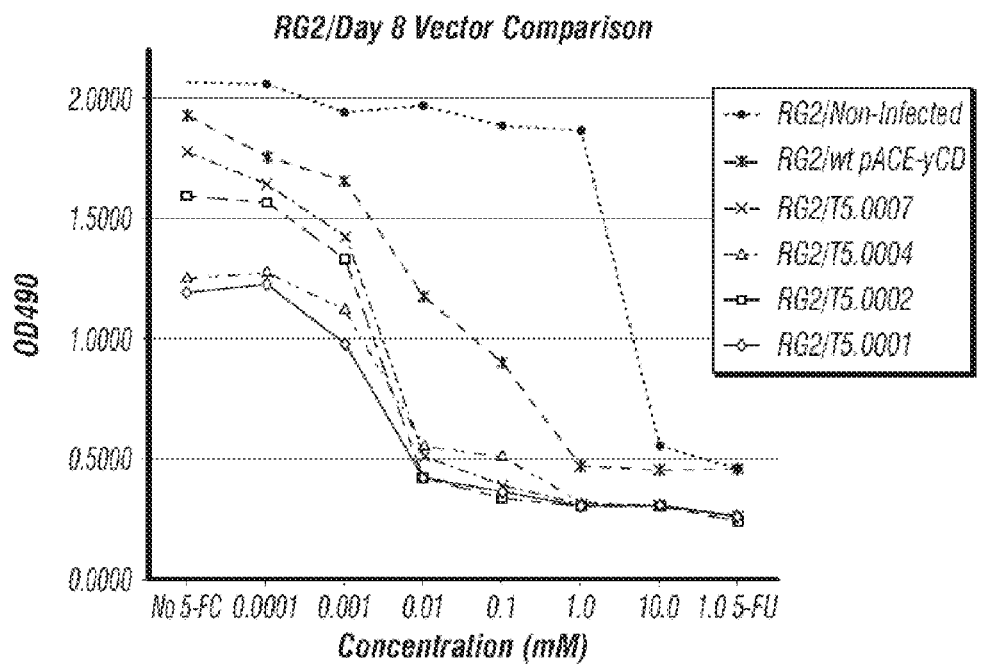
FIG. 5A-B show that a cytosine deaminase activity and vector of the disclosure provide comparable or better expression, and hence killing, of infected rat RG2 (A) or U87 cells (B) compared to wild type yCD activity (T5.0007), when infected cells are exposed to increasing levels of 5-FC.
Figure 5B:
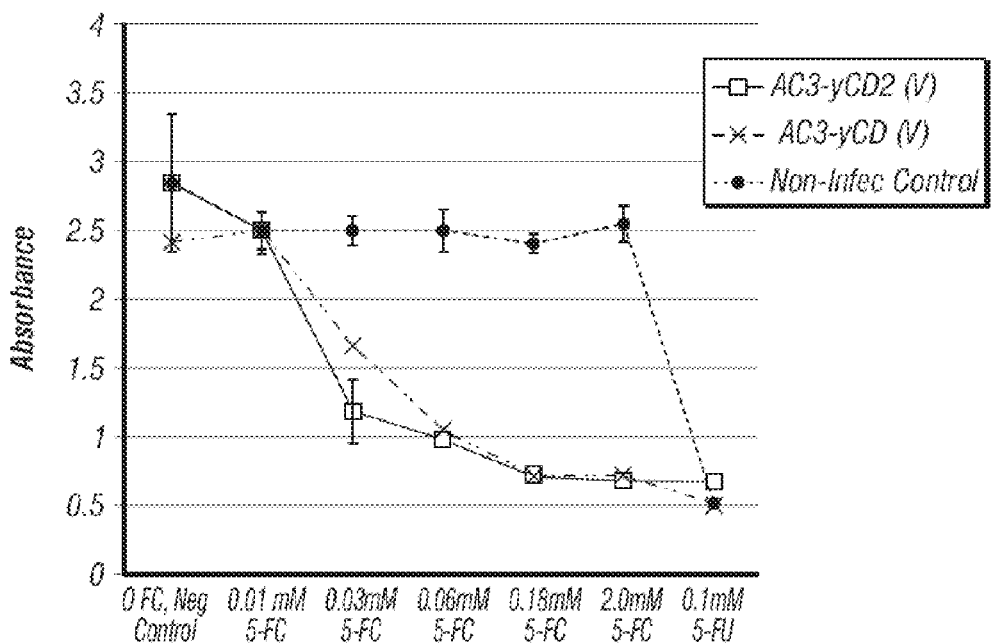

In in-vitro cell culture experiments, the experiments demonstrate that the cytosine deaminase in cells expressing the yCD2 protein is at least as active as that from cells expressing the wild type yCD protein, by performing 5-FC titrations on RG2 rat cells (FIG. 5A) or U-87 cells (FIG. 5B) infected either with virus made from pAC3-yCD2/T5.0002) [AC3-yCD2 (V)] from pAC3-yCD/T5.0007 [AC3-yCD(V)] or the other vectors. Briefly, for U-87 cells, 5 days post infection at a multiplicity of infection of 0.1 (i.e. 100% infected) with either AC3-yCD (wild type CD) vector or AC3-yCD2 (thermostabilized & codon optimized) vector were subject to increasing amounts of 5-FC or 0.1 mM of 5-FU as a positive control for 8 days. On day 8 of 5-FC treatment, cell cultures were assessed for viability using an MTS assay (Promega CellTiter 96 AQUEOUS One Solution Proliferation Assay). Data shows comparable killing between the two retroviral vectors at increasing doses of 5-FC treatment. The RG2 cultures were treated similarly and also show if anything a slight shift in the killing curve towards lower concentration of 5-FC for virus from T5.0002CD expression assay. U87 cells were transduced at a multiplicity of infection (MOI) of 0.1, cultivated for 5 days to allow viral spread and cells from day 5 post transduction were harvested. The cells were then collected by centrifugation at 800×g for 5 min. The supernatant was aspirated away from the cell pellet and washed with 5 mL of phosphate buffered saline (PBS) and again centrifuged at 800×g for 5 min. The resulting cell pellet was taken up in 1.5 mL of PBS, resuspended by passage through a pipette tip and placed in a freezer at −20 C. Cells were lysed by a freeze/thaw method. Previously resuspended cells were allowed to thaw at room temperature, passed through a pipette tip, mixed with protease inhibitor cocktail and again refrozen at −20 C. Previous to the enzyme assay, the sample was again thawed at room temperature and passed through a pipette tip. The suspension was then centrifuged at 14,000 rpm in a tabletop centrifuge for 5 min. The supernatant was decanted away from the pellet and placed in a fresh eppendorf tube and placed on ice. yCD enzyme activity was assessed by using an HPLC assay.

Figure 6:
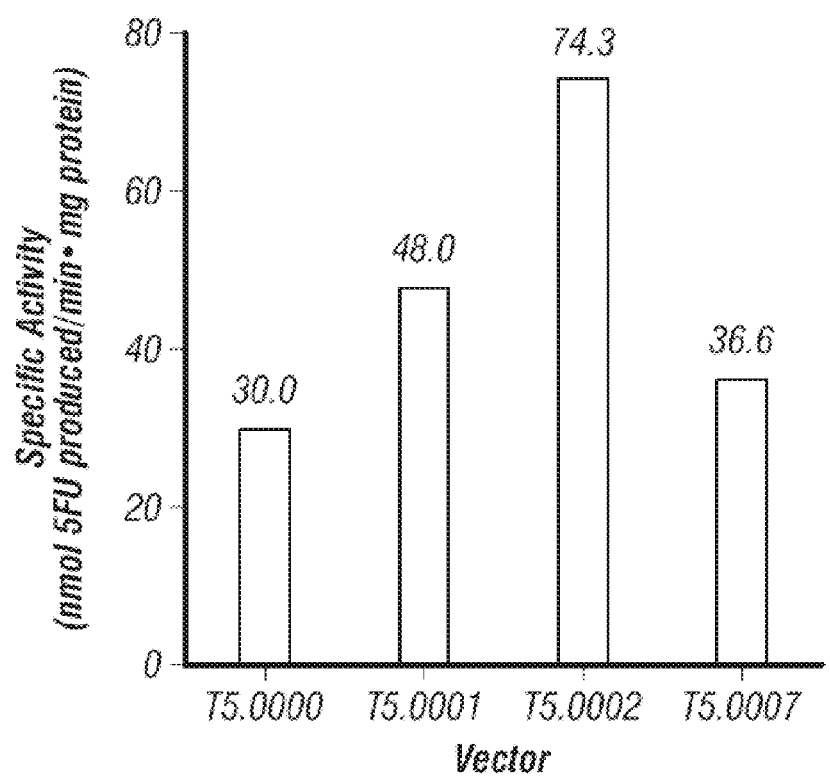
FIG. 6 shows that the specific activity in infected U87 cells of T5.0002 (yCD2) is greater than T5.0001 (partially optimized yCD) which is greater than T5.0007 (wt yCD).

The HPLC assay was performed on a Shimadzu LC20AT unit connected in series with a photoarray detector and autoinjector. The solid phase was a Hypersil BDS C18 HPLC column with a 5 um sphere size and 4.0×250 mm column dimensions. The mobile phase was 50 mM ammonium phosphate, pH 2.1, containing 0.01% tert-butylammonium perchlorate and 5% methanol; the system was equilibrated at 22 C. All reagents were ACS grade and solvents were HPLC grade. A reaction mix was made consisting of 800 μL with a final concentration of 0.125 mg/mL 5FC (1 mM) in PBS and placed in a 1.5 mL autosampler vial. The reaction was then initiated by adding 200 uL of each cell lysate. The reaction/autosampler vials were placed in the auto sampler and 5 uL of the reaction mixture was injected. Time points were taken periodically by retrieving a 5 uL aliquot from each reaction vial and analyzing on the HPLC column. The conversion rates of 5FC to 5FU were calculated by comparing the peak areas with known amounts from a previously generated standard curve of 5FU. The rate of 5FC conversion to 5FU was derived by plotting the amount of 5FU (in nmol) generated against its corresponding time interval. Protein concentration for the cell sample was derived and the Specific Activity of the cell lysate samples were calculated by dividing the conversion rate (nmol/min) by the amount of protein used in the assay in mg. FIG. 6 shows the specific activity of various vectors after 5 days on transduction at an MOI of 0.1. The data demonstrate that pACE-yCD (T5.0000)<pAC3-yCD1 (T5.0001)<pAC3-CD2 (T5.0002) in terms of the specific activity of cytosine deaminase in tissue culture cells.

Example 7

Tumors Treated with the Fully Modified CD Gene (yCD2) are Eliminated more Efficiently than Tumor Treated with the Unmodified Yeast CD Gene, and do not Recur (PR-01-08-001)

To determine which vector construct gives rise to the most effective vector in a subcutaneous mouse/human xenograft model. Three different constructs were evaluated: T5.0001 (partially modified CD); T5.0007 (unmodified yeast CD gene); T5.0002 (fully modified yCD2 gene). Tumor growth, survival and tumor regression post 5-FC prodrug administration was evaluated in a subcutaneous model of human glioma (U87) in immunodeficient mice. Two different 5-FC concentrations were evaluated to determine a dose response seen between 5-FC and the tumor-vector constructs.

A total of 12 groups consisting of 9-11 female mice per group were studied. All mice underwent right dorsal flank implantation on Day 0 with either: a 98% mixture of an uninfected U-87 tumor cell line and a 2% mixture of a U-87 cell line that has been infected with one of three TOCA 511 vector constructs, T5.0002, T5.0001, T5.0007; or an uninfected control U-87 cell line (100%). Mice were inoculated with 2×10e6 cells/mouse. Mice in groups 1-3 had uninfected U87 cells, groups 4-6 had U87 cell mixture containing transduced T5.0002 U87, groups 7-9 had U87 cell mixture containing transduced with T5.0001, and groups 10-12 had U87 cell mixture containing transduced with T5.0007. The tumors were allowed to grow for 6 days, until tumor size was approximately 100 mm$^3$. Each vector dose group of mice was randomized to receive one of two doses of 5-FC (200 or 500 mg/kg/day), administered as a single IP injection, beginning on Day 6, or no 5-FC. 5-FC administration continued daily for 28 consecutive days. Surviving mice after day 29 were evaluated for tumor size and then sacrificed on varying days with tumors, if present, extracted for analysis. At day 29, mice from group 4-12 were re-randomized and the mice were subdivided into 2 subgroups (either continued on 5-FC to monitor tumor regression or discontinued 5-FC treatment to monitor tumor regrowth).

Results:

Tumors treated with T5.0002, T5.0000 and T5.0007 all demonstrated tumor regression to undetectable at 200 and 500 mg/kg dose at day 29. All T5.0002 treated animals did not reform tumors when 5FC treatment was discontinued, out to 39 days. In contrast some tumors treated with T5.0001 and T5.0007 did recur by the 39 day time point. The experiment was terminated at day 39.

Conclusion:

T5.0002 plus 5-FC is a more effective antitumor therapy than T5.0001 or T5.0007 plus 5-FC.

Example 8

Tumor Explants have Multiple Copies of the Vector Genome and Show Continued Susceptibility to Super-Infection In order to examine in more detail the mechanism of action of the replicating retrovirus tumors from some animals in the mouse and human tumor models described in example 9 (athymic nude-Foxn1^nu (nude) mice with Human U87 intracranial implants) and example 10 (BALB/c mice with syngeneic CT26 intracranial implants) were explanted and examined for 5-FC sensitivity, vector copy number/diploid genome, and CD protein expression.

Explant Assignments.

The experimental design is summarized below. The study consisted of 5 tumor explants. The history of each tumor removed for implantation is given below.

Explant History:

| Animal # | Study | Treatment | # of 5-FC dosings before explant | Cell Type | Dosing regimen |
|---|---|---|---|---|---|
| 833 | Example 9 FIG. 8 | AC3-yCD2(V) E6 + 5-FC | 4 | Human U87 | QD, 7 days every 21 days |
| 953 | Example 9 FIG. 8 | AC3-yCD2(V) E5 + 5-FC | 4 | Human U87 | QD, 7 days every 21 days |
| 969 | Example 9 FIG. 8 | AC3-yCD2(V) E5 + 5-FC | 4 | Human U87 | QD, 7 days every 21 days |
| 31 | Example 10 FIG. 9 | AC3-yCD2(V) E5 + 5-FC | 3.5 | Mouse CT26 | BID 7 days, every 17 days |
| 61 | Example 10 FIG. 9 | AC3-yCD2(V) E4 + 5-FC | 3 | Mouse CT26 | BID 7 days, every 17 days |

The 5-FC cell killing assays were carried out as described in Example 5 above, measuring viability after 8 days of 5-FC treatment.

Copy number/microgram of DNA was determined by PCR as described for the vector titering assay in Example 5, and converted to copy number/diploid genome by dividing by 150,000, the approximate number of diploid mouse/human genomes in 1 microgram of genomic DNA. Western Blot analysis was performed on 1E6 cells/lysate in RIPA buffer using antibodies from clone 83A25 for GP70 and Abcam anti-CD antibody ab3525 for the CD protein. Cell explants underwent super-infection procedures with a AC3-eGFP(V) and a mock procedure to determine which explants were potentially further infectable. The extent of GFP expression was measured by FACS analyses, with uptake and expression of GFP indicating the relative susceptibility to further infection.

Results. 5-FC Cell Killing Assay and Copy Number of Integrated Vector.

Cultured explants were tested for 5-FC sensitivity by generating a killing profile from treated cell lines at varying 5-FC concentrations (summarized in the Table below). Results from the killing profile measured by MTS viability assay show that U87 human tumors derived from animals #833, 953, 969 on average ($IC_{50}$=0.009 mM) had a similar response compared to an in vitro U87 positive control ($IC_{50}$=0.008 mM) to 5-FC treatment. Analysis of CT26 murine tumors (Example 10) showed that the 5-FC responsive animal #61 had an $IC_H$ of 0.003 mM, which is similar to in vitro 100% transduced CT26 results ($IC_{50}$=0.001 mM). Animal #31 was poorly responsive to 5-FC. PCR results for copy number per cell are also shown in the table below.

| Animal # | Study | 5-FC sensitivity IC50 (mM) | Vector copy number per diploid genome |
|---|---|---|---|
| 833 | Example 9 | 0.009 | 22.3 |
| 953 | Example 9 | 0.009 | 9.6 |
| 969 | Example 9 | 0.009 | 18.7 |
| 61 | Example 10 | 0.003 | 6.0 |
| 31 | Example 10 | Not sensitive | 0.9 |

Western Blot Analysis of GP70 and CD Protein Expression.

Further analysis of cells by western blot from the CT26 study showed that both tumor explants derived from mice #31 and #61 had observable GP70 protein expression when using U87+AC3-yCD2 (V) infected lysates as a reference positive control.

However, analysis of CD expression showed that only #61 still had observable CD expression. Cells from #31 were run in duplicate wells (#31 (A) and #31 (B)) to verify negative CD gene expression results.

GFP Expression after AC3-eGFP(V) Transduction.

Attempts to transduce explants with an MLV vector expressing GFP showed that U87 tumors derived from animals #833, 953, 969 were scarcely transducible (<0.5%). CT26 explanted tumor cells derived from animal #61 could be partially transduced (7% GFP positive) while explanted cells from animal #31 could not.

All U87 gliomas isolated from the brains of nude mice after 4 full cycles of 5-FC treatment were still sensitive to 5-FC treatment in vitro with an $IC_{50}$ the same as in vitro transduced U87 and, surprisingly, showed multiple vector superinfections had taken place. Two CT26 tumors were isolated from BALB/c mice after 3 and 3.5 cycles of 5-FC treatment. Of the two, only one tumor showed 5-FC sensitivity while the other did not. Further analysis showed that the 5-FC resistant tumor is refractory to further MLV transduction, expresses GP70 but no longer expresses the CD, and has low copy number compared to the other CT26 and all U87 explants tested. These observations show that whereas a virus that has undergone a deletion of the CD gene behaves as expected for a normal retrovirus and excludes further infection, cells infected with vector carrying the CD transgene behave atypically and allow multiple superinfections (range: 6.0-23.3, mean 14.5 copies per diploid genome). Typical tumors are not diploid but are polyploid with a genome larger than the diploid genome. This would further increase the actual vector copy number per cell. The multiple vector copy numbers contributes to the therapeutic effect as more of the protein derived from the transgene (in this case CD) is produced than from a single vector integration. It also means that in general, even if some members of a viral vector population undergo rearrangements, other members will donate protein activity (in this case sensitivity to 5-FC). The experiments described here also provide a method of testing a recombinant replication competent retrovirus for the property of multiple infections of a target cell population.

Example 9

Direct Measurement from Excised Tumors Treated with AC3-yCD2 (V) Shows Unexpectedly High Levels of Viral Vector Copies Per Genome and Susceptibility to Superinfection in the Syngeneic Tu2449 Glioma Model Objective.

This study was conducted to compare the efficacy of two dose levels of AC3 (V)-yCD2 (aka Toca511) delivered via IC injection in combination with 5-FC treatment in a TU-2449 glioma tumor bearing, immunocompetent mouse model, and examined survival in the setting of active tumor growth. TU-2449 cells implanted IC in syngeneic B6C3F1 mice have been used as an experimental murine glioma model. This model was also used for survival and short term (15-18 day) experiments where tumors were implanted, treated with vector and dosed short term with 5-FC then excised for further characterization of gene copy number and CD activity.

Mice.

Female B6C3F1 mice (age ~8 weeks) were purchased from Harlan (Indianapolis Ind.). Mice were acclimated for 7 days after arrival.

Mice underwent surgical placement of an indwelling guide cannula with a 3.0 mm projection implanted into the right striatum, and fitted with a cap containing a 3.5 mm projection. The stereotaxic coordinates were AP=+0.5 mm, ML=−1.8 mm (from bregma).

Cells.

TU-2449 cells (Smilowitz et al. J Neurosurg. 2007 106: 652-659 2007) derived originally from Glial fibrillary acidic protein (GFAP)-v-src transgenic mice, were cultured in Dulbecco's modified Eagles medium with 10% fetal bovine serum, sodium pyruvate, and Glutamax (Hyclone, Logan Utah, and Invitrogen, San Diego Calif.). Cells were resuspended in PBS (Hyclone, Logan Utah) for implantation. TU-2449 cells (1E4 in 1 µL) were infused at 0.2 µL per minute (5 minutes, followed by a hold of 5 minutes) IC through an injection cannula with a 3.5 mm projection inserted through the guide cannula.

The study consisted of 6 groups of female mice (see Table below). On day 0, mice from Groups 1, 3, 4, 6, and 7 underwent intracranial implantation of 1E4 TU-2449 cells. Group 8 mice were not implanted with tumor. On Day 4, mice were injected (IC; 5 µL/mouse) with vehicle (Group 1); IC with AC3-yCD2 (V) at 1.7E5 TU/g (Groups 6, 7); IC with AC3-yCD2 (V) at 1.7E6 TU/g (Groups 3, 4); Group 8 mice were not treated. Starting on Day 10, mice were treated IP BID for 4 consecutive days with PBS (Groups 1, 3, 7) or 5-FC (500 mg/kg/dose, Groups 4, 6, 8). Cycles of 4 days BID treatment with PBS or 5-FC followed by 10 days of viral spread were repeated. Survival analysis to Day 180 was performed on 10 mice each from Groups 3-7.

Group Assignments

| Group | Treatment | N per analysis category | |
|---|---|---|---|
| | | Survival | Scheduled Sacrifice |
| 1 | Control (vehicle injection) + PBS | | 1 at day 10 |
| 3 | AC3-yCD2(V) E6 + PBS | 10 | |
| 4 | AC3-yCD2(V) E6 + 5-FC | 10 | 3 at day 10, 24, 38, and 52 |
| 6 | AC3-yCD2(V) E5 + 5-FC | 10 | 3 at day 10, 24, 38, and 52. |
| 7 | AC3-yCD2(V) E5 + PBS | 10 | |
| 8 (no tumor) | 5-FC | | 1 at day 10, 24, 38, and 52 |
| | TOTAL | 40 | 29 |

AC3-yCD2 (V) (5 µL) was infused at 0.33 µL per minute (15 minutes, followed by a hold of 5 minutes) intracranially through an injection cannula with a 3.5 mm projection inserted through the guide cannula. 5-FC (500 mg/kg/dose) or PBS (800 µL) was administered IP BID for 4 consecutive days starting at days 10, 24, 38, and 52.

Example 10

Short Term Experiments to Determine the Level of Viral Genome and Super-Infection in Tu2449 Tumors In Vivo The study consisted of 6 groups of female mice (see Table below). All groups underwent intracranial administration into the right striatum of 1E4 TU-2449 cells administered/mouse on Day 0. At Day 4, all groups received intracranial/intratumoral administration of AC3-YCD2 (V) vector at 2.4E6 TU/5 ul (Lot#T511019) or PBS buffer control. Two days of BID 5-FC administration began when the mice started losing weight (approximately 15 days post-tumor implantation). Group 5 had 5-FC delivered by oral gavage (OG) and all other groups IP. One more dose of 5-FC was given 1 hour before sacrifice the following day. From each brain, the tumor was isolated and processed directly into RIPA buffer for analysis of 5-FC and 5-FU by HPLC. A small portion of the tumor was retained for western blot analysis.

Group Assignments and Dose Levels

| Group | Treatment | Route | TX | Route | Dosing | N |
|---|---|---|---|---|---|---|
| 1 | AC3-YCD2(V) | IC | NONE | N/A | N/A | 3 |
| 2 | PBS | IC | 5FC | IP | 250 mg/kg | 4 |
| 3 | PBS | IC | 5FC | IP | 500 mg/kg | 2 |
| 4 | AC3-YCD2(V) | IC | 5FC | IP | 250 mg/kg | 3 |
| 5 | AC3-YCD2(V) | IC | 5FC | OG | 250 mg/kg | 2 |
| 6 | AC3-YCD2(V) | IC | 5FC | IP | 500 mg/kg | 2 |
| | | | | | Total animals | 16 |

IC—intracranial; IP—intraperitoneal; OG—oral gavage

AC3-yCD2 (V) (5 µL) was infused at 0.33 µL per minute (15 minutes, followed by a hold of 5 minutes) intracranially at the same coordinates as TU-2449 cells were injected. 5-FC or PBS was administered IP or OG BID for 2 consecutive days and 1 hour before sacrifice.

Tissue Processing Procedures.

From each brain, tumors were isolated and trimmed if large enough for multiple analyses (more than 0.05 g). Tumors sections for HPLC analysis were crushed in a 1.5 mL centrifuge tube using a plunger from a 1 mL syringe. Crushed samples were mixed with 150 uL RIPA buffer and vortexed vigorously for 10 minutes. Samples were spun at 4° C. at 20000 rcf for 10 minutes. Supernatants were removed and mixed thoroughly with 150 uL of 10% trichloroacetic acid and spun as above. Supernatants were removed for analysis by the Agilent HPLC unit with a Hypersil BDS C18 column run isocratically at 1 mL/min with 95% Buffer A containing 50 mM ammonium phosphate and 0.1% tetra-n-butylammoniumperchlorate with pH adjustment of the buffer to 2.1 with phosphoric acid and 5% Solvent B which is 100% methanol (see WI RD-053). The run time is 5 minutes with each sample run twice. The photodiode detector array scans from 190 to 350 nm with chromatograms selected to display at 285 nm for 5-fluorocytosine and 264 nm for 5-fluorouracil. Data was expressed in relative milli absorbance units (mAU) of peak area from the chromatograms.

Protein Gels and Western Blots.

When sufficient tumor was available, tumor fragments for protein gels and Western blots were mixed with a separate aliquot of RIPA lysis buffer, and 20 ug of total protein from each sample was electrophoresed on polyacrylamide gels, Western blotted and the blot developed with sheep anti-yeast CD antibody as in Example 10. Western blot data was scanned and quantified using BioRad Quantity One software (version 4.6.7).

QPCR on Tumor Fragments.

Remaining pellets, after supernatants were removed for HPLC analysis, were extracted for genomic DNA. Samples were analyzed by qPCR for proviral integration copy number using primers and probe for MLV LTR as in example 10. Samples were also analyzed in parallel using previously characterized primers and probes for the amphotropic env gene (Env2) and the CD gene (yCD2).

yCD2 Primer and Probe Set:

```
5' AC3-YCD2(V) yCD2 Primer:
                                    (SEQ ID NO: 49)
ATCATCATGTACGGCATCCCTAG 3' AC3-YCD2(V) yCD2 Primer:
                                    (SEQ ID NO: 50)
TGAACTGCTTCATCAGCTTCTTAC yCD2 Probe:
                                    (SEQ ID NO: 51)
/5FAM/TCATCGTCAACAACCACCACCTCGT/3BHQ_1/
```

These primers and probe target and amplify the CD gene exclusively.

Env2 Primer and Probe Set:

```
Env2-Forward:
                                    (SEQ ID NO: 52)
AACCTCAACCTCCCCTACAAGT Env2-Reverse:
                                    (SEQ ID NO: 53)
GTTAAGCGCCTGATAGGCTC Env2-Probe:
                                    (SEQ ID NO: 54)
/5TEX615/AGCCACCCCCAGGAACTGGAGATAGA/3IAbRQSp/
```

These primers and probe target and amplify the envelope (Env) gene exclusively.

Results. Survival Analysis.

The median survival of AC3-yCD2 (V) control groups treated with PBS (Group 3 and 7) was approximately 33-38 days. The survival medians of mid and high dose AC3-yCD2 (V) in combination with 5-FC (Group 6 and 4) were not reached before sacrifice at 189 days. Log-Rank (Mantel-Cox) pair-wise comparison showed no difference in survival between the two control groups; AC3-yCD2 (V) E5 dose plus PBS (Group 7) and AC3-yCD2 (V) E6 dose plus PBS (Group 3).

AC3-yCD2 (V) treatment at both dose levels in combination with 5-FC resulted in prolonged survival. A statistically significant survival advantage was observed for AC3-yCD2 (V) E5 plus 5-FC (Group 6) treated mice compared to vector plus PBS control (Group 7) mice ($p<0.0354$, hazard ratio 0.2605, 95% CI 0.07439 to 0.9119). A statistically significant survival advantage was observed for AC3-yCD2 (V) E6 plus 5-FC (Group 4) treated mice compared to vector plus PBS control (Group 3) mice ($p<0.0036$, hazard ratio 0.1130, 95% CI 0.02598 to 0.4911).

Example 11

Short Term Experiments to Determine the Level of Viral Genome and Super-Infection in Tu2449 Tumors In Vivo HPLC Analysis.

In vivo conversion of 5-FC to 5-FU was detected by HPLC in all groups dosed with Toca511 and 5-FC. Group 1 that was given AC3-yCD2 (V) but no 5-FC had neither 5-FC nor 5-FU detectable signals as expected. The small counts observed (47-84) for 5-FC is attributable to background from nearby peaks on the chromatography trace. Groups 2 and 3 that were not dosed with AC3-yCD2 (V) but dosed with varying levels of 5-FC had detectable 5-FC signals but no signal for 5-FU. Group 4 mice dosed with AC3-yCD2 (V) and 5-FC IP and Group 5 mice dosed with AC3-yCD2 (V) and 5-FC OG had comparable signal levels of 5-FU and very low or background levels of 5-FC. Group 6 mice dosed with Toca-511 and high levels of 5-FC showed readily detectable levels of 5-FU and low signal for 5-FC.

CD Western Blot Analysis.

Tissue samples from isolated TU-2449 tumors were processed for western blot analysis of CD expression. All groups (1, 4, and 5) treated with AC3-yCD2 (V) had readily observable CD expression while Group 2 that was not given AC3-yCD2 (V) did not have detectable CD expression.

PCR Analysis of Genomic DNA Isolated from Tumors.

The remaining pellets, after supernatants were removed for HPLC analysis, were extracted for genomic DNA. Samples were analyzed by quantitative PCR for proviral integration using the standardized assay and MLV-LTR primers and probe. Parallel assays using the envelope and CD gene primers and probes analyses gave similar C(t) values showing that the viral genome appeared quite stable. An in vitro transduced cell line served as positive control. The negative control was genomic tumor DNA from Group 2 that was not dosed with AC3-yCD2 (V) and did not have detectable signal for any of the qPCR protocols.

Table of relative CD protein levels, viral vector copy #, and relative levels of 5-FU production

| Group   | Mouse # | Relative CD protein levels | Copies#/diploid genome | 5-FU (relative peak area units) |
|---------|---------|----------------------------|------------------------|--------------------------------|
| Group 1 | 194     | 21,746                     | 1.4                    | 0                              |
|         | 199     | No Data                    | 14.6                   | 0                              |
| Group 2 | 191     | 162                        | 0                      | 0                              |
|         | 187     | 75                         | 0                      | 0                              |
|         | 188     | −453                       | 0                      | 0                              |

-continued

| Group | Mouse # | Relative CD protein levels | Copies#/diploid genome | 5-FU (relative peak area units) |
|---|---|---|---|---|
| Group 4 | 185 | 17,349 | 1.8 | 1642 |
|  | 200 | 45,446 | 7.3 | 1576 |
| Group 5 | 189 | 25,417 | 3.7 | 942 |
|  | 198 | 23,660 | 6.6 | 1371 |

For samples with enough starting material for all three analyses to be done, the relationship between integrated MLV copy number, expression of CD, and the amount of 5-FC to 5-FU conversion is summarized in the above table (199 did not have material for Western analysis). The relative CD protein levels (estimated from Western blots) vary over a three-fold range and the DNA copy number over a 5-fold range. There is some correlation between DNA copy number and relative level of CD expression. All of the tumors have vector copy numbers/genome above 1, showing that even at this early time-point after vector administration (13-14 days) superinfection of tumor cells is a usual occurrence, and may contribute to observed therapeutic effects. The CD values displayed represent the values after average background correction, and the Group 2 numbers represent the variability in that background.

This study supports the proposed mechanism of action and shows that this efficacy can be attributed to the conversion of the 5-FC prodrug into the anticancer drug 5-FU after delivery of the CD gene by AC3-yCD2 (V). Using the TU-2449 mouse glioma model, AC3-yCD2 (V) treatment in combination with 5-FC resulted in efficient in vivo conversion of 5-FC into 5-FU. 5-FC was converted efficiently into 5-FU at two dose levels (500 and 250 mg/kg) as 5-FC levels were at least ten fold lower than the controls, and 5-FU levels were readily detectable in AC3-yCD2 (V) treated but not in the untreated controls. IP or OG delivery of 5-FC did not affect the efficiency of conversion. Tumors isolated from mice given AC3-yCD2 (V) had observable expression of CD protein that had some correlation with the numbers of copies of the vector genome. The number of integrated vector genomes ranged from 1.4 to 15 copies/diploid genome (mean: 5.9). The infection here was the result of about 12 days infection and previous experiments with GFP vectors in other models suggest that this corresponds to infection of approximately 50% of the cells in the tumor, giving an adjusted vector copy number/cell of 11.8 copies/diploid genome. Typical tumors are not diploid but are triploid or further polyploid with a genome larger than the diploid genome. This would further increase the actual vector copy number per cell. The experiments described here also provide a method of testing a recombinant replication competent retrovirus for the property of multiple infections of a target cell population. These observations support the conclusion that AC3-yCD2 (V) is efficiently delivering a functional CD gene for expression in glioma cells. In the efficacy study with this model, almost no spread of vector from the site of injection (tumor in the right cerebrum) was observed in the first 24 days. The observations in this study show that over the same initial period of time there is extensive viral vector infection of the tumor, showing that infection is quite tumor specific, and that already at this early time-point there is extensive super-infection of the tumor cells by the viral vector.

Example 11

Clonal Analyses of HT1080 Cell Line Infected with AC3-yCD2 (V) Shows that the Majority of the Clones have Multiple Copies of the Viral Vector Genome and were Susceptible to Super-Infection The human sarcoma line HT1080 (ATCC: CCL 121) was grown in tissue culture under standard culture conditions. 2E7 cells were infected with AC3-yCD2 (V) made by transient transfection on 293 cells, at a multiplicity of 0.1, allowed to grow for 14 days, and frozen down as a pool. About 1 month later cells were thawed and clonal cell lines from this culture were isolated by limiting dilution in 96 well dishes at 0.3 cells/well. The clones that grew out were expanded and analyzed by qPCR with the MLV LTR primers for vector genome copy number per microgram DNA in triplicate. This was converted to copy number/diploid genome by dividing by 150,000, as described in example 10. The Table below lists the clones that were analyzed and the corresponding copy number for the viral vector genome. Only 1 of 10 clones (13-5) has approximately 1 copy of the viral genome per diploid genome. The range was 0.9 to 20.4 copies/cell and the mean copy number was 10.6 copies/cell. Typical tumors are not diploid but are triploid or further polyploid with a genome larger than the diploid genome. This would further increase the actual vector copy number per cell. It is well known that normally a viral infection of this nature leads to a single or few copies of viral genome/cell, due to resistance to superinfection through receptor masking or down regulation (see, for example, Ch3 p104 of "Retroviruses" J M Coffin, S H Hughes & H E Varmus, 1997 Cold Spring Harbor Laboratory Press, Cold Spring Harbor N.Y.).

Listing of viral vector copy number in infected HT1080 clones infected with AC3-yCD2 and expanded.

| Sample # | Test article | Average copy number/genome |
|---|---|---|
| 1 | Negative control (HT1080) | 0 |
| 2 | Positive control (recently transduced HT1080 pool) | 1.89 |
| 3 | Clone # 3-5 | 18.26 |
| 4 | Clone# 4-1 | 5.28 |
| 5 | Clone# 7-1 | 18.87 |
| 6 | Clone# 8-3 | 14.04 |
| 7 | Clone# 9-1 | 15.29 |
| 8 | Clone# 10-1 | 9.73 |
| 9 | Clone# 11-1 | 20.44 |
| 10 | Clone# 12-6 | 6.08 |
| 11 | Clone# 13-5 | 0.93 |
| 12 | Clone# 19-2 | 5.24 |

Therefore this is an unexpected and surprising result that confirms the in vivo tumor model data of Examples 30 and 31. More particularly, the data demonstrate that this virus allows multiple super-infections in the great majority of the cells it infects, unlike normal MLV infection. The experiments described here also provide a method of testing a recombinant replication competent retrovirus for the property of multiple infections of a target cell population.

A number of embodiments of the disclosure been described. Nevertheless, it will be understood that various modifications may be made without departing from the spirit and scope of the disclosure. Accordingly, other embodiments are within the scope of the following claims.

What is claimed is:

1. An isolated polynucleotide comprising:
 a human codon optimized polynucleotide wherein the human codon optimized polynucleotide encodes a polypeptide comprising the sequence of SEQ ID NO:4, wherein the polypeptide comprises cytosine deaminase (CD) activity.

2. The isolated polynucleotide of claim 1, wherein the human codon optimized polynucleotide comprises the sequence as set forth in SEQ ID NO:3.

3. The isolated polynucleotide of claim 1, further comprising a UPRT or OPRT polynucleotide encoding a polypeptide having UPRT or OPRT activity operably linked to the polypeptide having CD activity wherein the UPRT or OPRT polynucleotide is separated from the polynucleotide encoding the polypeptide having CD activity by a linker.

4. The isolated polynucleotide of claim 3, wherein the UPRT or OPRT polynucleotide is codon optimized.

5. An isolated polynucleotide comprising: a first coding sequence comprising SEQ ID NO:3 encoding a polypeptide having cytosine deaminase; and a second coding sequence encoding an UPRT or an OPRT polypeptide wherein the first coding sequence is operably linked to the second coding sequence.

6. The isolated polynucleotide of claim 5, wherein the first and the second coding sequences are separated by a nucleic acid sequence encoding a peptide linker.

7. The isolated polynucleotide of claim 5, wherein the polynucleotide encodes a polypeptide comprising the sequence as set forth in SEQ ID NO:12, 14, or 16.

8. A vector comprising the polynucleotide of claim 1.

9. The vector of claim 8, wherein the vector is a plasmid.

10. An in vitro host cell containing the vector of claim 9.

11. The vector of claim 8, wherein the vector is an expression vector.

12. The vector of claim 8, wherein the vector is a viral vector.

13. The vector of claim 12, wherein the viral vector is a replication competent retrovirus.

14. An in vitro host cell comprising a polynucleotide of claim 1.

15. The in vitro host cell of claim 14, wherein the host cell is a human cell.

16. The in vitro host cell of claim 15, wherein the host cell is a cell comprising a cell proliferative disorder.

17. The in vitro host cell of claim 16, wherein the host cell is obtained from a glioblastoma multiforme.

18. The in vitro host cell of claim 14, wherein the host cell is a stably transformed human cell.

19. A recombinant replication competent retrovirus (RCR) comprising:
 a retroviral GAG protein;
 a retroviral POL protein;
 a retroviral envelope;
 a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell and operably linked to a gag nucleic acid that encodes the GAG protein, a pol nucleic acid that encodes the POL protein and an env nucleic acid that encodes the retroviral envelope;
 a cassette comprising an internal ribosome entry site (IRES) operably linked to a heterologous nucleic acid comprising a polynucleotide of claim 1, wherein the cassette is positioned 5' to the 3' LTR and 3' to the env nucleic acid encoding the retroviral envelope; and
 cis-acting sequences necessary for reverse transcription, packaging and integration in a target cell.

20. The retrovirus of claim 19, wherein the retroviral polynucleotide sequence is a modified murine leukemia virus (MLV), Moloney murine leukemia virus (MoMLV), Feline leukemia Virus or Gibbon ape leukemia virus (GALV) retroviral polynucleotide.

21. The retrovirus of claim 20, wherein the MLV is an amphotropic MLV.

22. The retrovirus of claim 19, wherein the retrovirus is a gammaretrovirus.

23. The retrovirus of claim 19, wherein the promoter sequence is associated with a growth regulatory gene.

24. The retrovirus according to claim 19, wherein the promoter sequence comprises a tissue-specific promoter sequence.

25. The retrovirus according to claim 19, wherein the promoter comprises a CMV promoter.

26. The retrovirus of claim 19, wherein the promoter comprises a sequence as set forth in SEQ ID NO:19 or 20 from nucleotide 1 to about nucleotide 582.

27. The retrovirus of claim 19, wherein the promoter comprises a CMV-R-U5 domain polynucleotide.

28. The retrovirus of claim 27, wherein the CMV-R-U5 domain comprise the immediately early promoter from human cytomegalovirus linked to an MLV R-U5 region.

29. The retrovirus of claim 28, wherein the CMV-R-U5 domain polynucleotide comprises a sequence as set forth in SEQ ID NO:19, 20, or 22 from nucleotide 1 to nucleotide 1202 or sequences that are at least 95% identical to a sequence as set forth in SEQ ID NO:19, 20, or 22, wherein the polynucleotide promotes transcription of a nucleic acid molecule operably linked thereto.

30. The retrovirus of claim 19, wherein the gag of the polynucleotide is obtained from a gammaretrovirus.

31. The retrovirus of claim 30, wherein the gag nucleic acid comprises the sequence from nucleotide number 1203 to nucleotide 2819 of SEQ ID NO: 19 or a sequence having at least 95%, 98%, 99% or 99.8% identity thereto.

32. The retrovirus of claim 19, wherein the pol of the polynucleotide is obtained from a gammaretrovirus.

33. The retrovirus of claim 32, wherein the pol nucleic acid comprises the sequence from nucleotide number 2820 to nucleotide 6358 of SEQ ID NO:19 or a sequence having at least 95%, 98%, 99% or 99.9% identity thereto.

34. The retrovirus of claim 19, wherein the env nucleic acid comprises the sequence from nucleotide number 6359 to nucleotide 8323 of SEQ ID NO:19 or a sequence having at least 95%, 98%, 99% or 99.8% identity thereto.

35. The retrovirus of claim 19, wherein the IRES is from an encephalomyocarditis virus.

36. The retrovirus of claim 35, wherein the IRES comprises the sequence from nucleotide number 8327 to nucleotide 8876 of SEQ ID NO:19 or a sequence having at least 95%, 98%, or 99% identity thereto.

37. The retrovirus of claim 19, wherein the heterologous nucleic acid comprises a polynucleotide having the sequence as set forth in SEQ ID NO:3, 5, 11, 13, 15 or 17.

38. The retrovirus of claim 19, wherein the heterologous nucleic acid comprises nucleotides 8877-9353 of SEQ ID NO: 19.

39. The retrovirus of claim 38, wherein the 3' LTR is obtained from a gammaretrovirus.

40. The retrovirus of claim 39, wherein the 3' LTR comprises a U3-R-U5 domain.

41. The retrovirus of claim 40, wherein the 3' LTR comprises nucleotides 9405-9353 SEQ ID NO:19 or a sequence that is at least 95%, 98% or 99.5% identical thereto.

42. The retrovirus of claim 19, wherein the retroviral polynucleotide comprises the sequence as set forth in SEQ ID NO:19, 20, or 22.

43. An isolated polynucleotide comprising from 5' to 3':
a CMV-R-U5 fusion of the immediate early promoter from human cytomegalovirus to an MLV R-U5 region;
a PBS, primer binding site for reverse transcriptase;
a 5' splice site;
ψ packaging signal;
a gag coding sequence for MLV group specific antigen;
a pol coding sequence for MLV polymerase polyprotein;
a 3' splice site;
a 4070A env coding sequence for envelope protein of MLV strain 4070A;
an internal ribosome entry site (IRES) from encephalomyocarditis virus;
a modified cytosine deaminase comprising the polynucleotide of claim 1;
a polypurine tract; and
a U3-R-U5 MLV long terminal repeat.

44. The polynucleotide of claim 43, wherein the retroviral polynucleotide comprises a sequence as set forth in SEQ ID NO:19, 20, or 22.

* * * * *